(12) United States Patent
Elson et al.

(10) Patent No.: US 7,868,139 B2
(45) Date of Patent: Jan. 11, 2011

(54) COMPOSITIONS AND METHODS FOR THE IDENTIFICATION AND TREATMENT OF IMMUNE-MEDIATED INFLAMMATORY DISEASES

(75) Inventors: Charles O. Elson, Birmingham, AL (US); Yingzi Cong, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 145 days.

(21) Appl. No.: 12/223,219

(22) PCT Filed: Jan. 24, 2007

(86) PCT No.: PCT/US2007/060996

§ 371 (c)(1),
(2), (4) Date: Oct. 3, 2008

(87) PCT Pub. No.: WO2007/087576

PCT Pub. Date: Aug. 2, 2007

(65) Prior Publication Data

US 2010/0129386 A1    May 27, 2010

Related U.S. Application Data

(60) Provisional application No. 60/762,063, filed on Jan. 24, 2006.

(51) Int. Cl.
*C07K 1/00* (2006.01)
(52) U.S. Cl. .......................... 530/350; 435/975
(58) Field of Classification Search ................. None
See application file for complete search history.

(56) References Cited

U.S. PATENT DOCUMENTS

| | | | |
|---|---|---|---|
| 6,821,739 B2 | 11/2004 | Braun | |
| 7,009,042 B1 | 3/2006 | Skeiky | |
| 7,361,733 B2 | 4/2008 | Hershberg | |
| 2002/0039599 A1 | 4/2002 | Lin | |
| 2002/0044938 A1 | 4/2002 | Fox | |
| 2003/0003516 A1 | 1/2003 | Robinson | |
| 2003/0031625 A1 | 2/2003 | Lin | |
| 2005/0208597 A1 | 9/2005 | Chan | |

FOREIGN PATENT DOCUMENTS

| | | | |
|---|---|---|---|
| WO | WO 91/18926 | | 12/1991 |
| WO | WO 03/053220 | * | 7/2003 |

OTHER PUBLICATIONS

Beckwith J, Cong Y, Sundberg JP, Elson CO, Leiter EH. (2005) Cdcs1, a major colitogenic locus in mice, regulates innate and adaptive immune response to enteric bacterial antigens. Gastroenterology. 129(5): 1473-1784.

Brandwein SL, McCabe RP, Cong Y, Waites KB, Ridwan BU, Dean PA, Ohkusa T, Birkenmeier EH, Sundberg JP, Elson CO. (1997) Spontaneously colitic C3H/HeJBir mice demonstrate selective antibody reactivity to antigens of the enteric bacterial flora. J Immunol. 159(1): 44-52.

Cohavy O, Harth G, Horwitz M, Eggena M, Landers C, Sutton C, Targan SR, Braun J. (1999) Identification of a novel mycobacterial histone H1 homologue (HupB) as an antigenic target of pANCA monoclonal antibody and serum immunoglobulin A from patients with Crohn's disease. Infect Immun. 67(12): 6510-6517.

Cong Y, Brandwein SL, McCabe RP, Lazenby A, Birkenmeier EH, Sundberg JP, Elson CO. (1998) CD4+ T cells reactive to enteric bacterial antigens in spontaneously colitic C3H/HeJBir mice: increased T helper cell type 1 response and ability to transfer disease. J Exp Med. 187(6): 855-864.

Cong Y, Konrad A, Iqbal N, Hatton RD, Weaver CT, Elson CO. (2005) Generation of antigen-specific, Foxp3-expressing CD4+ regulatory T cells by inhibition of APC proteosome function. J Immunol. 174(5): 2787-2795.

Cong Y, Weaver CT, Elson CO. (1997) The mucosal adjuvanticity of cholera toxin involves enhancement of costimulatory activity by selective up-regulation of B7.2 expression. J Immunol. 159(11): 5301-5308.

Cuadros C, Lopez-Hernandez FJ, Dominguez AL, McClelland M, Lustgarten J. (2004) Flagellin fusion proteins as adjuvants or vaccines induce specific immune responses. Infect Immun. 72(5): 2810-2816.

Crotty S, Aubert RD, Glidewell J, Ahmed R. (2004) Tracking human antigen-specific memory B cells: a sensitive and generalized ELISPOT system. J Immunol Methods. 286(1-2): 111-122.

Fontenot JD, Gavin MA, Rudensky AY. (2003) Foxp3 programs the development and function of CD4+CD25+ regulatory T cells. Nat Immunol. 4(4):330-36.

Hanauer SB. (2003) Genetics of IBD: Clinical Relevance. Medscape Gasteroenterology. (Available at http://cme.medscape.com/viewarticle/456992.).

Hori S, Nomura T, Sakaguchi S. (2003) Control of regulatory T cell development by the transcription factor Foxp3. Science. 299(5609): 1057-61.

Iqbal N, Oliver JR, Wagner FH, Lazenby AS, Elson CO, Weaver CT. (2002) T helper 1 and T helper 2 cells are pathogenic in an antigen-specific model of colitis. J Exp Med. 195(1): 71-84.

Kanauchi O, Mitsuyama K, Araki Y, Andoh A. (2003) Modification of intestinal flora in the treatment of inflammatory bowel disease. Curr Pharm Des. 9(4): 333-346.

(Continued)

*Primary Examiner*—Mark Navarro
(74) *Attorney, Agent, or Firm*—Ballard Spahr LLP

(57) ABSTRACT

Compositions and methods for the therapy and diagnosis of immune-mediated inflammatory diseases, including inflammatory bowel disease (IBD), Crohn's disease and ulcerative colitis, are disclosed. Illustrative compositions comprise one or more bacterial polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention or treatment of immune-mediated inflammatory disease.

6 Claims, 16 Drawing Sheets

OTHER PUBLICATIONS

Lodes MJ, Cong Y, Elson CO, Mohamath R, Landers CJ, Targan SR, Fort M, Hershberg RM. (2004) Bacterial Flagellin is a dominant antigen in Crohn disease. J Clin Invest. 113(9): 1296-306.

McSorley SJ, Ehst BD, Yu Y, Gewirtz AT. (2002) Bacterial Flagellin is an effective adjuvant for CD4+ T cells in vivo. J Immunol. 169(7): 3914-3919.

Rautava S, Isolauri E. (2002) The development of gut immune responses and gut microbiota: effects of probiotics in prevention and treatment of allergic disease. Curr Issues Intest Microbiol. 3(1): 15-22.

Robinson WH, DiGennaro C, Hueber W, Haab BB, Kamachi M, Dean EJ, Fournel S, Fong D, Genovese MC, de Vegvar HE, Skriner K, Hirschberg DL, Morris RI, Muller S, Pruijn GJ, van Venrooij WJ, Smolen JS, Brown PO, Steinman L, Utz PJ. (2002) Autoantigen microarrays for multiplex characterization of autoantibody responses. Nat Med. 8(3): 295-301.

Sakaguchi S. (2003) The origin of FOXP3-expressing CD4+ regulatory T cells: thymus or periphery. J Clin Invest. 112(9): 1310-12.

Skeiky YA, Lodes MJ, Guderian JA, Mohamath R, Bement T, Alderson MR, Reed SG. (1999) Cloning, expression, and immunological evaluation of two putative secreted serine protease antigens of Mycobacterium tuberculosis. Infect Immun. 67(8): 3998-4007.

Stoute JA, Slaoui M, Heppner DG, Momin P, Kester KE, Desmons P, Wellde BT, Garcon N, Krzych U, Marchand M. (1997) A preliminary evaluation of a recombinant circumsporozoite protein vaccine against Plasmodium falciparum malaria. N Engl J Med. 336(2): 86-91.

Tannock GW, Sartor RB, Walter J, Lerner A. (2005) Cloning the Gut Metagenome: A Strategy to Detect Pro-inflammatory Substances Produced by Intestinal Bacterial, Abstract presented at the $3^{rd}$ Annual BMRP Investigator Meeting (Feb. 24-25, 2005).

Targan SR, Landers CJ, Yang H, Lodes MJ, Cong Y, Papadakis KA, Vasiliauskas E, Elson CO, Hershberg RM. (2005) Antibodies to CBir1 flagellin define a unique response that is associated independently with complicated Crohn's disease. Gastroenterology. 128(7): 2020-2028.

The Food, GI-tract Functionality and Human Health Cluster—PROEUHEALTH. Workshop 4—Brussels, Belgium (Mar. 10-11, 2005).

Traggiai E, Becker S, Subbarao K, Kolesnikova L, Uematsu Y, Gismondo MR, Murphy BR, Rappuoli R, Lanzavecchia A. (2004) An efficient method to make human monoclonal antibodies from memory B cells: potent neutralization of SARS coronavirus. Nat Med. 10(8): 871-75.

Yoshimura S, Bondeson J, Foxwell BM, Brennan FM, Feldmann M, (2001) Effective antigen presentation by dendritic cells is NF-kappaB dependent: coordinate regulation of MHC, co-stimulatory molecules and cytokines. Int Immunol. 13(5): 675-683.

Zajac AJ, Blattman JN, Murali-Krishna K, Sourdive DJ, Suresh M, Altman JD, Ahmed R. (1998) Viral immune evasion due to persistence of activated T cells without effector function. J Exp Med. 188(12): 2205-2213.

International Search Report dated Aug. 8, 2008 for PCT/US2007/060996 (published as WO 2007/087576 on Aug. 2, 2007) naming Elson et al. as inventors and The UAB Research Foundation as the Applicant.

International Preliminary Report on Patentability including Written Opinion dated Sep. 9, 2008 for PCT/US2007/060996 (published as WO 2007/087576 on Aug. 2, 2007) naming Elson et al. as inventors and The UAB Research Foundation as the Applicant.

Cong Y, Hershberg RM, Landers CJ, Targan SR, Elson CO. (2004) Seroreactivity to a cluster of commensal flagellin in Crohn's disease Annual Meeting of the American Gastroenterological Association, May 14-19, 2005, in Chicago, IL.

Papadakis KA, Yang H, Ippoliti A, Elson CO, Hershberg RM, Vasiliauskas EA, Fleshner PR, Abreu MT, Taylor K, Rotter JI, Landers C, Targan SR. (2005) Anti-Flagellin (CBir1) Phenotypic and Genetic Chron's Disease Associations Annual Meeting of the American Gastroenterological Association, May 14-19, 2005, in Chicago, IL.

Dubinsky M, Mei L, Dutridge D, Picornell Y, Landers C, Farrior S, Wrobel I, Quios A, Christie D, Wahbeh G, Bahar R, Vasiliauskus E, Grill B, Silber G, Israel D, Kelts D, Shah P, Pietzak M, Dallazadeh S, Hershberg R, Elson C, Targan S, Taylor K, Rotter J, Yang HY. (2005) Annual Meeting of the American Gastroenterological Association, May 14-19, 2005, in Chicago, IL.

Cong Y, Lodes MJ, Hershberg RM, Elson CO. (2004) CBir1 flagellin is a dominant enteric bacterial antigen that activates pathogenic CD+4 Th1 cell responses in vivo. (2004) Annual Meeting of the American Gastroenterological Association, May 15-20, 2004, in New Orleans, LA.

Beckwith J, Cong Y, Sundberg JP, Elson CO, Leiter EH. (2004) A Colitis Susceptibility Gene Locus Regulates the CD4+ T Cell Immune Response to Bacterial Antigens. Annual Meeting of the American Gastroenterological Association, May 15-20, 2004, in New Orleans, LA.

* cited by examiner

CFSE-CD4⁺ T cells
No Treg cells

CFSE-CD4⁺ T cells
With Treg cells

CFSE-CD4⁺ T cells
With Treg cells and IL-2

CFSE

| Upper well | Lower well |
|---|---|
| Media | Naive T cells |

| | |
|---|---|
| Media | Naive T cells with Treg cells |

| | |
|---|---|
| Treg cells | Naive T cells |

CFSE

Adaptive transfer recipients of CFSE-labeled DO11.10 CD4+ T cells and unlabeled DO11.10 CD4+ T cells Adaptive transfer recipients of CFSE-labeled DO11.10 CD4+ T cells and unlabeled Treg cells Recipient Colonic cytokine production

| Cells transferred | Antigen | Colonic IL-12 (pg/ml) | | Colonic IFNγ (pg/ml) | |
|---|---|---|---|---|---|
| | | Exp1 | Exp2 | Exp1 | Exp2 |
| Th1 | TET-E.coli | <20 | <20 | <20 | <20 |
| Th1 | OVA-E.coli | 1306±247 | 628±84 | 273±50 | 473±69 |
| Th1+Treg | OVA-E.coli | 25±25 | <20 | <20 | <20 |
| Treg | OVA-E.coli | <20 | <20 | <20 | <20 |

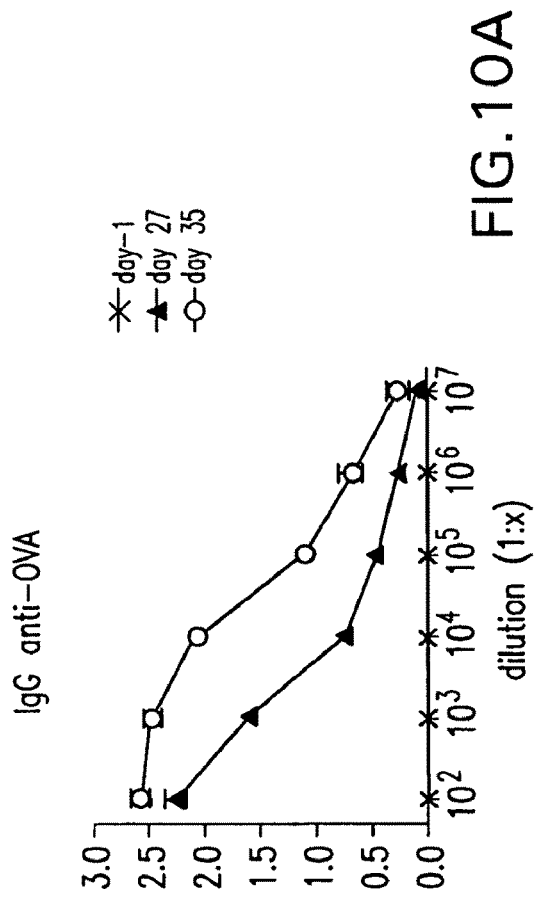
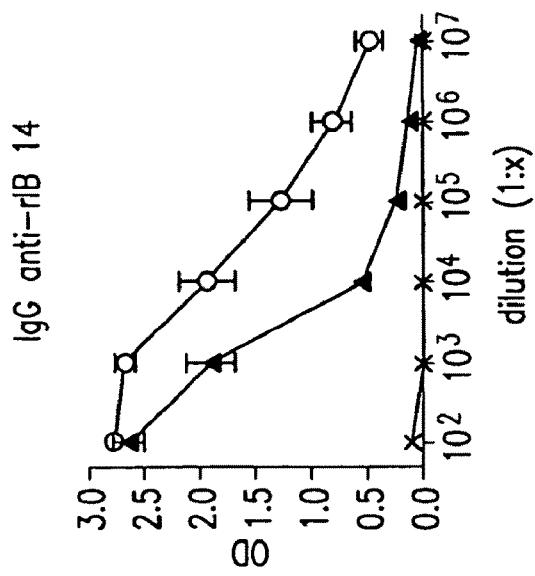
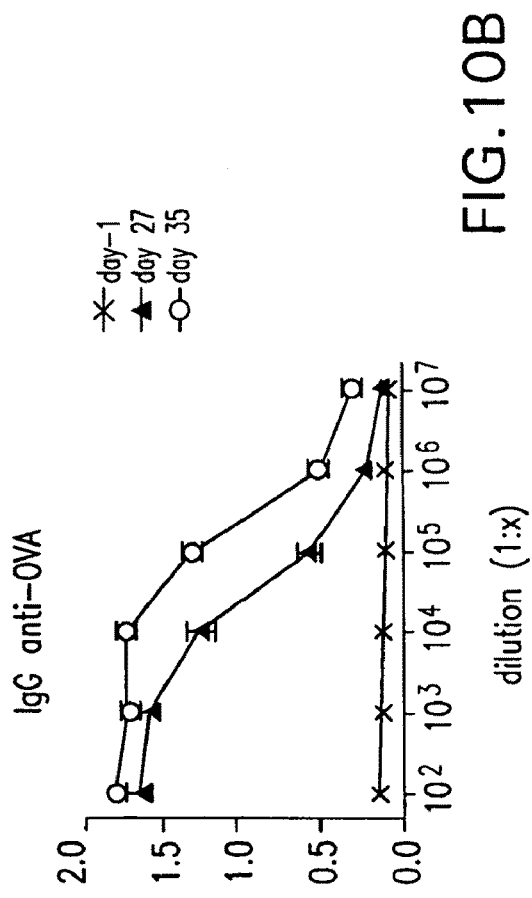
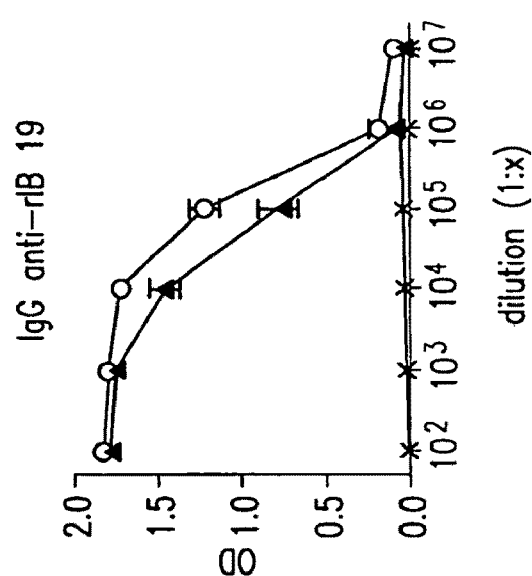
FIG. 10A
FIG. 10B

SEQUENCE LISTING

<160> NUMBER OF SEQ ID NOS: 83

<210> SEQ ID NO 1
<211> LENGTH: 686
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 461, 485, 504, 538, 541, 582, 613, 656, 658, 659, 681
<223> OTHER INFORMATION: n= a, t, c or g

<400> SEQUENCE: 1

```
gccggaggat tgtcagaact gaattttgaa aatgtggagc tgaccatgga atttcagccg      60
ttaaaggatt acaccgaaaa acggcaccga ccaggcccag tttctgattt ccaccaatgt     120
gggagaagaa ccgaagccgc ttcatatggt agcgtccggc ggcgagctgt ccagaattat     180
gctggcggtt aagacggtgc tggcggatga cgacgatatt cctacgttga tttttgatga     240
aattgacacc ggcatcagcg gcaggacggc ccagatggtt tctgaaaaat tgtcttatat     300
cggcagaaat catcaggtgc tgtgcattac ccatttgccc cagatcgctt tcatggcgga     360
```

```
cggacattac ctgatagaaa aatcttccag aaccggaaaa acaaaaaccc agattcacaa    420
gctggccccg aagaatccg  tatccgagct tgcccgtctt ntcggcggag ctcagattac    480
cgacncagtg ctggaaaatg ccanggagat gaaaaagctg gcggagcaga cgaaacangg    540
ntgaaagaac aaattaaata tttaccggcc cggacaggac angcagaagg aatgggacag    600
atcaaataaa atngtgaaaa taaaacaacc ggcctttgac agatcaccca aaaatntnna    660
ttgggaatca gaggaatcac ncccct                                         686

<210> SEQ ID NO 2
<211> LENGTH: 675
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: misc_feature
<222> LOCATION: 498, 502, 545, 576, 582, 596, 600, 601, 603, 623, 643,
      652, 662
<223> OTHER INFORMATION: n = a, t, c or g

<400> SEQUENCE: 2
atagaagaat gcaaaagact ggatgaggca gggatggact ataacttctt ctaccttgcc     60
gggatatacg gctccggaca tatggaggaa ggggtgaaga acacggcgga ggtgttcaac    120
cagctccacc cgaaggtcat agtttcctcc atgctgacgg tctatccgac ctcggagctg    180
taccaggaaa tccaggctgg gaactggacg gaggaaacgg aaatagaaaa gctgtatgaa    240
ttaaggacgc tggtcggcag ccttgacata gacacctatt ttgcaacgat gggcgcatcg    300
aactgcatca acgtggaagg gcatctgccg aaggacaggg gacggatggt caagtggctg    360
gatgaggtca tcggcgctgt ggacgaaaag gaactgcgca gataccgtga gaacctgcgg    420
catctgtagg agggaaagcc atgatacagg atatctcccc ttacaggctg gatatggcat    480
accacggtac agccccgncc cngatgactg cttttttcttc ttccgggaga ggatgtgctt    540
ttgcnggata tggggacgg gcataggacc tccctncttt cngatttgg ggcatncgcn     600 ngnaaaatgg aaacaaggcg gtnttcctgt tcccggcggg canggagccc cnttacctct    660
tnggcaggaa gtgtc                                                     675

<210> SEQ ID NO 3
<211> LENGTH: 659
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: misc_feature
<222> LOCATION: 49, 58, 86, 131, 153, 202, 224, 240, 262, 286, 308, 326,
      333, 439, 440, 480, 509, 537, 550, 573, 579, 599, 604
<223> OTHER INFORMATION: n = a, t, c or g

<400> SEQUENCE: 3
atgccgatcg ccagacagcg ctcctcgttc tgcacgcgca gccggtttnt ctcggttnca     60
tcatacacta acagggaaat aatttnccc  ttcccttcct ggtcgccttc ctcctgctcc    120
tccaccgcga nattctgcat ggaaagttca tancgcctgc gctttccttc atcgtccacg    180
gtcatctcca tgccgttgcc gnactcgttt aaaacctgca ccgncacctg tggaaaaaan    240
tcctgtatct gacagtggtt gnggaatccc atacctgtta tctcgnggaa cttatcattc    300
gcccacanaa taaagccgtc cctgtnaagc atngcatacg aaacctgcaa atcgagaagc    360
```

| atccggcgct gcacctggtt aaacggaaac caaaatcagt cagttggcgc ataatcttgc | 420 |
| ggttcttatg aaaaaagann gcaatcacaa tcaccaggta aaacgcagtg aaaatcatan | 480 |
| cgatatagag cacttttggc tctgctgcnt aaatacatac atccatggca agcatcngga | 540 |
| tgaataaatn aattggacca acgcatatta gcnttggaanc gtacgcagca ttttcatana | 600 |
| tttnattaca aattcattca ccacctcacg gggattccgc atgcgaagct cggttaccc | 659 |

```
<210> SEQ ID NO 4
<211> LENGTH: 661
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: misc_feature
<222> LOCATION: 621
<223> OTHER INFORMATION: n = a, t, c or g

<400> SEQUENCE: 4
```

| accccggagg aggccaaccg cctgggctgt gagctggcgc ggcgcttcac caagggcaat | 60 |
| catgctttta ttgtctgcac ccacatcgac aaagcacata ttcataacca catcatttgg | 120 |
| aactccacca ctctggactg cacccgaaaa ttccggact ttctcggttc cgggagggcg | 180 |
| gtacggcggc tgaacgatac catttgtatc gaaaacggat actctattgt ggccaatccc | 240 |
| aagcgccggg gcaagagcta caacaagtgg ctgggcagta agccgccctg ccaccgggac | 300 |
| cggcttcgca tggcgataga tgatgccctc gcaaaaaagc ccgctgacct ggacgcgctg | 360 |
| ctgaagctgc tgggagaagc aggcattgag gtatcgccac ggggaaaatt catccggcta | 420 |
| agagcaccgg gacagaaaaa tttcgtccgg ctggatgggg acagcttggg cgcggagtac | 480 |
| gatatttctg cgttgcttgg cccgtcctct ccggggagcg gacgcacacg cccaagcaca | 540 |
| aaaaaaggtc taccgcgcag atccgccgaa aggtcaatct ggttggtgga tattcaagcc | 600 |
| aaaactcccg gcccgggaaa nggtgcggga tattcgccgg gtggggccaa cgtggttcaa | 660 |
| c | 661 |

```
<210> SEQ ID NO 5
<211> LENGTH: 639
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: misc_feature
<222> LOCATION: 369, 513, 599, 632, 638
<223> OTHER INFORMATION: n = a, t, c or g

<400> SEQUENCE: 5
```

| gacctgaccc agcagccctg gtgccgagat gctctgctgc tccatgtccg cgggaccgga | 60 |
| gctttgcgct gggagacccg cgccttgccg ccgaaggcgg acctctacga aaccctctc | 120 |
| tgtctcaccc tccggggaac gcccctgctg tcctggttcg acgcagtgtg cgagacctgt | 180 |
| gaaagctggc tctgcaccgg ctggggcctg gacacagcgg aatgcccgga gctgacgct | 240 |
| ctgcggcaaa ccctcaatgg cggctttgcc gggctggagg acgctgttcc cgccctatcg | 300 |
| accctgctgg agctgctgcc ggagggcgta tatgtgctgg ctgagagcga cgcctatccc | 360 |
| acggacggnt gtgggcaatt cttctggaac gtgtctgact gcttggaacc taaccccgcc | 420 |

```
accggcgctg tttatctcaa cgatgatgat tacgactacc agtatgagcg gctgcctccg      480
gtatttctct atcctcccag cggcggtcac ggntggatat ggagcgggtg gagtattaca      540
aaaaccgctt ccagaaagac gggcctctcc ccacgggctt gccgtctatg ttaaggaang      600
gatgtccgtt ctgctggacg gacacacaaa cngctgcnc                            639
```

<210> SEQ ID NO 6
<211> LENGTH: 679
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 109, 132, 259, 260, 342, 367, 379, 421, 473, 500, 502, 528, 530, 546, 600, 611, 619, 622, 623, 626, 627, 632, 638, 641, 651, 655, 656, 658, 661, 663, 669, 672
<223> OTHER INFORMATION: n= a, t, c or g

<400> SEQUENCE: 6

```
aagaaggtgg cgcccggaa cgacaatgtc gtgacaaagc ataagttcac caaccggaac      60
cagcagcgcc ggggccagca gcgccggggc aagcgggaga cggaggccna gcgcttgcgc     120
cgcattgccc angagcgcaa ggcaaagcat atcaccattg aggtgccgga ggaaatcacg     180
gtgggcgagt ttgccctgcg cttaaaggtt tccgccccgg aggttatcaa aaagctgatg     240
ggcctggggg tgttcgccnn tatcaacgac gccatcgact ttgacaccgc ggtgttagtg     300
gcagacgaat tccacgccaa ggtggaaaaa gaagtggtgg tnaccattga ggagcgcatt     360
attgacnaca gcgaggacna agaggcaaac ctggcgcccc gcgcccctgt ggtggtggtt     420
ntgggccacg tggatcatgg caaaacctcc attctggacg ccatccgcca ctntaatgtg     480
acaatagggc gaggcatgcn gnattaccca gcacatcggc ccataccngn taaaagtggg     540
cgaccnggga cctaaccttt cttggacacc cccggccatg cttctttacc accatgcccn     600
caagggcgcc naggtgacng gnnttnnttg tncttgtngg ngcgggggac nactnntntt     660 ntncccana cngtggaag                                                  679
```

<210> SEQ ID NO 7
<211> LENGTH: 690
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 490, 572, 579, 581, 592, 599, 635, 638, 677, 680, 690
<223> OTHER INFORMATION: n= a, t, c or g

<400> SEQUENCE: 7

```
aagccctcca ccatggctgc catcatcgcc ctctctgacg agaaggttga ggaaatctgc      60
gaatgtgtag acggcgttgt cgtcgccgcc aactacaact gccccgggca gattgtgatt     120
tccggcgaaa tcgaggctgt caacgccgcc tgcgaggccg ccaaggccgc cggtgccaag     180
cgtgccctcc ccctgaaggt cggcggcgcg ttccactccc cgctgatgga gcccgcccgt     240
caggagctcg ccgaggccat cgccgccacc gagttccaca ccccgtatg ccccgtttac      300 cagaacgtcg atgccgctcc ccacaccgac cccgctgaaa tcaaggccaa cctcatcgcc     360
cagctgacag ccccgtgcg ctggaccag accgtggcaa acatggtggc cgacggcgct      420
accgagttcg tagagcttgg tccggcaag gtgctccagg gcctggtcaa caaggtgagc      480
```

| | |
|---|---|
| cgcgatgtan cggtttccgg caaagcagta acccccgacg caagggactg gccttaaaga | 540 |
| aacttaccat aacttttgcg ataaaaatcc cngacaagnc naaaattggc gnatgtccng | 600 |
| ggattttttta catcactctt gtggcggcag cgggnaangg ggccttaagg ggcttccggt | 660 |
| catttccccg attgtcnaan atgatccccn | 690 |

<210> SEQ ID NO 8
<211> LENGTH: 687
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 548, 552, 585, 594, 650, 651, 676, 683
<223> OTHER INFORMATION: n = a, t, c or g

<400> SEQUENCE: 8

| | |
|---|---|
| ggacataagc gcattccgtc gagagagggc ggcgtggaga tcgtcgtgga ggcccttgcg | 60 |
| gtcagaatgg cggaaaaagg tcataaagtg gaggcctata acaggtatgg acatcacgta | 120 |
| tccggtaaaa aatatgatga ggaatacgga cgcggtgaca gaaaatacta taaaggcgtc | 180 |
| cgcattcaca tcgtgccgac ctttaagagc agcaaactga acgccatcgt ttattccttc | 240 |
| tttgccaccg tccgggcgct cgtcaagcct tacgacgtga ttcactatca tgcggaagga | 300 |
| ccgtgcgcca tgctctggct gcccaggctg tgcgggaaaa gggtggttgc aacgatacac | 360 |
| ggtctggact ggcagcgggc caaatggggg aattttgctt cccgcgtgat tcggttcggc | 420 |
| gaaaaaatgg cggcaaaata tgcggatgaa gtcatcgttc tttcggaaaa tgtccgtcag | 480 |
| tattttaaag acacttacgg gcgggatgtg gttttttatcc ccaacggaat cgagcgcccc | 540 |
| accagacnga angcggaatt gattaccgga gaaattcgga ttacngggaa aacngctatt | 600 |
| tcctttttttc tggcaccgga ttgtaccccg aaaaaaggac ttgcattatn ntgatcgaag | 660 |
| catttcacaa aaaccntacc ggncaat | 687 |

<210> SEQ ID NO 9
<211> LENGTH: 689
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 565, 574, 608, 669, 675, 677
<223> OTHER INFORMATION: n = a, t, c or g

<400> SEQUENCE: 9

| | |
|---|---|
| ggggaaaaga tgcgcaatac gctccagact atacgggatg tttcaggaca gattgacagc | 60 |
| ggttcggagc agcttgcatg tgccgcccag gatctggctg agagctgtac ggtgcaggcc | 120 |
| ggacaggtat ctgaactgat gaccgcattc gggggcatga cccggagcat agaagaaaat | 180 |
| acccgggagg cggaggactc tgccagaatg gcttcggaag ctggtgtgac gcttgcaaag | 240 |
| gcaatgaga agatgcagga gcttaaggac tccattcagg agatgggaag atgctcagag | 300 |
| cagattggcg cgattattga agccatcgag gagattgcat cccagacaaa cctgctggcc | 360 |
| ctgaatgcag ccattgaggc ggcaagggcc ggagatgcag gaaaaggttt tgcggttgtg | 420 |
| gcggagcagg taaaaaatct tgcaaacgag tccgcaaagg ccgcgggaag aaccacagaa | 480 |

```
ctgattgaga ctaccgtttc agtaatggac aggagtattt ccattgcaga cgaaacggcg      540
gaaaatatga atcttggtaa tgacngacgc aaangcggct acagaaaaga tggaacagaa      600
ttgcgcanaa tgtttgaagg aaaacccatc accccatgcc ttgatttgaa tgaaaaattg      660
cccttccang gtttncnaat gcctgggggg                                      689
```

<210> SEQ ID NO 10
<211> LENGTH: 692
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 43, 45, 47, 48, 59, 60, 154, 248, 458, 471, 485, 518, 527, 576, 597, 619, 620, 625, 628, 643, 646, 655, 660, 662, 675
<223> OTHER INFORMATION: n = a, t, c or g

<400> SEQUENCE: 10

```
cgtgaggctc tgcatgagat tgtggaggat ttgaaacaga atncngnnac caatggtgnn      60
aaagggcgcg gttacacagg acagcgaact ggttctggta aattatggga aactggagga     120
aaagatggaa aatgcataac gaataggaac tgtnaaagca ccagagccgg aagtgacttt     180
taccgtggca gagtgtggag aatttcatac attggggaat tgttatgagg aataaagga     240 agcagacnag gcaatataaa tctggcagag agtgcagaaa agaatctga ataccgtgcc     300 gggacttggt atccatgtcc atataccggg acaggaagat tatatgaatg gcagattga     360 tttggtttcc ggaagaacga ttgatgtgag tattttggaa tatattccat ccatgaggaa     420
agagcctcgt gtcatggaaa aggtggcgga actgattnat cggctgcccg nttatgaaat     480
catangagat attcaaccgg aactgtcttt atggcttnat gtgcccngac cgcatggtaa     540
gagtatcttg atatgaaaag aatattgcta cctgtnggac aaggatgctt ccccatnggg     600
gaaaagaaaa aagcccctnn agttnttntc aaaaaagggg ttnttngtac aaaanttatn     660
tncccaatga ttccngagac ctttatgttc ac                                   692
```

<210> SEQ ID NO 11
<211> LENGTH: 660
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 63, 330, 523, 542, 612, 635, 639, 653, 659
<223> OTHER INFORMATION: n = a, t, c or g

<400> SEQUENCE: 11

```
cgggcggccg cctccctggg catccccgcc gccgtccacg agtccaacgc catcccaggc      60
ctnaccaccc gcctgctgga gaagcacgcg gacctcatca tggtgggctt cgaggagtgc     120
cggaaaaact accggcaccc ggaaaaggtt ctggtcaccg gcacgccggt gcggggagac     180
ttcttccggc tgacccggaa acaggcgaag cagaagctgg gcatggatga cggccggccc     240
ctcatcgtct ccttctgggg cagtctgggc gcccggagag tgaaccggca gatgcggaa      300 ttcctggccc tggaggcccg aaacggcatn cccttccacc acgtccacgg cgcgggcaag     360
gtggggtacc tccacatggc ggagtatctg aaggacgcgg gcattgatct ggaccgggcc     420
cccgggctgg aggtccggga gtacattcag gacatgggcg tcatgatgcg ggcccgccac     480
```

```
ctggtcatct gccgggcggg tgccagcacc atcaggcgaa ctnccgccct ggggtcccg    540 gncattatcg tccctcccca acgtgaccat aaccaccaag aattcaacgc cccgcgtttt    600
gccaacaggc gnggggccga gattatccca tgcancttng gtccccgggt cgncctgcnt    660
```

<210> SEQ ID NO 12
<211> LENGTH: 706
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 447, 496, 497, 561, 564, 565, 591, 641, 644, 650, 654, 688
<223> OTHER INFORMATION: n = a, t, c or g

<400> SEQUENCE: 12

```
aagctgggag agcctttgca ggtgaaggcc gtgctggtcc ggcattttaa ggacgggccc    60
taccgccagc tgatgacgga cgatttttaag aagattgagg aggacggcgg catccgggtg   120
gtggtggaga ccatcggcgg cgtggaggcg gcctatgagt acaccaagcg gtgcctctcc   180
gcggggaaac atgtggtcac cgccaacaag cagctggtgg cggaaaaggg ctgcgagctg   240
ctggccctgg cgaaaaagaa gaacgtcagc tacctttttg aggccagcgt gggcggcggc   300
attccggtgc tccaccctct gacccagtgc atggcggcca accgaataga cgaggtctac   360
ggtattttaa acggcaccac caattatatc ctcacccgta tggtccgcac cggggcctttt   420 ttctccgatg ccctccggga ggcccangcc aagggctacg cccgaggcgg accccaccgc   480
cgacgtggag ggcatnnacg cggggcggaa aatcttgcat tctgggggat ttggcctttc   540
ggcagcaaat ccgcatgcga nctnngtacc cccgggtcga cctgcaccaa ncttaattag   600
ctgagcttgg acttctgttt gatagatcca gtaatgacct naanaacttn catntggatt   660
tttttcaaaa acgcttcggt tgcccccngg cgttttttat tggtga                  706
```

<210> SEQ ID NO 13
<211> LENGTH: 687
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 569, 571, 623, 652, 657
<223> OTHER INFORMATION: n = a, t, c or g

<400> SEQUENCE: 13

```
aaatatggcg tgaagtagta agactgaaag agaaaaaacc ggcaatcgtt tctatgggag    60
attatgctgc atcaggaggc tattacattt cctgcgctgc aaaccgcatt ttcgctgacc   120
cgactacgct gactggttct atcggcatat tcggcatgat gtattcaggt gagaaactgt   180
ttactgaaac tttaggacta aattttgatg tagtgaaaac taataaaatg gctgatctgg   240
gtgccagcct aggtccggtt ctcacccgcc cgctaaatgc atcagaacaa gaattaatgc   300
agaactatgt caaccgagga tacaagttgt tcgtaaaccg ttgcgctgaa ggtagaaaaa   360
tgtctacaga ggctattgaa aaagttgctg aaggccgtgt atggaccggt gccatggcaa   420
aagaccttgg tctggtagac cagctgggag gtatagacaa agcattgaat gccgccgcca   480
cccaagccgg tatcgaaaat tacagtatta tcgcttcctg aaaaagaaaa tattttcgca   540
```

```
agcctgctgg gcaatcagaa aaaacattnt ntaaacagcg aaattaaaga atattttggg    600
aagctattat acagcttcaa ggngcttgga gaacataaaa gacgccactg tntacangcc    660
ctatgcccgt ttggacctta tattcaa                                       687
```

<210> SEQ ID NO 14
<211> LENGTH: 692
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: misc_feature
<222> LOCATION: 242, 424, 561, 574, 617, 650, 692
<223> OTHER INFORMATION: n = a, t, c or g
<400> SEQUENCE: 14

```
tatgccagag aagctgtttg aacggtattg tcaaaatagt gataaaatta gttggttcta     60
taaaaatgga gataagggta ttgaatattt ttccattgtt tatgaagaca atttcggaaa    120
gcagaaatca ttttatcctg actatgtagt aggtactgtg gacgggaaag tatggattat    180
agaaacgaag ggcggattta ccagagttgg tgatagcgaa gacatagaca aatataccgc    240
cnaaaagttt ttagtattga aaagtatct  tgctaaatat gaattacacg gtggtattgt    300
tcgacaagat aaacaaagca gcgagctttg catatgtact gatacatatt ccgatgacat    360
caaaagtgat agttggtgtc tactttctga tgttatgtga atcggagga tattacaatg     420 gctnatcagg acaacaaaaa gaatgtccca atctattttt attatcttac aatttccaag    480
caaaaagaca gtgccgatga gtccacatat aatatcaaac agattgttga accgttttc     540 taaactggtg ggatatactg ntggccaaga attnactaac ccgcagagta gatatcaaat    600
ctgctgaaaa aagttgnttg gctggatctt ttgctgattt aggtaatggn aactatgata    660 taattttttaa gtccgcaaat ataatcatgt tn                                 692
```

<210> SEQ ID NO 15
<211> LENGTH: 701
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: misc_feature
<222> LOCATION: 452, 459, 476, 505, 547, 560, 565, 607, 623, 641, 672,
      680, 690, 701
<223> OTHER INFORMATION: n = a, t, c or g
<400> SEQUENCE: 15

```
cgcttccact tcgccaaacg ggacgagacc ctgctggacg ccctgaatcg cctggagggg     60
ctgcgggaga aaataccggt gaaaggcggc gtgagagcgt gagtttgagc gttaatgagt    120
tgtcggatta tgttatttct ctgcggcggg agtttcaccg gcacccggag atatccatgg    180
aggaggagtg gacctgtgcg agaatctgcc aggagctgtc cgcccttgga atccctgtg     240 aaatcgtcgg cgataaaaat gtaattggcc gtctggaatt cggcgagggg cggcgcatat    300
ccttccgggc ggattttgac gcgctgccgg tgggagagac cctggacgta ccctggaaaa    360
gccaacaaga ggatgcgatg cacgcctgcg ggcacgacgg gcacaccgcg gcgctgctgg    420
gggcgggcag gcttctgcgg tcccccggag ancggctgng cggaccgtc tacctnttgc     480 tttcaacaag gccaggaggt gggganaagg ccccccggaat gcctggagta tctaaaacgg    540
```

```
agcggcngag tggatattgn catangcgcc catttttttc ccctttcgaa aaccgggacc    600
attgacnttt accccggttt tgngggccaa aggcccccgg nttttttcaca tttacattaa   660 ccggcaaaag gngggacacn ggttcccttn cccattccgc n                         701
```

<210> SEQ ID NO 16
<211> LENGTH: 625
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 229, 271, 488, 506, 551, 576, 588, 612, 625
<223> OTHER INFORMATION: n = a, t, c or g

<400> SEQUENCE: 16

```
ccgagaagcg cgccatcaag atggtgcccc aggagagcca ggccgagcag gcccaggtct    60
gggattacct ggtgaagact gctcccaagg ccgacatgca ggacaacacc gtcaagggca   120
gccagttcaa gcagccctac ctggagttct ccggctcctg cgccggctgc ccgagacca   180 gctacgcccg tctcgtcacc cagctgttcg gcgaccggat gtatatctnc aacgccaccg   240
gctgttcctc catctggggc ggtcccgctg ncaccagccc ctactgcgcc aacaaggagg   300
gcaagggccc cgcgtggtgc aactcccgt ttgaggacaa cgccgagcat ggcctgggca   360
tgtatatcgg ccagaaggcc atccgcagcg ccctggctga ggagaccaag cagctcatcg   420
ccgttgagtg ggcctatcag cccctgaagg acgccgctca aaagtggctg ataccatgg   480 aagacggnga ggccaaccag gcttgncgcc aaggagtaca ttgcccttgc tggaggagaa   540
gcctgatact nttggatgag aacgaaggcg tttatnaaca accccaaagg cgcgggaagt   600
tttcggcgac angcgcgacg ccatn                                          625
```

<210> SEQ ID NO 17
<211> LENGTH: 626
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 553, 561, 602
<223> OTHER INFORMATION: n = a, t, c or g

<400> SEQUENCE: 17

```
aggacgcgag agccggtcag ccacagtatt actataaatg gggcatcggc tccacgggtg    60
agctcggagc cgcaagtcag gacgagggaa actgccgtcc atgatgccta tacagccata   120
gagcaggctc cgcaatcgaa accggagcgt cctcagatta agacgaggga ggcccttata   180
agtggttctc ctgataggg cgccaccata cctcccgacc gcaaaccagg accatctgac   240
ccgttttcac tcaaaaccaa ggacgcctat atccaaagac agtccacagc acccccagag   300
cagccgcccc aggcgtttac ccaaggccag cagagattta taaaaagccg cagcgaggct   360
acgaccagga aacgggcgga ggttccgcgc acaggccgca gccccgttgt gcaggccaaa   420
ggcggcaggg aggctgttcc ttccgctccg gcacggcggg gctatgcggg aagtcaaaac   480
aggtatgttc cagtccaagc tgtacgccgg accgacaggt ccgggaacgc ccgatacccaa   540 acgtgtgcgg ganggcaaac ngccggtcat caaagtatcc cgttcccggc gaaaaaaaca   600
cngagcgcac cgccggcaaa cattat                                         626
```

<210> SEQ ID NO 18
<211> LENGTH: 624
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 576, 598, 623
<223> OTHER INFORMATION: n = a, t, c or g

<400> SEQUENCE: 18

```
atgaaccagc ccgaaaaccc ggacgcggct tcactggtta tcgccgtgcc gactgacgaa      60
caggtcagcg gcggcagctt caatccgtgg ggcccaaccg gaccaacgga atacaatgac     120
attacgctgg aagcaggcaa gctggaatat accggcacgg atggaaatga caactttatt     180
ggtgatttgt ccggaagttc aagcagatcc accttgcaac gtgacgatgt tatcgacggc     240
aacggtggag atgatatgtt gacggtttcc atggctcgta gctgggggg cttttcctca      300 aaaggcggga tggataatgt cgaaaccgtc aatctgaata cgttggcaa tggcagttat      360 acttttagcg ccagaggcat tgacggagcc gatacgttta atattgacgg caatatcggt     420
cttcttgacc tgtctgctgg cacaacagtc aacctcacaa acaccagcgc aaatacaaac     480
attgatttta ttcccagtga agtgaataac cttgacgatt catttactct tggcctgaat     540
aacgtgcgcc atgtccattc acggggcaat atttancttg taagagtaga tgcaagcngc     600
atcgagaatc tcatgcttaa tgnt                                            624
```

<210> SEQ ID NO 19
<211> LENGTH: 615
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 95, 357, 445, 453, 605
<223> OTHER INFORMATION: n = a, t, c or g

<400> SEQUENCE: 19

```
tgggtggacg aaatcaggtt ggtcggcacg cggaacttgc cgctgggctt gctcatgtcg      60
aaccggaagc tgacgatgga gggtttgcgg ctcanctgcc ggtggtagga gaggtagcgg     120
gtggggtcga tgcgccccga gacccactcc ttgaccacgc ccgacgagac gatggcccgc     180
atttcggccg gagaatagcc tgcggcgtac atgccgcga cgatggagcc catcgaggtt      240
cccgccacgc tttaagcagc tctgtccgca tgcgagctcg gtaccccggg tcgacctgca     300
gccaagctta attagctgag cttggactcc tgttgataga tccagtaatg acctcanaac     360
tccatctgga tttgttcaga acgctcggtt gccgccgggc gttttttatt ggtgagaatc     420
caagctagct tggcgagatt ttcangagct aangaagcta aaatggagaa aaaaatcact     480
ggatatacca ccgttgatat atcccaatgg catcgtaaag aacattttga ggcatttcag     540
tcagttgctc aatgtaccta taaccatacc gtcagctgga tattaccggc ttttaaaga      600 ccgtnaaaaa aaaat                                                      615
```

<210> SEQ ID NO 20
<211> LENGTH: 638
<212> TYPE: DNA

<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 340, 369, 431, 442, 454, 475, 502, 535, 536, 555, 557, 570, 583, 602, 603, 617, 633
<223> OTHER INFORMATION: n = a, t, c or g

<400> SEQUENCE: 20

```
ttcaagaggc gtggcggtca gggttgcctg accggggccg agtgtggtga agtcaccgtt      60
aaaaccgatg gataccacgt tgctgttgga ggagttgtac tccatcctgt cccccgggaa     120
atccgggaag aactgggaga caaggccgc gtagccataa ccggagcgga aaccgaactg     180
ggtcagctcc cgggtctcgg tctccctgga ataggcgacc gtcacctggc aggagatgtg     240
cgcctccatg agcacgggct ggggctgcat ggcggtgtac acctggaagg taaaggtggc     300
ggacagggtg gtgacgccgg gcttgtgggg cacgagccan aaggtatagg cgttcgcgta     360
ctgggcctnc gcgacatcgg ggtcgctgct ggtcatggaa acggacttga tgcgctggtc     420
ggagcccatc nagtaagcga anctgtggga ctcngagagc tccatctttt gggtnaagtc    480
ccggaaggga caggaccaat cnaaagagtt ctgtaccacc accctcagct catanncgct    540
ggcttggggt cattncnggt ttccaagccn gacaagaccg ctngtgcccg gcggaaaaaa    600
gnnggtatat ttaccntcc ggaattgatg tanaccct                             638
```

<210> SEQ ID NO 21
<211> LENGTH: 1446
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: misc_feature
<222> LOCATION: 3, 12, 582, 639, 643, 647, 670, 683, 685, 686, 687, 688, 689, 690, 691, 692, 693, 695, 697, 701, 739, 779
<223> OTHER INFORMATION: n = a, t, c or g

<400> SEQUENCE: 21

```
ganaagatga gnaaacagat tcgtggtctg acacagggct cacgaaatgc agaagatggt      60
atctcctgtg tgcagacagc agaaggcgca cttgcagagg tgcaggatat gctccagaga     120
atgaacgagc tggctgtaca ggcggcaaac ggtaccaatt ccgttacaga ccgtaaaatat    180
attcaggatg agattgacca gcttgtaacc gagattgaca gagtttctga gacgacaaag    240
ttcaatgaga catatctctt aaagggcgac gaggagttgc cggagaatct ggtacataca    300
tttaactatg tgaagggcga caagattgac cagcttggaa cttcctctgt cttaaatgcc    360
aagagcgaca gagtgatggt gaactacaat ggtgtggata cgtatatgt tgtgagcgcc     420
agcattagtt cagcaggttc aaaggagtct atgacagcag atgtaaagac aaagggatct    480
gatttcacaa aatatcttgc aagcggtgaa gttggaacga gttcttctgt cacaagcgtt    540
gcaatgagta cttcctatgc aatgtttaag aacacaaatc tnaacggcgt agcattgcag    600
aaaatggcaa atggtacagt ttatgcggat aaggatgcnt atntatncga tacagagacc    660
aagaatatcn ttcatatcaa gcncnnnnnn nnntntncct ntacgatgga taagcgctac    720
aggctgctgt acaatgtcna tccagaagtg actggctttg aggatacact gggtatgcnt    780
aagacagtag atctgctgac aaagaacgat ttcctcggtg cgacatcaga gaaccagctc    840
tataacaaag acggtgaggc aatcactggc atgggactct acaaatactt taatgagaac    900
```

-continued

```
ggggattata caggcggctt gtatgcagac aaggacgcaa ccaagaagat tattgagaac    960
gatacaacca gctcactgta ctatggaaaa tatatcacaa acctcaccga aaggtgaca    1020 gcggcactga cattctctgt tcatgcaggt gcagattctg acctgaataa cagaatctca    1080
gcgacaattg ataccatgtc agcagcagga cttggcgtga acaagttaaa gagcagctcg    1140
atcggtatcg tagatgagac aggtgacaat gcgagagagt cgattgacgt agttggagag    1200
gcattgaaga ttgtatccac ccagcgttca atcctcggtg cggttcagaa ccgtttggag    1260
cacacgattg caaacctcga taacgtagtt gagaatacaa cggctgcaga gtctgcaatc    1320
cgcgatacag atatggctga cgagatggtg aaattctcga caaccaggt gcttttacag     1380 gcaggccagt ccattcttgc acaggcaaac cagtcaaatc agggtgtact tcagctctta    1440
cagtaa                                                               1446
```

<210> SEQ ID NO 22
<211> LENGTH: 480
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: VARIANT
<222> LOCATION: 3, 193, 212, 214, 215, 223, 227, 228, 229, 230, 231, 232, 233, 246, 259
<223> OTHER INFORMATION: Xaa = any amino acid

<400> SEQUENCE: 22

```
Lys Met Xaa Lys Gln Ile Arg Gly Leu Thr Gln Gly Ser Arg Asn Ala
  1               5                  10                  15

Glu Asp Gly Ile Ser Cys Val Gln Thr Ala Glu Gly Ala Leu Ala Glu
             20                  25                  30

Val Gln Asp Met Leu Gln Arg Met Asn Glu Leu Ala Val Gln Ala Ala
         35                  40                  45

Asn Gly Thr Asn Ser Val Thr Asp Arg Lys Tyr Ile Gln Asp Glu Ile
     50                  55                  60

Asp Gln Leu Val Thr Glu Ile Asp Arg Val Ser Glu Thr Thr Lys Phe
 65                  70                  75                  80

Asn Glu Thr Tyr Leu Leu Lys Gly Asp Glu Leu Pro Glu Asn Leu
                 85                  90                  95

Val His Thr Phe Asn Tyr Val Lys Gly Asp Lys Ile Asp Gln Leu Gly
            100                 105                 110

Thr Ser Ser Val Leu Asn Ala Lys Ser Asp Arg Val Met Val Asn Tyr
        115                 120                 125

Asn Gly Val Asp Asn Val Tyr Val Ser Ala Ser Ile Ser Ser Ala
    130                 135                 140

Gly Ser Lys Glu Ser Met Thr Ala Asp Val Lys Thr Lys Gly Ser Asp
145                 150                 155                 160

Phe Thr Lys Tyr Leu Ala Ser Gly Glu Val Gly Thr Ser Ser Val
                165                 170                 175

Thr Ser Val Ala Met Ser Thr Ser Tyr Ala Met Phe Lys Asn Thr Asn
            180                 185                 190

Xaa Asn Gly Val Ala Leu Gln Lys Met Ala Asn Gly Thr Val Tyr Ala
        195                 200                 205

Asp Lys Asp Xaa Tyr Xaa Xaa Asp Thr Glu Thr Lys Asn Ile Xaa His
    210                 215                 220
```

```
Ile Lys Xaa Xaa Xaa Xaa Xaa Xaa Thr Met Asp Lys Arg Tyr Arg
225                 230                 235                 240

Leu Leu Tyr Asn Val Xaa Pro Glu Val Thr Gly Phe Glu Asp Thr Leu
            245                 250                 255

Gly Met Xaa Lys Thr Val Asp Leu Leu Thr Lys Asn Asp Phe Leu Gly
        260                 265                 270

Ala Thr Ser Glu Asn Gln Leu Tyr Asn Lys Asp Gly Glu Ala Ile Thr
    275                 280                 285

Gly Met Gly Leu Tyr Lys Tyr Phe Asn Glu Asn Gly Asp Tyr Thr Gly
290                 295                 300

Gly Leu Tyr Ala Asp Lys Asp Ala Thr Lys Lys Ile Ile Glu Asn Asp
305                 310                 315                 320

Thr Thr Ser Ser Leu Tyr Tyr Gly Lys Tyr Ile Thr Asn Leu Thr Glu
                325                 330                 335

Lys Val Thr Ala Ala Leu Thr Phe Ser Val His Ala Gly Ala Asp Ser
            340                 345                 350

Asp Leu Asn Asn Arg Ile Ser Ala Thr Ile Asp Thr Met Ser Ala Ala
        355                 360                 365

Gly Leu Gly Val Asn Lys Leu Lys Ser Ser Ile Gly Ile Val Asp
    370                 375                 380

Glu Thr Gly Asp Asn Ala Arg Glu Ser Ile Asp Val Val Gly Glu Ala
385                 390                 395                 400

Leu Lys Ile Val Ser Thr Gln Arg Ser Ile Leu Gly Ala Val Gln Asn
                405                 410                 415

Arg Leu Glu His Thr Ile Ala Asn Leu Asp Asn Val Val Glu Asn Thr
            420                 425                 430

Thr Ala Ala Glu Ser Ala Ile Arg Asp Thr Asp Met Ala Asp Glu Met
        435                 440                 445

Val Lys Phe Ser Asn Asn Gln Val Leu Leu Gln Ala Gly Gln Ser Ile
    450                 455                 460

Leu Ala Gln Ala Asn Gln Ser Asn Gln Gly Val Leu Gln Leu Leu Gln
465                 470                 475                 480

<210> SEQ ID NO 23
<211> LENGTH: 1431
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 23
caacaattac aaggaggtat tattatggta gtacagcaca atcttagagc aatgaattct      60
aacagaatgt taggcatcac acagggatct ttaaacaaat cgacagagaa gctctcatca     120
ggctacaagg taaacagggc agcagatgat gcagcgggtc tttcaatttc cgagaaaatg     180
agaaaacaga tcagaggact gtcacaggca tctttgaatg ctgaggatgg tatcagtgca     240
gtgcagaccg cagagggcgc attgacagaa gttcatgaca tgttgcagag aatgaacgag     300
ctggcagtaa aggctgcaaa cggcacaaac tctacatcag accgtcagac aattcaggac     360
gaggtagacc agctcctcac agaaatcgac cgtgtcgcag agaccaccaa attcaatgag     420
ctgtatacat tgaagggtga tgaggacaag gtgacaagat atctttcagc acatgacgca     480
ggtatagaag aaccttgac acagggcgca acaaacgcga cattttcaat ggaccagtta     540
aagtttggcg acaccatcat gatcgcgggc agagagtacc atatcagcgg aacacagaaa     600
```

-continued

```
cagcagggcg agattatcac atcatctgtt aagattggcc agcaggtaac gattgatgga    660
atcatgtaca cctgtacagc aactgtatcc aatgcagaca aatttgagct gacaaaggat    720
gatttgattg cgaagcttga cacatcaagc ctgagtatta tgtcagtgaa tggcaagacc    780
tactatggtg ctggcatcac agatgacagg actgttgtaa gctcaattgg tgcatacaag    840
ctgatacaga aggaactcgg actggcaagc agcattggtg cagacggctc aacacaggct    900
tcggtaaatg ccggagtaga tggcaagact ttgaagaagc cgagttttga gggcaaatgg    960
gtatttagta tcgacaaggg aagtgttcag gtacgcgagg acattgattt cagcctccat   1020
gtaggtgcag atgccgacat gaacaacaag attgcggtga gatcggagc gcttgacacg    1080 aagggtcttg gtatccaagg actgaatgta aaggatacga caggcgcagc agcgacctac   1140
gcgattgatt cgattgcgga cgcagtggca agaatttctg cgcagcgctc tttactcggt   1200
gcagtgcaga accggttaga gcacacgatc aacaacttgg ataacgttgt agagaacaca   1260
accgcagcag agagccagat ccgtgataca gatatggcaa cagagatggt gaagtactct   1320
aataacaacg tacttgcaca ggcaggccag tcaatgttag cacagtctaa tcaggcaaat   1380
cagggtgtac ttagtctctt aggctaatag aaaccgaaca atacagaaaa g            1431

<210> SEQ ID NO 24
<211> LENGTH: 460
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 24

Met Val Val Gln His Asn Leu Arg Ala Met Asn Ser Asn Arg Met Leu
 1               5                  10                  15

Gly Ile Thr Gln Gly Ser Leu Asn Lys Ser Thr Glu Lys Leu Ser Ser
            20                  25                  30

Gly Tyr Lys Val Asn Arg Ala Ala Asp Asp Ala Ala Gly Leu Ser Ile
        35                  40                  45

Ser Glu Lys Met Arg Lys Gln Ile Arg Gly Leu Ser Gln Ala Ser Leu
    50                  55                  60

Asn Ala Glu Asp Gly Ile Ser Ala Val Gln Thr Ala Glu Gly Ala Leu
65                  70                  75                  80

Thr Glu Val His Asp Met Leu Gln Arg Met Asn Glu Leu Ala Val Lys
                85                  90                  95

Ala Ala Asn Gly Thr Asn Ser Thr Ser Asp Arg Gln Thr Ile Gln Asp
            100                 105                 110

Glu Val Asp Gln Leu Leu Thr Glu Ile Asp Arg Val Ala Glu Thr Thr
        115                 120                 125

Lys Phe Asn Glu Leu Tyr Thr Leu Lys Gly Asp Glu Asp Lys Val Thr
    130                 135                 140

Arg Tyr Leu Ser Ala His Asp Ala Gly Ile Glu Gly Thr Leu Thr Gln
145                 150                 155                 160

Gly Ala Thr Asn Ala Thr Phe Ser Met Asp Gln Leu Lys Phe Gly Asp
                165                 170                 175

Thr Ile Met Ile Ala Gly Arg Glu Tyr His Ile Ser Gly Thr Gln Lys
            180                 185                 190

Gln Gln Gly Glu Ile Ile Thr Ser Ser Val Lys Ile Gly Gln Gln Val
        195                 200                 205

Thr Ile Asp Gly Ile Met Tyr Thr Cys Thr Ala Thr Val Ser Asn Ala
```

```
                210                 215                 220
Asp Lys Phe Glu Leu Thr Lys Asp Asp Leu Ile Ala Lys Leu Asp Thr
225                 230                 235                 240
Ser Ser Leu Ser Ile Met Ser Val Asn Gly Lys Thr Tyr Tyr Gly Ala
                245                 250                 255
Gly Ile Thr Asp Asp Arg Thr Val Val Ser Ile Gly Ala Tyr Lys
                260                 265                 270
Leu Ile Gln Lys Glu Leu Gly Leu Ala Ser Ser Ile Gly Ala Asp Gly
                275                 280                 285
Ser Thr Gln Ala Ser Val Asn Ala Gly Val Asp Gly Lys Thr Leu Lys
                290                 295                 300
Lys Pro Ser Phe Glu Gly Lys Trp Val Phe Ser Ile Asp Lys Gly Ser
305                 310                 315                 320
Val Gln Val Arg Glu Asp Ile Asp Phe Ser Leu His Val Gly Ala Asp
                325                 330                 335
Ala Asp Met Asn Asn Lys Ile Ala Val Lys Ile Gly Ala Leu Asp Thr
                340                 345                 350
Lys Gly Leu Gly Ile Gln Gly Leu Asn Val Lys Asp Thr Thr Gly Ala
                355                 360                 365
Ala Ala Thr Tyr Ala Ile Asp Ser Ile Ala Asp Ala Val Ala Arg Ile
                370                 375                 380
Ser Ala Gln Arg Ser Leu Leu Gly Ala Val Gln Asn Arg Leu Glu His
385                 390                 395                 400
Thr Ile Asn Asn Leu Asp Asn Val Val Glu Asn Thr Thr Ala Ala Glu
                405                 410                 415
Ser Gln Ile Arg Asp Thr Asp Met Ala Thr Glu Met Val Lys Tyr Ser
                420                 425                 430
Asn Asn Asn Val Leu Ala Gln Ala Gly Gln Ser Met Leu Ala Gln Ser
                435                 440                 445
Asn Gln Ala Asn Gln Gly Val Leu Ser Leu Leu Gly
                450                 455                 460

<210> SEQ ID NO 25
<211> LENGTH: 1503
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 25
caacaattac aaggaggtaa ttttatggta gtacagcaca atcttagagc aatgaacgca     60
aacagaatgt taggaatcac aaatagtgga ttatcgaagt cttcagagaa gctttcttca    120
ggatataaag ttaaccgtgc agcagacgac gcagcaggac tctctatttc agagaagatg    180
agaaagcaga tcagaggtct cacacaggct tctgtaaatg ctgaggatgg catcagtgca    240
gttcagacag cagaaggtgc tttgacagaa gtacatgata tgttacagag aatgaacgag    300
cttgcagtta aggcagcaaa cggaacaaat tccgtttcag accgtcagac aatacaggat    360
gaggttgacc agcttttaac tgaaattgat agagtagcag agacaaccaa gttcaacgaa    420
ctttacttgt taagggtca ggcagagaaa attgatgtat atttatctgc aaaagacgcc    480
ggtctcaagg gaacactcat gaatggtgca acatctgcaa catttatgat ggatgagtta    540
aagtttggcg acaagatcac aattgcaggc aaggtgtatt cgattggtat accggcagaa    600
gcaggcgttt cagcagcttc aattgcaatc gcaggcgcaa aagcaggcga gttgatcaca    660
```

-continued

```
attgacggtg tacagtatac agtgacagat ggcatcgaga acgaggataa gaatcttctg    720
agtatttcac atattcaggg aagaatctcc gttcagagca agattctgta taatggaaca    780
acatataatg tcatgaaaga cgaagatggc aatggtatcg ctgataccga tgcagcgatt    840
gtcacatctt ttagagcata tcagatgatt cagcgtgagc tggagctcgc aaatagtgta    900
ggtgcaaaca agagcagcgc aagcgttttg tcagtacaga tgaaagcgac tgcaaccgtt    960
gcatcaacga aagtgaacac gacgggcggc gcggctggtg cttcgcaggt gacaaccgtg   1020
acaaaagcgg tatttacgat tgcagtaaag ggtctttcag aagtcagaga agagttaaat   1080
ttcagccttc atgtaggtgc tgatgcagat atgacaaaca agattggtgt atctattgat   1140
gcgctggata ccaagggatt aggcatctat ggtctaaatg taaaggacga ttcaggatca   1200
gcagcgacat atgcaattga tgcaattgca gatgcagtag cacatgtttc tgcacagaga   1260
tcacttctcg gtgcagtcca gaacagatta gagcatacca ttaacaactt ggataacgtt   1320
gtagagaata cgacagcagc agagagcaca attcgtgata cggatatggc tacagagatg   1380
gttaagtttt caaattcaaa cattcttgca caggcaggcc agtcaatgct ggcacagtct   1440
aatcaggcaa atcagggtgt acttagctta ttgcagtagt cacagattcc gaaggagtga   1500
cag                                                                 1503
```

<210> SEQ ID NO 26
<211> LENGTH: 484
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 26

```
Met Val Val Gln His Asn Leu Arg Ala Met Asn Ala Asn Arg Met Leu
  1               5                  10                  15

Gly Ile Thr Asn Ser Gly Leu Ser Lys Ser Ser Glu Lys Leu Ser Ser
             20                  25                  30

Gly Tyr Lys Val Asn Arg Ala Ala Asp Asp Ala Ala Gly Leu Ser Ile
         35                  40                  45

Ser Glu Lys Met Arg Lys Gln Ile Arg Gly Leu Thr Gln Ala Ser Val
     50                  55                  60

Asn Ala Glu Asp Gly Ile Ser Ala Val Gln Thr Ala Glu Gly Ala Leu
 65                  70                  75                  80

Thr Glu Val His Asp Met Leu Gln Arg Met Asn Glu Leu Ala Val Lys
                 85                  90                  95

Ala Ala Asn Gly Thr Asn Ser Val Ser Asp Arg Gln Thr Ile Gln Asp
            100                 105                 110

Glu Val Asp Gln Leu Leu Thr Glu Ile Asp Arg Val Ala Glu Thr Thr
        115                 120                 125

Lys Phe Asn Glu Leu Tyr Leu Leu Lys Gly Gln Ala Glu Lys Ile Asp
    130                 135                 140

Val Tyr Leu Ser Ala Lys Asp Ala Gly Leu Lys Gly Thr Leu Met Asn
145                 150                 155                 160

Gly Ala Thr Ser Ala Thr Phe Met Met Asp Glu Leu Lys Phe Gly Asp
                165                 170                 175

Lys Ile Thr Ile Ala Gly Lys Val Tyr Ser Ile Gly Ile Pro Ala Glu
            180                 185                 190

Ala Gly Val Ser Ala Ala Ser Ile Ala Ile Ala Gly Ala Lys Ala Gly
```

```
                    195                 200                 205
Glu Leu Ile Thr Ile Asp Gly Val Gln Tyr Thr Val Thr Asp Gly Ile
    210                 215                 220

Glu Asn Glu Asp Lys Asn Leu Leu Ser Ile Ser His Ile Gln Gly Arg
225                 230                 235                 240

Ile Ser Val Gln Ser Lys Ile Leu Tyr Asn Gly Thr Thr Tyr Asn Val
                245                 250                 255

Met Lys Asp Glu Asp Gly Asn Gly Ile Ala Asp Thr Asp Ala Ala Ile
                260                 265                 270

Val Thr Ser Phe Arg Ala Tyr Gln Met Ile Gln Arg Glu Leu Glu Leu
            275                 280                 285

Ala Asn Ser Val Gly Ala Asn Lys Ser Ser Ala Ser Val Leu Ser Val
    290                 295                 300

Gln Met Lys Ala Thr Ala Thr Val Ala Ser Thr Lys Val Asn Thr Thr
305                 310                 315                 320

Gly Gly Ala Ala Gly Ala Ser Gln Val Thr Thr Val Thr Lys Ala Val
                325                 330                 335

Phe Thr Ile Ala Val Lys Gly Leu Ser Glu Val Arg Glu Glu Leu Asn
            340                 345                 350

Phe Ser Leu His Val Gly Ala Asp Ala Asp Met Thr Asn Lys Ile Gly
    355                 360                 365

Val Ser Ile Asp Ala Leu Asp Thr Lys Gly Leu Gly Ile Tyr Gly Leu
    370                 375                 380

Asn Val Lys Asp Asp Ser Gly Ser Ala Ala Thr Tyr Ala Ile Asp Ala
385                 390                 395                 400

Ile Ala Asp Ala Val Ala His Val Ser Ala Gln Arg Ser Leu Leu Gly
                405                 410                 415

Ala Val Gln Asn Arg Leu Glu His Thr Ile Asn Asn Leu Asp Asn Val
            420                 425                 430

Val Glu Asn Thr Thr Ala Ala Glu Ser Thr Ile Arg Asp Thr Asp Met
    435                 440                 445

Ala Thr Glu Met Val Lys Phe Ser Asn Ser Asn Ile Leu Ala Gln Ala
    450                 455                 460

Gly Gln Ser Met Leu Ala Gln Ser Asn Gln Ala Asn Gln Gly Val Leu
465                 470                 475                 480

Ser Leu Leu Gln

<210> SEQ ID NO 27
<211> LENGTH: 290
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 27
aatggtgcag cagctacata cgcaatcgac gcaattgcag acgcagtagc aaagatttct      60
gctcagcgtt cattactcgg tgcagtacag aacagattag accacacaat caacaacttg     120
gataacgttg tagagaacac aacagcagca gagagccaga ttcgtgatac agatatggct     180
acagggatgg tgaagtactc taataacaac gtacttgcac aggcaggtca gtcaatgctg     240
gctcagtcaa atcaggcaaa tcagggtgta cttagtctct taggttaatt              290

<210> SEQ ID NO 28
<211> LENGTH: 95
```

```
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 28

Asn Gly Ala Ala Ala Thr Tyr Ala Ile Asp Ala Ile Ala Asp Ala Val
 1               5                  10                  15

Ala Lys Ile Ser Ala Gln Arg Ser Leu Leu Gly Ala Val Gln Asn Arg
                20                  25                  30

Leu Asp His Thr Ile Asn Asn Leu Asp Asn Val Val Glu Asn Thr Thr
                35                  40                  45

Ala Ala Glu Ser Gln Ile Arg Asp Thr Asp Met Ala Thr Gly Met Val
        50                  55                  60

Lys Tyr Ser Asn Asn Asn Val Leu Ala Gln Ala Gly Gln Ser Met Leu
65                  70                  75                  80

Ala Gln Ser Asn Gln Ala Asn Gln Gly Val Leu Ser Leu Leu Gly
                85                  90                  95

<210> SEQ ID NO 29
<211> LENGTH: 1185
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: misc_feature
<222> LOCATION: 297, 319, 334, 342, 352, 357, 361, 372, 392, 400, 409,
      417, 423, 428, 431, 439, 441, 443, 445, 448, 451, 465, 471, 487,
      492, 495, 528, 546
<223> OTHER INFORMATION: n = a, t, c or g

<400> SEQUENCE: 29
tatctaacaa aaatatctta ttcatattaa gaagaaatac gattttatgt ttgaagatgg      60
tacttatcat ttcacataaa aaagaaaaac tgtcgcgcag gcagcagttt ttcttttttg     120
gctttgatag agaatattga tagagggttt tgatcaggaa agaatactg  ggcaatgaat     180 cgtctgaaaa gtgattgaat catatataat tttcgaaaaa cacaattata taaattttg      240 aaattttttt atttttcgca caataaagct aatatatttt caagatcctc cgatatntta    300
gtgtagcaga taaaggctnt aatatagaga catntctgac tntctataat cnaccgntcc    360
nacaattgga cntttacaag atgaacgagc tngcagaaan ggtgcaaang gcccaanttt    420
acntcagncc ntcagacant ncngnggngg ntgatcagct cctcncagaa ntcgaccgtg    480
tagcagngac anccnagttc aatgagacat ttttttaaag ggtgatgnag ataaggtagc    540
caaatntctc aacgcacatg atgcaggtat cgcaggaact tgacacagg  gcgctacaaa    600 cgctacattc tcaatgactc agttaaaatt tggtgataca atcaagattg caggcagaga    660
gtatcatatc agtggtacag cagctcagca gcagagcatt atcacaaatt ccgttaaggt    720
tggtcagcag gtaacaattg atggtatcat gtatacatgt tcttctgtat caaatgctga    780
taagtttgaa cttaccaagg cagatttggc agctaagatc aacactacaa gccagatcag    840
cgtaatggtt gcaaacggca agacctacta tggctcaggc attacaaatg acaagaatgt    900
tacgacaaca acaggcgctt atgctctggt tcagaaagaa ctcggactgg caagcagcat    960
cggtgcagat ggttctacac aggcatctgt atcagcaggt gtagcaggta caggtaattt    1020
tgcaggcaag caggtatttg cgattgacaa ggcgagcgta cagattcgcg aagcgatcga    1080
```

-continued

```
tttcagcctc catgtaggtg cagatgctga tatgaccaac aagatcgcag tgaagattga   1140
ctctcttgat acaagggac tcggaatcca aggtttgaac gtaaa                    1185
```

<210> SEQ ID NO 30
<211> LENGTH: 226
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: VARIANT
<222> LOCATION: 8, 14
<223> OTHER INFORMATION: Xaa = any amino acid

<400> SEQUENCE: 30

```
Asp Ile Phe Leu Lys Gly Asp Xaa Asp Lys Val Ala Lys Xaa Leu Asn
  1               5                  10                  15

Ala His Asp Ala Gly Ile Ala Gly Thr Leu Thr Gln Gly Ala Thr Asn
             20                  25                  30

Ala Thr Phe Ser Met Thr Gln Leu Lys Phe Gly Asp Thr Ile Lys Ile
         35                  40                  45

Ala Gly Arg Glu Tyr His Ile Ser Gly Thr Ala Ala Gln Gln Gln Ser
     50                  55                  60

Ile Ile Thr Asn Ser Val Lys Val Gly Gln Gln Val Thr Ile Asp Gly
 65                  70                  75                  80

Ile Met Tyr Thr Cys Ser Ser Val Ser Asn Ala Asp Lys Phe Glu Leu
                 85                  90                  95

Thr Lys Ala Asp Leu Ala Ala Lys Ile Asn Thr Thr Ser Gln Ile Ser
            100                 105                 110

Val Met Val Ala Asn Gly Lys Thr Tyr Tyr Gly Ser Gly Ile Thr Asn
        115                 120                 125

Asp Lys Asn Val Thr Thr Thr Gly Ala Tyr Ala Leu Val Gln Lys
    130                 135                 140

Glu Leu Gly Leu Ala Ser Ser Ile Gly Ala Asp Gly Ser Thr Gln Ala
145                 150                 155                 160

Ser Val Ser Ala Gly Val Ala Gly Thr Gly Asn Phe Ala Gly Lys Gln
                165                 170                 175

Val Phe Ala Ile Asp Lys Ala Ser Val Gln Ile Arg Glu Ala Ile Asp
            180                 185                 190

Phe Ser Leu His Val Gly Ala Asp Ala Asp Met Thr Asn Lys Ile Ala
        195                 200                 205

Val Lys Ile Asp Ser Leu Asp Thr Lys Gly Leu Gly Ile Gln Gly Leu
    210                 215                 220

Asn Val
225
```

<210> SEQ ID NO 31
<211> LENGTH: 1011
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 31

```
gagaagatga ggaagcagat cagaggactg aacaaagcat cctctaacgc acaggatggc    60
gtatcattga ttcagacagc agaaggcgcg ctgaatgaag ctcacagcat tcttcagaga   120
```

-continued

```
atgaatgaac tggcagtaca gggagcaaat gacaccaacc agaacgttga ccgtgacgca    180
atcaatcagg agttaagcgc actggtagaa gagcttgacc gtatttccgc aaccacacag    240
ttcaataaac agtctctgtt agatggcagc tttaccggaa agaaccttca ggtaggagca    300
aaccagaatc agaagattac catcaatatt gcagcaatga atgcagcagc aatcggaatc    360
aaacctaccc aggtaggagc aatgtccggt tatctgacaa ccaatgaagt tgtgaagaac    420
cagaaagtta aaaatgaagc tggtacctat acagctgctg atgcgaccac taaggcaagc    480
ggtacagctg gttctgcaaa gctgagagca tctattgcga accttgcagc atgtactaca    540
caggttggtg cactttattc tgcaggtaat acaaagacag catatttcaa aacaaacaat    600
ggaaccatta ccacattatc cggtctggta agagcatgtg cagcaaacct tgcagcatgt    660
gcagcacagg ttttcgcagt tgcaagcaag ccggctacag cagttagctc accgaacgta    720
agagattacc agcaggcaac cggaaccatt acaatggttc agaatgcaat caacaatgta    780
tccagccaga gatctgcact ggagcattta cagaacagac ttgagcatac aattgccaac    840
ctggataacg tagcagagaa tactcaggca gcagaacccc gtatccgtga tacagatatg    900
gcatctgaaa tggttgaata cagcaagaac aacattcttg cacaggcagg ccagtccatg    960
cttgcacagg ctaaccagtc taaccagggt gtacttcagc tcttacagta a            1011
```

<210> SEQ ID NO 32
<211> LENGTH: 336
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 32

Glu Lys Met Arg Lys Gln Ile Arg Gly Leu Asn Lys Ala Ser Ser Asn
1               5                   10                  15

Ala Gln Asp Gly Val Ser Leu Ile Gln Thr Ala Glu Gly Ala Leu Asn
            20                  25                  30

Glu Ala His Ser Ile Leu Gln Arg Met Asn Glu Leu Ala Val Gln Gly
        35                  40                  45

Ala Asn Asp Thr Asn Gln Asn Val Asp Arg Asp Ala Ile Asn Gln Glu
    50                  55                  60

Leu Ser Ala Leu Val Glu Glu Leu Asp Arg Ile Ser Ala Thr Thr Gln
65                  70                  75                  80

Phe Asn Lys Gln Ser Leu Leu Asp Gly Ser Phe Thr Gly Lys Asn Leu
                85                  90                  95

Gln Val Gly Ala Asn Gln Asn Gln Lys Ile Thr Ile Asn Ile Ala Ala
            100                 105                 110

Met Asn Ala Ala Ala Ile Gly Ile Lys Pro Thr Gln Val Gly Ala Met
        115                 120                 125

Ser Gly Tyr Leu Thr Thr Asn Glu Val Val Lys Asn Gln Lys Val Lys
    130                 135                 140

Asn Glu Ala Gly Thr Tyr Thr Ala Ala Asp Ala Thr Thr Lys Ala Ser
145                 150                 155                 160

Gly Thr Ala Gly Ser Ala Lys Leu Arg Ala Ser Ile Ala Asn Leu Ala
                165                 170                 175

Ala Cys Thr Thr Gln Val Gly Ala Leu Tyr Ser Ala Gly Asn Thr Lys
            180                 185                 190

Thr Ala Tyr Phe Lys Thr Asn Asn Gly Thr Ile Thr Thr Leu Ser Gly
        195                 200                 205
```

```
Leu Val Arg Ala Cys Ala Ala Asn Leu Ala Ala Cys Ala Ala Gln Val
    210                 215                 220

Phe Ala Val Ala Ser Lys Pro Ala Thr Ala Val Ser Ser Pro Asn Val
225                 230                 235                 240

Arg Asp Tyr Gln Gln Ala Thr Gly Thr Ile Thr Met Val Gln Asn Ala
                245                 250                 255

Ile Asn Asn Val Ser Ser Gln Arg Ser Ala Leu Gly Ala Leu Gln Asn
            260                 265                 270

Arg Leu Glu His Thr Ile Ala Asn Leu Asp Asn Val Ala Glu Asn Thr
        275                 280                 285

Gln Ala Ala Glu Pro Arg Ile Arg Asp Thr Asp Met Ala Ser Glu Met
    290                 295                 300

Val Glu Tyr Ser Lys Asn Asn Ile Leu Ala Gln Ala Gly Gln Ser Met
305                 310                 315                 320

Leu Ala Gln Ala Asn Gln Ser Asn Gln Gly Val Leu Gln Leu Leu Gln
                325                 330                 335

<210> SEQ ID NO 33
<211> LENGTH: 959
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 33
gagaagatga ggaagcagat cagaggactg aacaaagcat cctctaacgc acaggatggc      60
gtatcattga ttcagacagc agaaggcgcg ctgaatgaag ctcacagcat tcttcagaga     120
atgaatgaac tggcagtaca gggagcaaat gacaccaacc agaacgttga ccgtgacgca     180
atcaatcagg agttaagcgc actggtagaa gagcttgacc gtatttccga gaccacacag     240
ttcaataaac agtctctgtt agatggcagc tttaccggaa agaaccttca ggtaggagca     300
aaccagaatc agaagattac catcaatatt gcagcaatga atgcagcagc aatcggaatc     360
aaacctaccc aggtaggagc aatgtccggt tatctgacaa ccaatgaagt tgttaagaat     420
cagaaagttg gtacaaataa ttctgcagct ttaagaggat ctatcggggc tcttgcagca     480
tgtaccgtac aggttggagc aatttattct gctaattcaa aaggtgtggc atattataag     540
acccagaatg aacaattact acaaattctg gagatgtaag aacatgtgcc taagaatctg     600
gcaatgtgtg cagctcagat ctttaaagtt gcaagcaaac cggctacaac agttagcaca     660
ccgaacgtaa gagattatca gcaggcaacc ggaaccatta caatgattca gaatgcaatc     720
aacaatgtat ccagccagag atctgcactc ggagcattac agaacagact tgagcataca     780
attgccaacc tggataacgt ggcagagaat actcaggcag cagaatcccg tatccgtgat     840
acagatatgg catctgaaat ggttgaatac agcaagaata cattcttgc acaggcaggc     900 cagtccatgc ttgcacaggc taaccagtct aaccagggtg tacttcgctc ttacagtaa     959

<210> SEQ ID NO 34
<211> LENGTH: 319
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 34
```

```
Glu Lys Met Arg Lys Gln Ile Arg Gly Leu Asn Lys Ala Ser Ser Asn
 1               5                  10                  15

Ala Gln Asp Gly Val Ser Leu Ile Gln Thr Ala Glu Gly Ala Leu Asn
            20                  25                  30

Glu Ala His Ser Ile Leu Gln Arg Met Asn Glu Leu Ala Val Gln Gly
        35                  40                  45

Ala Asn Asp Thr Asn Gln Asn Val Asp Arg Asp Ala Ile Asn Gln Glu
    50                  55                  60

Leu Ser Ala Leu Val Glu Glu Leu Asp Arg Ile Ser Glu Thr Thr Gln
65                  70                  75                  80

Phe Asn Lys Gln Ser Leu Leu Asp Gly Ser Phe Thr Gly Lys Asn Leu
                85                  90                  95

Gln Val Gly Ala Asn Gln Asn Gln Lys Ile Thr Ile Asn Ile Ala Ala
            100                 105                 110

Met Asn Ala Ala Ala Ile Gly Ile Lys Pro Thr Gln Val Gly Ala Met
        115                 120                 125

Ser Gly Tyr Leu Thr Thr Asn Glu Val Val Lys Asn Gln Lys Val Gly
    130                 135                 140

Thr Asn Asn Ser Ala Ala Leu Arg Gly Ser Ile Gly Ala Leu Ala Ala
145                 150                 155                 160

Cys Thr Val Gln Val Gly Ala Ile Tyr Ser Ala Asn Ser Lys Gly Val
                165                 170                 175

Ala Tyr Tyr Lys Thr Gln Asn Gly Thr Ile Thr Thr Asn Ser Gly Asp
            180                 185                 190

Val Arg Thr Cys Ala Lys Asn Leu Ala Met Cys Ala Ala Gln Ile Phe
        195                 200                 205

Lys Val Ala Ser Lys Pro Ala Thr Thr Val Ser Thr Pro Asn Val Arg
    210                 215                 220

Asp Tyr Gln Gln Ala Thr Gly Thr Ile Thr Met Ile Gln Asn Ala Ile
225                 230                 235                 240

Asn Asn Val Ser Ser Gln Arg Ser Ala Leu Gly Ala Leu Gln Asn Arg
                245                 250                 255

Leu Glu His Thr Ile Ala Asn Leu Asp Asn Val Ala Glu Asn Thr Gln
            260                 265                 270

Ala Ala Glu Ser Arg Ile Arg Asp Thr Asp Met Ala Ser Glu Met Val
        275                 280                 285

Glu Tyr Ser Lys Asn Asn Ile Leu Ala Gln Ala Gly Gln Ser Met Leu
    290                 295                 300

Ala Gln Ala Asn Gln Ser Asn Gln Gly Val Leu Arg Ser Tyr Ser
305                 310                 315
```

<210> SEQ ID NO 35
<211> LENGTH: 1679
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: misc_feature
<222> LOCATION: 725, 736, 779, 790, 800, 812
<223> OTHER INFORMATION: n= a, t, c or g

<400> SEQUENCE: 35

```
gaccgccgag ggtgcactga cagaagtaca ttccatgctg cagcgtatga atgaactggc    60
tacccaggct tccaacggaa ccaattcaga atctgaccgg gatgcaattc aggcggaaat   120
```

-continued

```
caaccagctg accacagaaa ttgaccgtgt ggctgagaca accaaattca atgagattta    180
tctgctgaaa ggcaaccgtg ccggtgcagt gactacccag aaagtagcag cccatgacgc    240
aggccttaag ggaacactca ctgatttggg cggcggaaca tccactttca cgctggataa    300
agctctggaa aacggagata aggttaccat tgccggacag gaatatacca ttggtacctc    360
agaaaaccat aaagaagccg agaactgaa tacttctacg gacgggtatg taaaatctga     420
cgctgttcca tttgtcacaa ctaccctgaa tgcaggagac agcgtaacct atcagggaaa    480
tacctatact ttaaccgata aaattgcggc tgatgacctg aaatggaaag caggcgataa    540
agtaaaggtt ggagatgcgg aatttacagt agctgccggc agcggtgccc ctgatgaagc    600
ggcaggaact gttggtgtgg atgtagttgc aaaatttgtg aatctgctc tggcagacgg     660
aaaagcaggt gtgggaacca atgtgaccgt atctgaaaca aaagcgggtg ctactgataa    720
ttcanatgtg acgaangcgg gaaactttac catagtttct gctctggaag caggaaaant    780
cagctctgcn aaagtggtan acaaaacagc gncaaccatc gccaagcagg ggcaggactt    840
acccagtagc cgcagcattc agtacagggg acagcgttac cattggaggc gttaccacga    900
cagccacagc ggaaactcca attgccgcaa agatgtata cgatgcagtc aacggactgg     960
ctgtgggagg tacagtagta attggaagcg gtacagatca gattacctat acaatcgttg   1020
atgaagcgga tgtggatgaa gaagccttta aacttacaaa agatgcgatt ctggcaagaa   1080
ttcatgatgg tgacagtgtc agcacagacg gaggaacaac caccaatacc gttatcggtg   1140
acattgccct gccaaagagc gatgaaaaag taatcagcgc caaagaggct tattccatga   1200
tggcagaaga actgcagaag gcttccagta ttggagccga cgaggcagct gccgtaacaa   1260
atgatgcgaa tggaaaattc accattacac agggttctgt ggaagtgaaa aaatccctgt   1320
ccttcaatct ccatgtaggt tctgacgccg atatgaccaa taagattacc gttgatatcg   1380
acgccatgga cgcagcagga ctgggtgtaa agaatctgaa tgtatccgat gaaaccggaa   1440
cagccgcaac ctatgcaatc gacgccattg cagacgcaat ttccaaagta tccgcacagc   1500
gttctgctct cggtgcagtt cagaacagac tggagcacac cattgccaac ctggataacg   1560
ttgtggaaaa taccacagca gcagaatcca gaatccgcga tacggatatg gcatccgaga   1620
tggtggaata cagcaagaac aatattcttg cacaggcagg ccaatcaatg ttggcacag   1679
```

<210> SEQ ID NO 36
<211> LENGTH: 339
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 242, 245, 260, 263, 267, 271
<223> OTHER INFORMATION: Xaa = any amino acid

<400> SEQUENCE: 36

Thr Ala Glu Gly Ala Leu Thr Glu Val His Ser Met Leu Gln Arg Met
1               5                   10                  15

Asn Glu Leu Ala Thr Gln Ala Ser Asn Gly Thr Asn Ser Glu Ser Asp
            20                  25                  30

Arg Asp Ala Ile Gln Ala Glu Ile Asn Gln Leu Thr Thr Glu Ile Asp
        35                  40                  45

Arg Val Ala Glu Thr Thr Lys Phe Asn Glu Ile Tyr Leu Leu Lys Gly
    50                  55                  60

Asn Arg Ala Gly Ala Val Thr Thr Gln Lys Val Ala Ala His Asp Ala
 65                  70                  75                  80

Gly Leu Lys Gly Thr Leu Thr Asp Leu Gly Gly Thr Ser Thr Phe
             85                  90                  95

Thr Leu Asp Lys Ala Leu Glu Asn Gly Asp Lys Val Thr Ile Ala Gly
             100                 105                 110

Gln Glu Tyr Thr Ile Gly Thr Ser Glu Asn His Lys Glu Ala Gly Glu
         115                 120                 125

Leu Asn Thr Ser Thr Asp Gly Tyr Val Lys Ser Asp Ala Val Pro Phe
130                 135                 140

Val Thr Thr Thr Leu Asn Ala Gly Asp Ser Val Thr Tyr Gln Gly Asn
145                 150                 155                 160

Thr Tyr Thr Leu Thr Asp Lys Ile Ala Ala Asp Asp Leu Lys Trp Lys
                165                 170                 175

Ala Gly Asp Lys Val Lys Val Gly Asp Ala Glu Phe Thr Val Ala Ala
            180                 185                 190

Gly Ser Gly Ala Pro Asp Glu Ala Gly Thr Val Gly Val Asp Val
        195                 200                 205

Val Ala Lys Phe Val Glu Ser Ala Leu Ala Asp Gly Lys Gln Val Val
        210                 215                 220

Gly Thr Asn Val Thr Val Ser Glu Thr Lys Ala Gly Ala Thr Asp Asn
225                 230                 235                 240

Ser Val Thr Xaa Ala Gly Asn Phe Thr Ile Val Ser Ala Leu Glu
        Xaa
            245                 250                 255

Ala Gly Lys Xaa Ser Ser Xaa Lys Val Val Xaa Lys Thr Ala Xaa Thr
            260                 265                 270

Ile Ala Lys Gln Gly Gln Asp Leu Pro Ser Ser Arg Ser Ile Gln Tyr
            275                 280                 285

Arg Gly Gln Arg Tyr His Trp Arg Arg Tyr His Asp Ser His Ser Gly
        290                 295                 300

Asn Ser Asn Cys Arg Lys Arg Cys Ile Arg Cys Ser Gln Arg Thr Gly
305                 310                 315                 320

Cys Gly Arg Tyr Ser Ser Asn Trp Lys Arg Tyr Arg Ser Asp Tyr Leu
            325                 330                 335

Tyr Asn Arg

<210> SEQ ID NO 37
<211> LENGTH: 1289
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: misc_feature
<222> LOCATION: 636, 680
<223> OTHER INFORMATION: n = a, t, c or g

<400> SEQUENCE: 37
cagacagctg aggcgctctg acagaagtgc attccatgct gcagcgtatg aatgagctgg      60
caacccaggc agccaatgga accaattctg aatctgaccg agatgcaatc caggcagaaa     120
ttgaccagtt gaccacagaa attgaccgtg tggcagagac taccaagttc aatgaaattt     180
atctgctcaa aggcgataag ggcggagtta ccacaaccca gactattcca gcgcatgatg     240
caggaatcaa tggaaaactt accgacaaag gcggcgggt gtcaagtttt gaactggata     300
agcctttgga aaatggtgat aagattacca tcggtggaaa agaatatacc atcggaacat     360

```
cagcggacca taaagatccc acagagctga atacagatac cacaggatat ccagtggcag      420
gggcatctcc ctttactaca gatgctgtgg cagtaggaga cagtgtaaca tatcaaggaa      480
atacttatac cttaaccgat aaggtggcca ttgatgatat tacatggacg gctgctgata      540
aagtaaaaat cggagagatt gaatttaccc ttggcgcggc aggcagcgct acaaccatta      600
atgaagctgc taaaacaggt acagttgctg tggatnagga tgtagatgaa gaagctttta      660
agctcacaaa ggaagccatn ttagctaaaa ttcatgatgg agataaagtg agtccagatg      720
gcggcactac cttttatact gttatcggag acatcgctct tccagaaagc aatgaaaagg      780
taattagcgc aaaacaggca tatgctatga ttgcagatga attacagcag gcttccagta      840
ttggaacgga tgttgcagct acggtaacca atgatggaga aggcaaatat accatcacac      900
agggtactgt ggaggtgaaa gaggcgttat ccttcaatct tcatgtaggt tccgatgcag      960
acatgaccaa caagattacc gttgatattg acgctatgga tgcagccggc cttggcgtga     1020
agaacctgaa tgtatcagat gacagcggaa atgctgcaac ttatgctatt gatgcaattg     1080
cagatgcaat ttccaaagta tctgcacagc gttctgccct tggtcagtt cagaacagat      1140 tagagcacac cattgctaac ctggataacg ttgtagaaaa taccactgca gcagaatctc     1200
gtattcgcga tactgatatg gcttctgaga tggtggaata cagcaagaac aatattcttg     1260
cccaggctgg tcagtcaatg ctcgcacag                                        1289
```

<210> SEQ ID NO 38
<211> LENGTH: 384
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: VARIANT
<222> LOCATION: 209
<223> OTHER INFORMATION: Xaa = any amino acid

<400> SEQUENCE: 38

```
Gly Ala Leu Thr Glu Val His Ser Met Leu Gln Arg Met Asn Glu Leu
  1               5                  10                  15

Ala Thr Gln Ala Ala Asn Gly Thr Asn Ser Glu Ser Asp Arg Asp Ala
             20                  25                  30

Ile Gln Ala Glu Ile Asp Gln Leu Thr Thr Glu Ile Asp Arg Val Ala
         35                  40                  45

Glu Thr Thr Lys Phe Asn Glu Ile Tyr Leu Leu Lys Gly Asp Lys Gly
     50                  55                  60

Gly Val Thr Thr Thr Gln Thr Ile Pro Ala His Asp Ala Gly Ile Asn
 65                  70                  75                  80

Gly Lys Leu Thr Asp Lys Gly Gly Val Ser Ser Phe Glu Leu Asp
                 85                  90                  95

Lys Pro Leu Glu Asn Gly Asp Lys Ile Thr Ile Gly Gly Lys Glu Tyr
            100                 105                 110

Thr Ile Gly Thr Ser Ala Asp His Lys Asp Pro Thr Glu Leu Asn Thr
        115                 120                 125

Asp Thr Thr Gly Tyr Pro Val Ala Gly Ala Ser Pro Phe Thr Thr Asp
    130                 135                 140

Ala Val Ala Val Gly Asp Ser Val Thr Tyr Gln Gly Asn Thr Tyr Thr
145                 150                 155                 160

Leu Thr Asp Lys Val Ala Ile Asp Asp Ile Thr Trp Thr Ala Ala Asp
```

|  | 165 |  |  |  | 170 |  |  |  | 175 |  |  |
|---|---|---|---|---|---|---|---|---|---|---|---|
| Lys | Val | Lys | Ile | Gly | Glu | Ile | Glu | Phe | Thr | Leu | Gly | Ala | Ala | Gly | Ser |
|  |  |  | 180 |  |  |  |  | 185 |  |  |  |  | 190 |  |  |
| Ala | Thr | Thr | Ile | Asn | Glu | Ala | Ala | Lys | Thr | Gly | Thr | Val | Ala | Val | Asp |
|  |  |  | 195 |  |  |  |  | 200 |  |  |  |  | 205 |  |  |
| Xaa | Asp | Ser | Asn | Glu | Lys | Val | Ile | Ser | Ala | Lys | Gln | Ala | Tyr | Ala | Met |
|  |  |  | 210 |  |  |  |  | 215 |  |  |  |  | 220 |  |  |
| Ile | Ala | Asp | Glu | Leu | Gln | Gln | Ala | Ser | Ser | Ile | Gly | Thr | Asp | Val | Ala |
| 225 |  |  |  |  | 230 |  |  |  |  | 235 |  |  |  |  | 240 |
| Ala | Thr | Val | Thr | Asn | Asp | Gly | Glu | Gly | Lys | Tyr | Thr | Ile | Thr | Gln | Gly |
|  |  |  |  | 245 |  |  |  |  | 250 |  |  |  |  | 255 |  |
| Thr | Val | Glu | Val | Lys | Glu | Ala | Leu | Ser | Phe | Asn | Leu | His | Val | Gly | Ser |
|  |  |  | 260 |  |  |  |  | 265 |  |  |  |  | 270 |  |  |
| Asp | Ala | Asp | Met | Thr | Asn | Lys | Ile | Thr | Val | Asp | Ile | Asp | Ala | Met | Asp |
|  |  |  | 275 |  |  |  |  | 280 |  |  |  |  | 285 |  |  |
| Ala | Ala | Gly | Leu | Gly | Val | Lys | Asn | Leu | Asn | Val | Ser | Asp | Asp | Ser | Gly |
|  |  | 290 |  |  |  |  | 295 |  |  |  |  | 300 |  |  |  |
| Asn | Ala | Ala | Thr | Tyr | Ala | Ile | Asp | Ala | Ile | Ala | Asp | Ala | Ile | Ser | Lys |
| 305 |  |  |  |  | 310 |  |  |  |  | 315 |  |  |  |  | 320 |
| Val | Ser | Ala | Gln | Arg | Ser | Ala | Leu | Gly | Ala | Val | Gln | Asn | Arg | Leu | Glu |
|  |  |  |  | 325 |  |  |  |  | 330 |  |  |  |  | 335 |  |
| His | Thr | Ile | Ala | Asn | Leu | Asp | Asn | Val | Val | Glu | Asn | Thr | Thr | Ala | Ala |
|  |  |  | 340 |  |  |  |  | 345 |  |  |  |  | 350 |  |  |
| Glu | Ser | Arg | Ile | Arg | Asp | Thr | Asp | Met | Ala | Ser | Glu | Met | Val | Glu | Tyr |
|  |  |  | 355 |  |  |  |  | 360 |  |  |  |  | 365 |  |  |
| Ser | Lys | Asn | Asn | Ile | Leu | Ala | Gln | Ala | Gly | Gln | Ser | Met | Leu | Ala | Gln |
|  |  | 370 |  |  |  |  | 375 |  |  |  |  | 380 |  |  |  |

<210> SEQ ID NO 39
<211> LENGTH: 1284
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 39

```
gagaagatga gaaagcaaat caagggtctt gacagagctt caacaaatgc agaggatggc      60
gtttcagcag tacagacagc agaaggtgcc ctcacagagg ttcactcaat gctccagcgt     120
atgaacgagc ttgcaacaca gtctgcaaac ggaacaaact ctaacacaga tcgtaaagca     180
atccaggacg agatagacca gcttacaaca gagattgacc gtgtatcaga gacaacaaag     240
ttcaatgaga cctacctctt aaagggtgac ggatcagaga aggctcataa tgtaaatgca     300
catgatgctg gacttgatgg agttacactc acagataagg gtaatacagt tgatgttaca     360
ttaaagacac tcaatgctgg tgataagata agtattgctg gtaagaacta tacaattggt     420
tctaaagctg cggatatagc ggctaaaata gaggctggaa ctgatactgc aaagaagtca     480
tacacagtta atggaactac atatcaggta ggcactacaa atgtgtttga ttcagctgga     540
aataagataa agaaatctga cttaacggga atgctggtg atacaggtga tgctgtactt     600
aaagatttac aggatttggt taagatggt tcaacagtaa ctattggaac aaaaacatac     660
acagccatga cagataaaga tggtggtgcc gatggtattg atgacaatga ctcaactgtt     720
atcactgatg gaaagcata tcagttacag acagctgaaa tcgtaaagc aagcagtatt     780
ggagctgata cagctgctac aaatgcaaca aatgctaacg atgcatatga tactgcaacc     840
```

```
acaacattca ccctaaacaa aggaaatgtt tcatacaaag atggcttaag cttcaacctc    900
cacgtaggag cagatgctga catgacaaac aagattgcag tcaacatcga ctcaatgaac    960
tctgcaggtc ttggaatcaa aggtatcaag gctgatacag agcaggatgc tacatatgca   1020
atcgacgcaa tgcagatgc tatttcaaca gtatcttcac agcgttcagc acttggtgct   1080
gttcagaacc gtcttgagca cacaatcaac aaccttgaca acgtagttga gaatactaca   1140
tcagctgagt ctcgtatccg tgatacagat atggctgaag agatggttaa ctacagcaag   1200
aacaacattc ttgcacaggc tggacagtct atgcttgcac aggctaatca gtcaaaccag   1260
ggtgtacttc agctcttaca gtaa                                         1284
```

<210> SEQ ID NO 40
<211> LENGTH: 427
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 40

```
Glu Lys Met Arg Lys Gln Ile Lys Gly Leu Asp Arg Ala Ser Thr Asn
  1               5                  10                  15

Ala Glu Asp Gly Val Ser Ala Val Gln Thr Ala Glu Gly Ala Leu Thr
             20                  25                  30

Glu Val His Ser Met Leu Gln Arg Met Asn Glu Leu Ala Thr Gln Ser
         35                  40                  45

Ala Asn Gly Thr Asn Ser Asn Thr Asp Arg Lys Ala Ile Gln Asp Glu
     50                  55                  60

Ile Asp Gln Leu Thr Thr Glu Ile Asp Arg Val Ser Glu Thr Thr Lys
 65                  70                  75                  80

Phe Asn Glu Thr Tyr Leu Leu Lys Gly Asp Gly Ser Glu Lys Ala His
                 85                  90                  95

Asn Val Asn Ala His Asp Ala Gly Leu Asp Gly Val Thr Leu Thr Asp
            100                 105                 110

Lys Gly Asn Thr Val Asp Val Thr Leu Lys Thr Leu Asn Ala Gly Asp
        115                 120                 125

Lys Ile Ser Ile Ala Gly Lys Asn Tyr Thr Ile Gly Ser Lys Ala Ala
    130                 135                 140

Asp Ile Ala Ala Lys Ile Glu Ala Gly Thr Asp Thr Ala Lys Lys Ser
145                 150                 155                 160

Tyr Thr Val Asn Gly Thr Thr Tyr Gln Val Gly Thr Asn Val Phe
                165                 170                 175

Asp Ser Ala Gly Asn Lys Ile Lys Lys Ser Asp Leu Thr Gly Asn Ala
            180                 185                 190

Gly Asp Thr Gly Asp Ala Val Leu Lys Asp Leu Gln Asp Leu Val Lys
        195                 200                 205

Asp Gly Ser Thr Val Thr Ile Gly Thr Lys Thr Tyr Thr Ala Met Thr
    210                 215                 220

Asp Lys Asp Gly Gly Ala Asp Gly Ile Asp Asp Asn Asp Ser Thr Val
225                 230                 235                 240

Ile Thr Asp Gly Lys Ala Tyr Gln Leu Gln Thr Ala Glu Ile Val Lys
                245                 250                 255

Ala Ser Ser Ile Gly Ala Asp Thr Ala Ala Thr Asn Ala Thr Asn Ala
            260                 265                 270
```

```
Asn Asp Ala Tyr Asp Thr Ala Thr Thr Thr Phe Thr Leu Asn Lys Gly
        275                 280                 285

Asn Val Ser Tyr Lys Asp Gly Leu Ser Phe Asn Leu His Val Gly Ala
    290                 295                 300

Asp Ala Asp Met Thr Asn Lys Ile Ala Val Asn Ile Asp Ser Met Asn
305                 310                 315                 320

Ser Ala Gly Leu Gly Ile Lys Gly Ile Lys Ala Asp Thr Glu Gln Asp
                325                 330                 335

Ala Thr Tyr Ala Ile Asp Ala Ile Ala Asp Ile Ser Thr Val Ser
            340                 345                 350

Ser Gln Arg Ser Ala Leu Gly Ala Val Gln Asn Arg Leu Glu His Thr
        355                 360                 365

Ile Asn Asn Leu Asp Asn Val Val Glu Asn Thr Thr Ser Ala Glu Ser
    370                 375                 380

Arg Ile Arg Asp Thr Asp Met Ala Glu Glu Met Val Asn Tyr Ser Lys
385                 390                 395                 400

Asn Asn Ile Leu Ala Gln Ala Gly Gln Ser Met Leu Ala Gln Ala Asn
                405                 410                 415

Gln Ser Asn Gln Gly Val Leu Gln Leu Leu Gln
            420                 425

<210> SEQ ID NO 41
<211> LENGTH: 1368
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 41
gagaagatga ggaagcagat tcgtggactc gaccgtgctt caacaaatgc tcaggacggt      60
gtatcagcag tacagacagc agaaggtgcc ctcacagaag ttcactcaat gcttcagcgt     120
atgaatgagc ttgcaacaca ggcagctaac ggcacaaact ctacaacaga cagaaaagca     180
attcaggatg aggttgacca gctttctaca gagattgatc gtgtatctga cacaacaaag     240
tttaacgaga catatctcct aaaggtgat cagggaacaa agacaattaa tcttgaagct     300
catgatgctg gtttaaaggg aactctaaca acaacggag atggaacagc tacatttaca     360
atggatgcat taagggtgg cgataaaatc tctattggtg gtaagcagta tactatcggt     420
ggaactacag agcaggatgt gaaagacttc ctgaagaaga atggcgttga agataaagca     480
gatagcacat tttcaattac ttctggtaat aagacagtaa catataaata ctatgcggct     540
aaagctgatt tgcaactgg tggtaacaca acatatggat atgatgctgg atggtacaat     600
gaagctgatg ctccaactac ttcaacgact actggagatc aggctacagt aaatgctaag     660
aaaaaagatt catatgaagc ttttgctaca caaagtggaa catttacagc tgctggaaag     720
actttagaga aagctactat tacagatgct aacccaactg atggagtaga tgataaagat     780
tcaactgtaa tttctgttca gaaagcatat gagttagctg aaaagagct tttaaaggct     840 aatcagattg gagacacaga gggacacgct tctgtaaaaa atgcagatga ttctgatctt     900
gcatataatg ctggaaatgg tagttttaaa attaatcttg cacaggctaa agtagcaagt     960
acattaagct tcaaccttca tgtaggtgct gatgcagatt tgactaacaa gattcaggtc    1020
aacattgatg caatggattc tgcaagtctt ggtattaaag gattgaacgt aaatgacaag    1080
aacggaacag ctggaacata tgcaatcgat gctatttcag atgcaatctc aaaagtatct    1140
```

-continued

```
tcacagcgtt catcacttgg tgctgttcag aaccgtcttg agcacaccat caacaacctt    1200
gacaacgtag ttgagaatac tacatcagct gagtctcgta tccgtgatac agatatggca    1260
aaagagatgg ttaactacag caagaacaac attcttgcac aggctggaca gtctatgctt    1320
gcacaggcta atcagtctaa tcagggtgta cttcagctct acagtaa                  1368
```

<210> SEQ ID NO 42
<211> LENGTH: 455
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 42

```
Glu Lys Met Arg Lys Gln Ile Arg Gly Leu Asp Arg Ala Ser Thr Asn
1               5                   10                  15

Ala Gln Asp Gly Val Ser Ala Val Gln Thr Ala Glu Gly Ala Leu Thr
            20                  25                  30

Glu Val His Ser Met Leu Gln Arg Met Asn Glu Leu Ala Thr Gln Ala
        35                  40                  45

Ala Asn Gly Thr Asn Ser Thr Thr Asp Arg Lys Ala Ile Gln Asp Glu
    50                  55                  60

Val Asp Gln Leu Ser Thr Glu Ile Asp Arg Val Ser Glu Thr Thr Lys
65                  70                  75                  80

Phe Asn Glu Thr Tyr Leu Leu Lys Gly Asp Gln Gly Thr Lys Thr Ile
                85                  90                  95

Asn Leu Glu Ala His Asp Ala Gly Leu Lys Gly Thr Leu Thr Asn Asn
            100                 105                 110

Gly Asp Gly Thr Ala Thr Phe Thr Met Asp Ala Leu Lys Gly Gly Asp
        115                 120                 125

Lys Ile Ser Ile Gly Gly Lys Gln Tyr Thr Ile Gly Gly Thr Thr Glu
    130                 135                 140

Gln Asp Val Lys Asp Phe Leu Lys Lys Asn Gly Val Glu Asp Lys Ala
145                 150                 155                 160

Asp Ser Thr Phe Ser Ile Thr Ser Gly Asn Lys Thr Val Thr Tyr Lys
                165                 170                 175

Tyr Tyr Ala Ala Lys Ala Asp Val Ala Thr Gly Gly Asn Thr Thr Tyr
            180                 185                 190

Gly Tyr Asp Ala Gly Trp Tyr Asn Glu Ala Asp Ala Pro Thr Thr Ser
        195                 200                 205

Thr Thr Thr Gly Asp Gln Ala Thr Val Asn Ala Lys Lys Lys Asp Ser
    210                 215                 220

Tyr Glu Ala Phe Ala Thr Gln Ser Gly Thr Phe Thr Ala Ala Gly Lys
225                 230                 235                 240

Thr Leu Glu Lys Ala Thr Ile Thr Asp Ala Asn Pro Thr Asp Gly Val
                245                 250                 255

Asp Asp Lys Asp Ser Thr Val Ile Ser Val Gln Lys Ala Tyr Glu Leu
            260                 265                 270

Ala Gly Lys Glu Leu Leu Lys Ala Asn Gln Ile Gly Asp Thr Glu Gly
        275                 280                 285

His Ala Ser Val Lys Asn Ala Asp Asp Ser Asp Leu Ala Tyr Asn Ala
    290                 295                 300

Gly Asn Gly Ser Phe Lys Ile Asn Leu Ala Gln Ala Lys Val Ala Ser
305                 310                 315                 320
```

-continued

```
Thr Leu Ser Phe Asn Leu His Val Gly Ala Asp Ala Asp Leu Thr Asn
325                 330                 335
Lys Ile Gln Val Asn Ile Asp Ala Met Asp Ser Ala Ser Leu Gly Ile
        340                 345                 350
Lys Gly Leu Asn Val Asn Asp Lys Asn Gly Thr Ala Gly Thr Tyr Ala
355                 360                 365
Ile Asp Ala Ile Ser Asp Ala Ile Ser Lys Val Ser Ser Gln Arg Ser
370                 375                 380
Ser Leu Gly Ala Val Gln Asn Arg Leu Glu His Thr Ile Asn Asn Leu
385                 390                 395                 400
Asp Asn Val Val Glu Asn Thr Thr Ser Ala Glu Ser Arg Ile Arg Asp
            405                 410                 415
Thr Asp Met Ala Lys Glu Met Val Asn Tyr Ser Lys Asn Asn Ile Leu
        420                 425                 430
Ala Gln Ala Gly Gln Ser Met Leu Ala Gln Ala Asn Gln Ser Asn Gln
    435                 440                 445
Gly Val Leu Gln Leu Leu Gln
450                 455

<210> SEQ ID NO 43
<211> LENGTH: 1337
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 43
gagaagatga ggaagcagat ccgcggactg gacaaggcat cttccaatgc acaggatggt      60
gtatcatctg tacagactgc tgaaggtgct ttaacagaag ttcacagcat gttacagcgt     120
atgaatgaac ttgcagttca ggcagcaaac ggtacaaatt ccaaggatac agaccgtaag     180
gctatccagg acgagattga tcagttaaat acagagatcg accgtgttgc tgagacaacc     240
aaattcaatg agatttacct gttaaagggt gatgacggtg agaagacaat taatatgaag     300
gcacatgatg ccggattaaa gggaactctg accgataatg gtgatggaac agctacattt     360
aaaatggatg cattgaaggc tggagataaa gtttcaatcg gaggccagac gttttccatt     420
ggagcatcta caaagaatt aaaggacatg ttgacaactg ctgatattga tacaaagcac     480
caggatgttg tggtaaatgg agatacttat aaatatgtgg ctgcaaaagc agcagttaca     540
actggtacaa aggcagatgg aaatgcagct ggatggtata agacggagt tgtaccagcg     600 gatactggta ccggaattgt agcagatgca gattatgcgg atgcagctga atttagtaca     660
aaggtaacat ctggaactgt taagtaggt acaaaggaac tgtcccttat tgcagataat     720
gatggtgatg gagttgatga taacaacaaa aatgtaatca gtaaagaaaa agcatatagt     780
cttgcagcag ctgaattatt gaaagcaaac cagattggtg atactcagaa tcaggcaaaa     840
gtgggtattg ataaaaacta tactgcaatg acacttgcaa atgcaactaa tacaattgaa     900
attcatacag gaactgcaaa agttgccaac acattaagtt tcagcctcca tgtaggtgca     960
gatgctgaca tgacaaacaa gatcacagtt gatattgaca ccatgaactc tgcaaacctt    1020
ggaatcaagg gcttaaacgt aacggacaag acggtacag cagcaaccta cgcaatcgat    1080
gctatttccg atgcaatctc taaggtttct tcccagagat ctgcacttgg tgctgtacag    1140
aacagattag agcacaccat cgacaacctg gataatattt ccaagaatac atcttctgct    1200
gagtctcgta tccgtgatac agatatggca aaagagatgg taaactacag caagaacaac    1260
```

```
attcttgcac aggctggaca gtctatgctc gcacaggcta atcagtctaa tcagggtgta   1320
ctcagctctt acagtaa                                                  1337
```

<210> SEQ ID NO 44
<211> LENGTH: 445
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 44

```
Glu Lys Met Arg Lys Gln Ile Arg Gly Leu Asp Lys Ala Ser Ser Asn
1               5                   10                  15

Ala Gln Asp Gly Val Ser Ser Val Gln Thr Ala Glu Gly Ala Leu Thr
            20                  25                  30

Glu Val His Ser Met Leu Gln Arg Met Asn Glu Leu Ala Val Gln Ala
        35                  40                  45

Ala Asn Gly Thr Asn Ser Lys Asp Thr Asp Arg Lys Ala Ile Gln Asp
    50                  55                  60

Glu Ile Asp Gln Leu Asn Thr Glu Ile Asp Arg Val Ala Glu Thr Thr
65                  70                  75                  80

Lys Phe Asn Glu Ile Tyr Leu Leu Lys Gly Asp Asp Gly Glu Lys Thr
                85                  90                  95

Ile Asn Met Lys Ala His Asp Ala Gly Leu Lys Gly Thr Leu Thr Asp
            100                 105                 110

Asn Gly Asp Gly Thr Ala Thr Phe Lys Met Asp Ala Leu Lys Ala Gly
        115                 120                 125

Asp Lys Val Ser Ile Gly Gly Gln Thr Phe Ser Ile Gly Ala Ser Thr
    130                 135                 140

Lys Glu Leu Lys Asp Met Leu Thr Thr Ala Asp Ile Asp Thr Lys His
145                 150                 155                 160

Gln Asp Val Val Val Asn Gly Asp Thr Tyr Lys Tyr Val Ala Ala Lys
                165                 170                 175

Ala Ala Val Thr Thr Gly Thr Lys Ala Asp Gly Asn Ala Ala Gly Trp
            180                 185                 190

Tyr Lys Asp Gly Val Val Pro Ala Asp Thr Gly Thr Gly Ile Val Ala
        195                 200                 205

Asp Ala Asp Tyr Ala Asp Ala Ala Glu Phe Ser Thr Lys Val Thr Ser
    210                 215                 220

Gly Thr Val Lys Val Gly Thr Lys Glu Leu Ser Leu Ile Ala Asp Asn
225                 230                 235                 240

Asp Gly Asp Gly Val Asp Asp Asn Asn Lys Asn Val Ile Ser Lys Glu
                245                 250                 255

Lys Ala Tyr Ser Leu Ala Ala Ala Glu Leu Leu Lys Ala Asn Gln Ile
            260                 265                 270

Gly Asp Thr Gln Asn Gln Ala Lys Val Gly Ile Asp Lys Asn Tyr Thr
        275                 280                 285

Ala Met Thr Leu Ala Asn Ala Thr Asn Thr Ile Glu Ile His Thr Gly
    290                 295                 300

Thr Ala Lys Val Ala Asn Thr Leu Ser Phe Ser Leu His Val Gly Ala
305                 310                 315                 320

Asp Ala Asp Met Thr Asn Lys Ile Thr Val Asp Ile Asp Thr Met Asn
                325                 330                 335
```

```
Ser Ala Asn Leu Gly Ile Lys Gly Leu Asn Val Thr Asp Lys Asn Gly
340                 345                 350

Thr Ala Ala Thr Tyr Ala Ile Asp Ala Ile Ser Asp Ala Ile Ser Lys
355                 360                 365

Val Ser Ser Gln Arg Ser Ala Leu Gly Ala Val Gln Asn Arg Leu Glu
370                 375                 380

His Thr Ile Asp Asn Leu Asp Asn Ile Ser Lys Asn Thr Ser Ser Ala
385                 390                 395                 400

Glu Ser Arg Ile Arg Asp Thr Asp Met Ala Lys Glu Met Val Asn Tyr
405                 410                 415

Ser Lys Asn Asn Ile Leu Ala Gln Ala Gly Gln Ser Met Leu Ala Gln
420                 425                 430

Ala Asn Gln Ser Asn Gln Gly Val Leu Ser Ser Tyr Ser
435                 440                 445

<210> SEQ ID NO 45
<211> LENGTH: 1266
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 45
gagaagatga gtaagcagat ccgtggactg acaaggcttc ttccaatgca caggacggt      60 gtatcttctg tacagaccgc tgaaggtgct taacagaagt tcacagcatg ttacagcgt     120 atgaatgagc ttgcagttca ggcttctaac ggtacaaact ccaaggatac agaccgtaag    180
gctattcagg atgagatcga ccagttaaat acagagatcg accgtgttgc tgagacaacc    240
aaattcaatg agatttacct gttaaagggt gatgacggtg agaagaccgt aatatgaat    300 gcacatgatg ccggattaaa gggaacatta gttgataatg gttctggaaa agcaacattt    360
accatgaaag cactttccgc aggagacagt gtaagcatcg aggaaagaa ctatacaatt    420 ggaagtacag cagcagatgc acagaaaatt gtagatgcac agaaaaaggt tggcggaaaa    480
gttaccgtta atggtgtaga gtacacttat gataatgcag atacaaaatg gaaagatgca    540
gatggtaatg atgtaaagat tggaactggt gcaaatgcag gtgaaattaa aattggtgct    600
ggtgacaaag tatccgatgg aacaaccact ttaacagcta tgactgatga aaaaaatgca    660
gcaggtgcag ctacagcaga tggtgttgat gataatgata tagcgttat caccgcagaa    720 aaagcttatt cattagcaaa agatgaactt gttgctgcaa atcatattgg tgatacagaa    780
aatacggcag cagtagctca ggatactacg aacaagaata tatttaaaat tacaacaggt    840
tctgcaaaag ttgccaacac attaagcttc agccttcatg taggtgcaga tgctgacatg    900
accaacaaga tcacagtcga catcgacact atgaattctg caaaccttgg aatcaagggc    960
ttaaacgtaa ctgacaagaa cggtacagca gcaacctacg caatcgatgc tatttccgat   1020
gcaatctcta aggtttcttc ccagagatcc gcactcggtg ctgtacagaa cagattagag   1080
cacaccatcg acaacctgga taacattcc gagaatacat cttctgctga gtctcgtatc   1140
cgtgatacag atatggcaaa agagatggta aactacagca gaacaacat tcttgcacag   1200 gctggacagt ctatgcttgc acaggctaat cagtctaatc agggtgtact tcagctctta   1260
cagtaa                                                              1266

<210> SEQ ID NO 46
<211> LENGTH: 421
```

```
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 46
```

| | | | | | | | | | | | | | | | |
|---|---|---|---|---|---|---|---|---|---|---|---|---|---|---|---|
| Glu | Lys | Met | Ser | Lys | Gln | Ile | Arg | Gly | Leu | Asp | Lys | Ala | Ser | Ser | Asn |
| 1 | | | | 5 | | | | | 10 | | | | | 15 | |

| | | | | | | | | | | | |
|---|---|---|---|---|---|---|---|---|---|---|---|
| Ala | Gln | Asp | Gly | Val | Ser | Val | Gln | Thr | Ala | Glu | Gly | Ala | Leu | Thr |
| | 20 | | | | 25 | | | | 30 | | | | | |

| | | | | | | | | | | | |
|---|---|---|---|---|---|---|---|---|---|---|---|
| Glu | Val | His | Ser | Met | Leu | Gln | Arg | Met | Asn | Glu | Leu | Ala | Val | Gln | Ala |
| 35 | | | | 40 | | | | | 45 | | | | | | |

| Ser | Asn | Gly | Thr | Asn | Ser | Lys | Asp | Thr | Asp | Arg | Lys | Ala | Ile | Gln | Asp |
|---|---|---|---|---|---|---|---|---|---|---|---|---|---|---|---|
| 50 | | | | | 55 | | | | | 60 | | | | | |

| Glu | Ile | Asp | Gln | Leu | Asn | Thr | Glu | Ile | Asp | Arg | Val | Ala | Glu | Thr | Thr |
|---|---|---|---|---|---|---|---|---|---|---|---|---|---|---|---|
| 65 | | | | | 70 | | | | | 75 | | | | | 80 |

| Lys | Phe | Asn | Glu | Ile | Tyr | Leu | Leu | Lys | Gly | Asp | Gly | Glu | Lys | Thr |
|---|---|---|---|---|---|---|---|---|---|---|---|---|---|---|
| | 85 | | | | 90 | | | | | 95 | | | | | |

| Val | Asn | Met | Asn | Ala | His | Asp | Ala | Gly | Leu | Lys | Gly | Thr | Leu | Val | Asp |
|---|---|---|---|---|---|---|---|---|---|---|---|---|---|---|---|
| 100 | | | | | 105 | | | | | 110 | | | | | |

| Asn | Gly | Ser | Gly | Lys | Ala | Thr | Phe | Thr | Met | Lys | Ala | Leu | Ser | Ala | Gly |
|---|---|---|---|---|---|---|---|---|---|---|---|---|---|---|---|
| 115 | | | | | 120 | | | | | 125 | | | | | |

| Asp | Ser | Val | Ser | Ile | Gly | Gly | Lys | Asn | Tyr | Thr | Ile | Gly | Ser | Thr | Ala |
|---|---|---|---|---|---|---|---|---|---|---|---|---|---|---|---|
| 130 | | | | | 135 | | | | | 140 | | | | | |

| Ala | Asp | Ala | Gln | Lys | Ile | Val | Asp | Ala | Gln | Lys | Lys | Val | Gly | Gly | Lys |
|---|---|---|---|---|---|---|---|---|---|---|---|---|---|---|---|
| 145 | | | | | 150 | | | | | 155 | | | | | 160 |

| Val | Thr | Val | Asn | Gly | Val | Glu | Tyr | Thr | Tyr | Asp | Asn | Ala | Asp | Thr | Lys |
|---|---|---|---|---|---|---|---|---|---|---|---|---|---|---|---|
| | 165 | | | | 170 | | | | | 175 | | | | | |

| Trp | Lys | Asp | Ala | Asp | Gly | Asn | Asp | Val | Lys | Ile | Gly | Thr | Gly | Ala | Asn |
|---|---|---|---|---|---|---|---|---|---|---|---|---|---|---|---|
| 180 | | | | | 185 | | | | | 190 | | | | | |

| Ala | Gly | Glu | Ile | Lys | Ile | Gly | Ala | Gly | Asp | Lys | Val | Ser | Asp | Gly | Thr |
|---|---|---|---|---|---|---|---|---|---|---|---|---|---|---|---|
| 195 | | | | | 200 | | | | | 205 | | | | | |

| Thr | Thr | Leu | Thr | Ala | Met | Thr | Asp | Glu | Lys | Asn | Ala | Ala | Gly | Ala | Ala |
|---|---|---|---|---|---|---|---|---|---|---|---|---|---|---|---|
| 210 | | | | | 215 | | | | | 220 | | | | | |

| Thr | Ala | Asp | Gly | Val | Asp | Asp | Asn | Asp | Asn | Ser | Val | Ile | Thr | Ala | Glu |
|---|---|---|---|---|---|---|---|---|---|---|---|---|---|---|---|
| 225 | | | | | 230 | | | | | 235 | | | | | 240 |

| Lys | Ala | Tyr | Ser | Leu | Ala | Lys | Asp | Glu | Leu | Val | Ala | Ala | Asn | His | Ile |
|---|---|---|---|---|---|---|---|---|---|---|---|---|---|---|---|
| | 245 | | | | 250 | | | | | 255 | | | | | |

| Gly | Asp | Thr | Glu | Asn | Thr | Ala | Ala | Val | Ala | Gln | Asp | Thr | Thr | Asn | Lys |
|---|---|---|---|---|---|---|---|---|---|---|---|---|---|---|---|
| 260 | | | | | 265 | | | | | 270 | | | | | |

| Asn | Ile | Phe | Lys | Ile | Thr | Thr | Gly | Ser | Ala | Lys | Val | Ala | Asn | Thr | Leu |
|---|---|---|---|---|---|---|---|---|---|---|---|---|---|---|---|
| 275 | | | | | 280 | | | | | 285 | | | | | |

| Ser | Phe | Ser | Leu | His | Val | Gly | Ala | Asp | Ala | Asp | Met | Thr | Asn | Lys | Ile |
|---|---|---|---|---|---|---|---|---|---|---|---|---|---|---|---|
| 290 | | | | | 295 | | | | | 300 | | | | | |

| Thr | Val | Asp | Ile | Asp | Thr | Met | Asn | Ser | Ala | Asn | Leu | Gly | Ile | Lys | Gly |
|---|---|---|---|---|---|---|---|---|---|---|---|---|---|---|---|
| 305 | | | | | 310 | | | | | 315 | | | | | 320 |

| Leu | Asn | Val | Thr | Asp | Lys | Asn | Gly | Thr | Ala | Ala | Thr | Tyr | Ala | Ile | Asp |
|---|---|---|---|---|---|---|---|---|---|---|---|---|---|---|---|
| | 325 | | | | 330 | | | | | 335 | | | | | |

| Ala | Ile | Ser | Asp | Ala | Ile | Ser | Lys | Val | Ser | Ser | Gln | Arg | Ser | Ala | Leu |
|---|---|---|---|---|---|---|---|---|---|---|---|---|---|---|---|
| 340 | | | | | 345 | | | | | 350 | | | | | |

| Gly | Ala | Val | Gln | Asn | Arg | Leu | Glu | His | Thr | Ile | Asp | Asn | Leu | Asp | Asn |
|---|---|---|---|---|---|---|---|---|---|---|---|---|---|---|---|
| 355 | | | | | 360 | | | | | 365 | | | | | |

| Ile | Ser | Glu | Asn | Thr | Ser | Ser | Ala | Glu | Ser | Arg | Ile | Arg | Asp | Thr | Asp |
|---|---|---|---|---|---|---|---|---|---|---|---|---|---|---|---|
| 370 | | | | | 375 | | | | | 380 | | | | | |

```
Met Ala Lys Glu Met Val Asn Tyr Ser Lys Asn Asn Ile Leu Ala Gln
385                 390                 395                 400

Ala Gly Gln Ser Met Leu Ala Gln Ala Asn Gln Ser Asn Gln Gly Val
405                 410                 415

Leu Gln Leu Leu Gln
420
```

```
<210> SEQ ID NO 47
<211> LENGTH: 1338
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 47
```

| | | | | |
|---|---|---|---|---|
| gagaagatga | ggaagcaaat | ccgcggactg | gacaaggcat | cttccaatgc acaggatggt | 60 |
| gtatcatctg | tacagactgc | tgaaggtgct | ttaacagaag | ttcacagcat gttacagcgt | 120 |
| atgaatgaac | ttgcagttca | ggcagcaaac | ggtacaaatt | ccaaggatac agaccgtaag | 180 |
| gctatccagg | acgagattga | tcagttaaat | acagagatcg | accgtgttgc tgagacaacc | 240 |
| aaattcaatg | agatttacct | gttaaagggt | gatgacggtg | agaagacaat taatatgaag | 300 |
| gcacatgatg | ccggattaaa | gggaactctg | accgataatg | tgatggaac agctacattt | 360 |
| aaaatggatg | cattgaaggc | tggagataaa | gtttcaatcg | gaggccagac gttttccatt | 420 |
| ggagcatcta | caaagaatt | aaaggacatg | ttgacaactg | ctgatattga tacaaagcac | 480 |
| caggatgttg | tggtaaatgg | agatacttat | aaatatgtgg | ctgcaaaagc agcagttaca | 540 |
| actggtacaa | aggcagatgg | aaatgcagct | ggatggtata | agacggagt tgtaccagcg | 600 |
| gatactggta | ccggaattgt | agcagatgca | gattatgcgg | atgcagctga atttagtaca | 660 |
| aaggtaacat | ctggaactgt | taagtaggt | acaaaggaac | tgtcccttat tgcagataat | 720 |
| gatggtgatg | gagttgatga | taacaacaaa | aatgtaatca | gtaaagaaaa agcatatagt | 780 |
| cttgcagcag | ctgaattatt | gaaagcaaac | cagattggtg | atactcagaa tcaggcaaaa | 840 |
| gtgggtattg | ataaaaacta | tactgcaatg | acacttgcaa | atgcaactaa taccattgaa | 900 |
| attcatacag | gaactgcaaa | ggttgccaac | acattaagtt | tcagcctcca tgtaggtgca | 960 |
| gatgctgaca | tgacaaacaa | gatcacagtt | gatattgaca | ccatgaactc tgcaaaccctt | 1020 |
| ggaatcaagg | gcttaaacgt | aacggacaag | aacggtacag | cagcaaccta cgcaatcgat | 1080 |
| gctatttccg | atgcaatctc | taaggtttct | tcccagagat | ctgcacttgg tgctgtacag | 1140 |
| aacagattag | agcacaccat | cgacaacctg | gataatattt | ccgagaatac atcttctgct | 1200 |
| gagtctcgta | tccgtgatac | agatatggca | aaagagatgg | taaactacag caagaacaac | 1260 |
| attcttgcac | aggctggaca | gtctatgctc | gcacaggcta | atcagtctaa tcagggtgta | 1320 |
| cttcagctct | tacagtaa | | | | 1338 |

```
<210> SEQ ID NO 48
<211> LENGTH: 445
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 48
```

Glu Lys Met Arg Lys Gln Ile Arg Gly Leu Asp Lys Ala Ser Ser Asn

-continued

```
1               5               10              15
Ala Gln Asp Gly Val Ser Ser Val Gln Thr Ala Glu Gly Ala Leu Thr
20              25              30

Glu Val His Ser Met Leu Gln Arg Met Asn Glu Leu Ala Val Gln Ala
35              40              45

Ala Asn Gly Thr Asn Ser Lys Asp Thr Asp Arg Lys Ala Ile Gln Asp
50              55              60

Glu Ile Asp Gln Leu Asn Thr Glu Ile Asp Arg Val Ala Glu Thr Thr
65              70              75              80

Lys Phe Asn Glu Ile Tyr Leu Leu Lys Gly Asp Asp Gly Glu Lys Thr
85              90              95

Ile Asn Met Lys Ala His Asp Ala Gly Leu Lys Gly Thr Leu Thr Asp
100             105             110

Asn Gly Asp Gly Thr Ala Thr Phe Lys Met Asp Ala Leu Lys Ala Gly
115             120             125

Asp Lys Val Ser Ile Gly Gly Gln Thr Phe Ser Ile Gly Ala Ser Thr
130             135             140

Lys Glu Leu Lys Asp Met Leu Thr Thr Ala Asp Ile Asp Thr Lys His
145             150             155             160

Gln Asp Val Val Asn Gly Asp Thr Tyr Lys Tyr Val Ala Ala Lys
165             170             175

Ala Ala Val Thr Thr Gly Thr Lys Ala Asp Gly Asn Ala Ala Gly Trp
180             185             190

Tyr Lys Asp Gly Val Val Pro Ala Asp Thr Gly Thr Gly Ile Val Ala
195             200             205

Asp Ala Asp Tyr Ala Asp Ala Ala Glu Phe Ser Thr Lys Val Thr Ser
210             215             220

Gly Thr Val Lys Val Gly Thr Lys Glu Leu Ser Leu Ile Ala Asp Asn
225             230             235             240

Asp Gly Asp Gly Val Asp Asn Asn Lys Asn Val Ile Ser Lys Glu
245             250             255

Lys Ala Tyr Ser Leu Ala Ala Glu Leu Leu Lys Ala Asn Gln Ile
260             265             270

Gly Asp Thr Gln Asn Gln Ala Lys Val Gly Ile Asp Lys Asn Tyr Thr
275             280             285

Ala Met Thr Leu Ala Asn Ala Thr Asn Thr Ile Glu Ile His Thr Gly
290             295             300

Thr Ala Lys Val Ala Asn Thr Leu Ser Phe Ser Leu His Val Gly Ala
305             310             315             320

Asp Ala Asp Met Thr Asn Lys Ile Thr Val Asp Ile Asp Thr Met Asn
325             330             335

Ser Ala Asn Leu Gly Ile Lys Gly Leu Asn Val Thr Asp Lys Asn Gly
340             345             350

Thr Ala Ala Thr Tyr Ala Ile Asp Ala Ile Ser Asp Ala Ile Ser Lys
355             360             365

Val Ser Ser Gln Arg Ser Ala Leu Gly Ala Val Gln Asn Arg Leu Glu
370             375             380

His Thr Ile Asp Asn Leu Asp Asn Ile Ser Glu Asn Thr Ser Ser Ala
385             390             395             400

Glu Ser Arg Ile Arg Asp Thr Asp Met Ala Lys Glu Met Val Asn Tyr
405             410             415

Ser Lys Asn Asn Ile Leu Ala Gln Ala Gly Gln Ser Met Leu Ala Gln
420             425             430
```

Ala Asn Gln Ser Asn Gln Gly Val Leu Gln Leu Leu Gln
435                 440                 445

<210> SEQ ID NO 49
<211> LENGTH: 1229
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 49

| | | | | | |
|---|---|---|---|---|---|
| caacagctga | gggtgccttc | acagaagttc | acgatatgct | ccagagaatg | aatgagttag | 60 |
| cagtacaggc | agctaacgga | acaaactcag | aatcagatcg | tgatgatatc | cagaacgaaa | 120 |
| ttgaccagct | ttcacaggaa | atcgatcgta | tcgcatctac | aacaaagttc | aacgagactt | 180 |
| tcttattaaa | gggcgacatc | ggattaaagc | agctcaatat | agatgcacac | gatgcaggtc | 240 |
| ttgaaggtac | attagtacag | aactctacaa | gagcaacatt | tacaatggag | tctcttgaag | 300 |
| ctggtgaaaa | gtatagaatc | ggtggaacac | agtacacaat | cggagctaag | tcaaacaaag | 360 |
| aagtagctgc | tgctcttaag | ttttcagatg | atatgattca | aggcggtgaa | gaaggagcag | 420 |
| acgcttctac | agaatggaag | cttacagctg | tgatacaat | ctctatcgat | ggaaagactt | 480 |
| atacaattat | cgagggtgat | aacagtgatg | ttgctaatgc | taagattaca | aatggctacc | 540 |
| ttaatcacct | catcgttgcc | ggttcaacta | ttaagtataa | tggtaatgaa | gtaaagagat | 600 |
| tcacatctac | agcagatggt | attgataagg | cagatgcaac | acttgttaca | gctacagctg | 660 |
| catacaatat | ggtagctata | gagcttaaag | cagcatcttc | tattggtgca | acagataagg | 720 |
| cagcagatat | tgataaaaat | cctactactg | gaaaatattt | gtatgatacg | accgagatta | 780 |
| ctcagactgt | tggagctgat | cagactattc | ctaatacagt | aatcagcttc | actattaaga | 840 |
| aaggttacgt | aaacgtacag | aacgcactta | cacttaacct | tcacgttggt | gcagatgcag | 900 |
| cgatgacaaa | caagattaac | gttactatcg | aggctatgaa | ctctaagtca | atcggtatca | 960 |
| acggtatcaa | cgtatctgat | gcaactggta | aggcagcaac | atacgcaatc | gatgctatcg | 1020 |
| cagatgcaat | ccaaagagta | tcagcacagc | gtgcagaact | tggtgctatc | cagaacagat | 1080 |
| tagagcactc | tattagaaac | cttgacaacg | tagtagaaa | cacagaagca | gcagaatctc | 1140 |
| gtatccgtga | tacagatatg | gctgatcaga | tggttgagta | cagcaagaac | aatatcttac | 1200 |
| agcaggcagg | acaatcaatg | ctcgcacag | | | | 1229 |

<210> SEQ ID NO 50
<211> LENGTH: 409
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 50

Thr Ala Glu Gly Ala Phe Thr Glu Val His Asp Met Leu Gln Arg Met
1               5                   10                  15

Asn Glu Leu Ala Val Gln Ala Ala Asn Gly Thr Asn Ser Glu Ser Asp
            20                  25                  30

Arg Asp Asp Ile Gln Asn Glu Ile Asp Gln Leu Ser Gln Glu Ile Asp
        35                  40                  45

Arg Ile Ala Ser Thr Thr Lys Phe Asn Glu Thr Phe Leu Leu Lys Gly
    50                  55                  60

```
Asp Ile Gly Leu Lys Gln Leu Asn Ile Asp Ala His Asp Ala Gly Leu
 65                  70                  75                  80

Glu Gly Thr Leu Val Gln Asn Ser Thr Arg Ala Thr Phe Thr Met Glu
             85                  90                  95

Ser Leu Glu Ala Gly Glu Lys Tyr Arg Ile Gly Gly Thr Gln Tyr Thr
        100                 105                 110

Ile Gly Ala Lys Ser Asn Lys Glu Val Ala Ala Leu Lys Phe Ser
    115                 120                 125

Asp Asp Met Ile Gln Gly Gly Glu Gly Ala Asp Ala Ser Thr Glu
130                 135                 140

Trp Lys Leu Thr Ala Gly Asp Thr Ile Ser Ile Asp Gly Lys Thr Tyr
145                 150                 155                 160

Thr Ile Ile Glu Gly Asp Asn Ser Asp Val Ala Asn Ala Lys Ile Thr
165                 170                 175

Asn Gly Tyr Leu Asn His Leu Ile Val Ala Gly Ser Thr Ile Lys Tyr
    180                 185                 190

Asn Gly Asn Glu Val Lys Arg Phe Thr Ser Thr Ala Asp Gly Ile Asp
195                 200                 205

Lys Ala Asp Ala Thr Leu Val Thr Ala Thr Ala Tyr Asn Met Val
210                 215                 220

Ala Ile Glu Leu Lys Ala Ala Ser Ser Ile Gly Ala Thr Asp Lys Ala
225                 230                 235                 240

Ala Asp Ile Asp Lys Asn Pro Thr Thr Gly Lys Tyr Leu Tyr Asp Thr
245                 250                 255

Thr Glu Ile Thr Gln Thr Val Gly Ala Asp Gln Thr Ile Pro Asn Thr
260                 265                 270

Val Ile Ser Phe Thr Ile Lys Lys Gly Tyr Val Asn Val Gln Asn Ala
275                 280                 285

Leu Thr Leu Asn Leu His Val Gly Ala Asp Ala Ala Met Thr Asn Lys
290                 295                 300

Ile Asn Val Thr Ile Glu Ala Met Asn Ser Lys Ser Ile Gly Ile Asn
305                 310                 315                 320

Gly Ile Asn Val Ser Asp Ala Thr Gly Lys Ala Ala Thr Tyr Ala Ile
325                 330                 335

Asp Ala Ile Ala Asp Ala Ile Gln Arg Val Ser Ala Gln Arg Ala Glu
340                 345                 350

Leu Gly Ala Ile Gln Asn Arg Leu Glu His Ser Ile Arg Asn Leu Asp
355                 360                 365

Asn Val Val Glu Asn Thr Glu Ala Ala Glu Ser Arg Ile Arg Asp Thr
370                 375                 380

Asp Met Ala Asp Gln Met Val Glu Tyr Ser Lys Asn Asn Ile Leu Gln
385                 390                 395                 400

Gln Ala Gly Gln Ser Met Leu Ala Gln
405

<210> SEQ ID NO 51
<211> LENGTH: 224
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 151, 159, 165, 176, 177, 190, 200, 215, 216, 223
<223> OTHER INFORMATION: Xaa = any amino acid
```

<400> SEQUENCE: 51

```
Pro Glu Asp Cys Gln Asn Ile Leu Lys Met Trp Ser Pro Trp Asn Phe
1               5                   10                  15

Ser Arg Arg Ile Thr Pro Lys Asn Gly Thr Asp Gln Ala Gln Phe Leu
        20                  25                  30

Ile Ser Thr Asn Val Gly Glu Pro Lys Pro Leu His Met Val Ala
    35                  40                  45

Ser Gly Gly Glu Leu Ser Arg Ile Met Leu Ala Val Lys Thr Val Leu
50                  55                  60

Ala Asp Asp Asp Asp Ile Pro Thr Leu Ile Phe Asp Glu Ile Asp Thr
65                  70                  75                  80

Gly Ile Ser Gly Arg Thr Ala Gln Met Val Ser Glu Lys Leu Ser Tyr
            85                  90                  95

Ile Gly Arg Asn His Gln Val Leu Cys Ile Thr His Leu Pro Gln Ile
        100                 105                 110

Ala Phe Met Ala Asp Gly His Tyr Leu Ile Glu Lys Ser Ser Arg Thr
    115                 120                 125

Gly Lys Thr Lys Thr Gln Ile His Lys Leu Ala Pro Glu Glu Ser Val
130                 135                 140

Ser Glu Leu Ala Arg Leu Xaa Gly Gly Ala Gln Ile Thr Asp Xaa Val
145                 150                 155                 160

Leu Glu Asn Ala Xaa Glu Met Lys Lys Leu Ala Glu Gln Thr Lys Xaa
165                 170                 175

Xaa Lys Asn Lys Leu Asn Ile Tyr Arg Pro Gly Gln Asp Xaa Gln Lys
180                 185                 190

Glu Trp Asp Arg Ser Asn Lys Xaa Val Lys Ile Lys Gln Pro Ala Phe
195                 200                 205

Asp Arg Ser Pro Lys Asn Xaa Xaa Trp Glu Ser Glu Ser Xaa Pro
210                 215                 220
```

<210> SEQ ID NO 52
<211> LENGTH: 222
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: VARIANT
<222> LOCATION: 164, 166, 179, 189, 191, 196, 197, 198, 205, 212, 215, 218
<223> OTHER INFORMATION: Xaa = any amino acid

<400> SEQUENCE: 52

```
Ile Glu Glu Cys Lys Arg Leu Asp Glu Ala Gly Met Asp Tyr Asn Phe
1               5                   10                  15

Phe Tyr Leu Ala Gly Ile Tyr Gly Ser Gly His Met Glu Glu Gly Val
        20                  25                  30

Lys Asn Thr Ala Glu Val Phe Asn Gln Leu His Pro Lys Val Ile Val
    35                  40                  45

Ser Ser Met Leu Thr Val Tyr Pro Thr Ser Glu Leu Tyr Gln Glu Ile
50                  55                  60

Gln Ala Gly Asn Trp Thr Glu Glu Thr Glu Ile Glu Lys Leu Tyr Glu
65                  70                  75                  80

Leu Arg Thr Leu Val Gly Ser Leu Asp Ile Asp Thr Tyr Phe Ala Thr
            85                  90                  95

Met Gly Ala Ser Asn Cys Ile Asn Val Glu Gly His Leu Pro Lys Asp
```

```
                100                 105                 110
Arg Gly Arg Met Val Lys Trp Leu Asp Glu Val Ile Gly Ala Val Asp
    115                 120                 125

Glu Lys Glu Leu Arg Arg Tyr Arg Glu Asn Leu Arg His Leu Glu Gly
130                 135                 140

Lys Pro Tyr Arg Ile Ser Pro Leu Thr Gly Trp Ile Trp His Thr Thr
145                 150                 155                 160

Val Gln Pro Xaa Pro Xaa Leu Leu Phe Leu Leu Pro Gly Glu Asp Val
    165                 170                 175

Leu Leu Xaa Asp Met Gly Asp Gly His Arg Thr Ser Xaa Leu Xaa Gly
180                 185                 190

Phe Gly Ala Xaa Xaa Xaa Lys Met Glu Thr Arg Arg Xaa Ser Cys Ser
195                 200                 205

Arg Arg Ala Xaa Ser Pro Xaa Thr Ser Xaa Ala Gly Ser Val
210                 215                 220

<210> SEQ ID NO 53
<211> LENGTH: 83
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 17, 20, 29, 44, 51, 68, 75, 80
<223> OTHER INFORMATION: Xaa = any amino acid

<400> SEQUENCE: 53

Met Pro Ile Ala Arg Gln Arg Ser Ser Phe Cys Thr Arg Ser Arg Phe
1               5                   10                  15

Xaa Ser Val Xaa Ser Tyr Thr Asn Arg Glu Ile Ile Xaa Pro Phe Pro
            20                  25                  30

Ser Trp Ser Pro Ser Ser Cys Ser Ser Thr Ala Xaa Phe Cys Met Glu
35                  40                  45

Ser Ser Xaa Arg Leu Arg Phe Pro Ser Ser Ser Thr Val Ile Ser Met
50                  55                  60

Pro Leu Pro Xaa Ser Phe Lys Thr Cys Thr Xaa Thr Cys Gly Lys Xaa
65                  70                  75                  80

Ser Cys Ile

<210> SEQ ID NO 54
<211> LENGTH: 220
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 207
<223> OTHER INFORMATION: Xaa = any amino acid

<400> SEQUENCE: 54

Thr Pro Glu Glu Ala Asn Arg Leu Gly Cys Glu Leu Ala Arg Arg Phe
1               5                   10                  15

Thr Lys Gly Asn His Ala Phe Ile Val Cys Thr His Ile Asp Lys Ala
            20                  25                  30

His Ile His Asn His Ile Ile Trp Asn Ser Thr Thr Leu Asp Cys Thr
35                  40                  45
```

```
Arg Lys Phe Arg Asp Phe Leu Gly Ser Gly Arg Ala Val Arg Arg Leu
 50                  55                  60

Asn Asp Thr Ile Cys Ile Glu Asn Gly Tyr Ser Ile Val Ala Asn Pro
 65                  70                  75                  80

Lys Arg Arg Gly Lys Ser Tyr Asn Lys Trp Leu Gly Ser Lys Pro Pro
 85                  90                  95

Cys His Arg Asp Arg Leu Arg Met Ala Ile Asp Asp Ala Leu Ala Lys
100                 105                 110

Lys Pro Ala Asp Leu Asp Ala Leu Leu Lys Leu Gly Glu Ala Gly
115                 120                 125

Ile Glu Val Ser Pro Arg Gly Lys Phe Ile Arg Leu Arg Ala Pro Gly
130                 135                 140

Gln Lys Asn Phe Val Arg Leu Asp Gly Asp Ser Leu Gly Ala Glu Tyr
145                 150                 155                 160

Asp Ile Ser Ala Leu Leu Gly Pro Ser Ser Pro Gly Ser Gly Arg Thr
165                 170                 175

Arg Pro Ser Thr Lys Lys Gly Leu Pro Arg Arg Ser Ala Glu Arg Ser
180                 185                 190

Ile Trp Leu Val Asp Ile Gln Ala Lys Thr Pro Gly Pro Gly Xaa Gly
195                 200                 205

Ala Gly Tyr Ser Pro Gly Gly Ala Asn Val Val Gln
210                 215                 220

<210> SEQ ID NO 55
<211> LENGTH: 212
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 123, 171, 199, 210, 212
<223> OTHER INFORMATION: Xaa = any amino acid

<400> SEQUENCE: 55

Asp Leu Thr Gln Gln Pro Trp Cys Arg Asp Ala Leu Leu Leu His Val
  1                   5                  10                  15

Arg Gly Thr Gly Ala Leu Arg Trp Glu Thr Arg Ala Leu Pro Pro Lys
 20                  25                  30

Ala Asp Leu Tyr Glu Thr Pro Leu Cys Leu Thr Leu Arg Gly Thr Pro
 35                  40                  45

Leu Leu Ser Trp Phe Asp Ala Val Cys Glu Thr Cys Glu Ser Trp Leu
 50                  55                  60

Cys Thr Gly Trp Gly Leu Asp Thr Ala Glu Cys Pro Glu Leu Asp Ala
 65                  70                  75                  80

Leu Arg Gln Thr Leu Asn Gly Gly Phe Ala Gly Leu Glu Asp Ala Val
 85                  90                  95

Pro Ala Leu Ser Thr Leu Leu Glu Leu Leu Pro Glu Gly Val Tyr Val
100                 105                 110

Leu Ala Glu Ser Asp Ala Tyr Pro Thr Asp Xaa Cys Gly Gln Phe Phe
115                 120                 125

Trp Asn Val Ser Asp Cys Leu Glu Pro Asn Pro Ala Thr Gly Ala Val
130                 135                 140

Tyr Leu Asn Asp Asp Asp Tyr Asp Tyr Gln Tyr Glu Arg Leu Pro Pro
145                 150                 155                 160

Val Phe Leu Tyr Pro Pro Ser Gly Gly His Xaa Trp Ile Trp Ser Gly
```

-continued

```
              165                 170                 175
Trp Ser Ile Thr Lys Thr Ala Ser Arg Lys Thr Gly Leu Ser Pro Arg
180                 185                 190

Ala Cys Arg Leu Cys Gly Xaa Asp Val Arg Ser Ala Gly Arg Thr His
195                 200                 205

Lys Xaa Leu Xaa
210

<210> SEQ ID NO 56
<211> LENGTH: 225
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 37, 44, 87, 114, 123, 127, 141, 158, 167, 168, 176, 177,
      182, 199, 203, 206, 207, 208, 210, 212, 213, 216, 218, 219,
      220, 222, 223
<223> OTHER INFORMATION: Xaa = any amino acid

<400> SEQUENCE: 56

Lys Lys Val Gly Ala Arg Asn Asp Asn Val Val Thr Lys His Lys Phe
1               5                   10                  15

Thr Asn Arg Asn Gln Gln Arg Arg Gly Gln Gln Arg Arg Gly Lys Arg
            20                  25                  30

Glu Thr Glu Ala Xaa Arg Leu Arg Arg Ile Ala Xaa Glu Arg Lys Ala
35                  40                  45

Lys His Ile Thr Ile Glu Val Pro Glu Glu Ile Thr Val Gly Glu Phe
50                  55                  60

Ala Leu Arg Leu Lys Val Ser Ala Pro Glu Val Ile Lys Lys Leu Met
65                  70                  75                  80

Gly Leu Gly Val Phe Ala Xaa Ile Asn Asp Ala Ile Asp Phe Asp Thr
                85                  90                  95

Ala Val Leu Val Ala Asp Glu Phe His Ala Lys Val Glu Lys Glu Val
100                 105                 110

Val Xaa Thr Ile Glu Glu Arg Ile Ile Asp Xaa Ser Glu Asp Xaa Glu
115                 120                 125

Ala Asn Leu Ala Pro Arg Ala Pro Val Val Val Xaa Gly His Val
130                 135                 140

Asp His Gly Lys Thr Ser Ile Leu Asp Ala Ile Arg His Xaa Asn Val
145                 150                 155                 160

Thr Ile Gly Arg Gly Met Xaa Xaa Tyr Pro Ala His Arg Pro Ile Xaa
165                 170                 175

Xaa Lys Ser Gly Arg Xaa Gly Thr Pro Phe Leu Asp Thr Pro Gly His
180                 185                 190

Ala Ser Leu Pro Pro Cys Xaa Gln Gly Arg Xaa Gly Asp Xaa Xaa Xaa
195                 200                 205

Leu Xaa Leu Xaa Xaa Arg Gly Xaa Thr Xaa Xaa Xaa Pro Xaa Xaa Val
210                 215                 220

Glu
225

<210> SEQ ID NO 57
<211> LENGTH: 225
<212> TYPE: PRT
<213> ORGANISM: Artificial Sequence
<220> FEATURE:
```

```
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 164, 188, 190, 191, 195, 197, 209, 210, 222, 223, 225
<223> OTHER INFORMATION: Xaa = any amino acid

<400> SEQUENCE: 57

Lys Pro Ser Thr Met Ala Ala Ile Ile Ala Leu Ser Asp Glu Lys Val
1               5                   10                  15

Glu Glu Ile Cys Glu Cys Val Asp Gly Val Val Ala Ala Asn Tyr
            20              25                  30

Asn Cys Pro Gly Gln Ile Val Ile Ser Gly Glu Ile Glu Ala Val Asn
35                  40                  45

Ala Ala Cys Glu Ala Ala Lys Ala Ala Gly Ala Lys Arg Ala Leu Pro
50                  55                  60

Leu Lys Val Gly Gly Ala Phe His Ser Pro Leu Met Glu Pro Ala Arg
65                  70                  75                  80

Gln Glu Leu Ala Glu Ala Ile Ala Ala Thr Glu Phe His Thr Pro Val
            85                  90                  95

Cys Pro Val Tyr Gln Asn Val Asp Ala Ala Pro His Thr Asp Pro Ala
100                 105                 110

Glu Ile Lys Ala Asn Leu Ile Ala Gln Leu Thr Ala Pro Val Arg Trp
115                 120                 125

Thr Gln Thr Val Ala Asn Met Val Ala Asp Gly Ala Thr Glu Phe Val
130                 135                 140

Glu Leu Gly Pro Gly Lys Val Leu Gln Gly Leu Val Asn Lys Val Ser
145                 150                 155                 160

Arg Asp Val Xaa Val Ser Gly Lys Ala Val Thr Pro Asp Ala Arg Asp
165                 170                 175

Trp Pro Arg Asn Leu Pro Leu Leu Arg Lys Ser Xaa Thr Xaa Xaa Lys
180                 185                 190

Leu Ala Xaa Val Xaa Gly Phe Phe Thr Ser Leu Leu Trp Arg Gln Arg
195                 200                 205

Xaa Xaa Gly Pro Gly Ala Ser Gly His Phe Pro Asp Cys Xaa Xaa Ser
210                 215                 220

Xaa
225

<210> SEQ ID NO 58
<211> LENGTH: 228
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 183, 184, 195, 198, 217, 225, 227
<223> OTHER INFORMATION: Xaa = any amino acid

<400> SEQUENCE: 58

Gly His Lys Arg Ile Pro Ser Arg Glu Gly Gly Val Glu Ile Val Val
1               5                   10                  15

Glu Ala Leu Ala Val Arg Met Ala Glu Lys Gly His Lys Val Glu Ala
            20              25                  30

Tyr Asn Arg Tyr Gly His His Val Ser Gly Lys Lys Tyr Asp Glu Glu
35                  40                  45

Tyr Gly Arg Gly Asp Arg Lys Tyr Tyr Lys Gly Val Arg Ile His Ile
```

```
                    50                  55                  60
Val Pro Thr Phe Lys Ser Ser Lys Leu Asn Ala Ile Val Tyr Ser Phe
 65                  70                  75                  80

Phe Ala Thr Val Arg Ala Leu Val Lys Pro Tyr Asp Val Ile His Tyr
                 85                  90                  95

His Ala Glu Gly Pro Cys Ala Met Leu Trp Leu Pro Arg Leu Cys Gly
100                 105                 110

Lys Arg Val Val Ala Thr Ile His Gly Leu Asp Trp Gln Arg Ala Lys
115                 120                 125

Trp Gly Asn Phe Ala Ser Arg Val Ile Arg Phe Gly Glu Lys Met Ala
130                 135                 140

Ala Lys Tyr Ala Asp Glu Val Ile Val Leu Ser Glu Asn Val Arg Gln
145                 150                 155                 160

Tyr Phe Lys Asp Thr Tyr Gly Arg Asp Val Val Phe Ile Pro Asn Gly
165                 170                 175

Ile Glu Arg Pro Thr Arg Xaa Xaa Ala Glu Leu Ile Thr Gly Glu Ile
180                 185                 190

Arg Ile Xaa Gly Lys Xaa Ala Ile Ser Phe Phe Leu Ala Pro Asp Cys
195                 200                 205

Thr Pro Lys Lys Gly Leu Ala Leu Xaa Ser Lys His Phe Thr Lys Thr
210                 215                 220

Xaa Pro Xaa Asn
225

<210> SEQ ID NO 59
<211> LENGTH: 229
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 189, 192, 203, 223, 225, 226
<223> OTHER INFORMATION: Xaa = any amino acid

<400> SEQUENCE: 59

Gly Glu Lys Met Arg Asn Thr Leu Gln Thr Ile Arg Asp Val Ser Gly
  1               5                  10                  15

Gln Ile Asp Ser Gly Ser Glu Gln Leu Ala Cys Ala Ala Gln Asp Leu
                 20                  25                  30

Ala Glu Ser Cys Thr Val Gln Ala Gly Gln Val Ser Glu Leu Met Thr
 35                  40                  45

Ala Phe Gly Gly Met Thr Arg Ser Ile Glu Glu Asn Thr Arg Glu Ala
 50                  55                  60

Glu Asp Ser Ala Arg Met Ala Ser Glu Ala Gly Val Thr Leu Ala Lys
 65                  70                  75                  80

Gly Asn Glu Lys Met Gln Glu Leu Lys Asp Ser Ile Gln Glu Met Gly
                 85                  90                  95

Arg Cys Ser Glu Gln Ile Gly Ala Ile Ile Glu Ala Ile Glu Glu Ile
100                 105                 110

Ala Ser Gln Thr Asn Leu Leu Ala Leu Asn Ala Ala Ile Glu Ala Ala
115                 120                 125

Arg Ala Gly Asp Ala Gly Lys Gly Phe Ala Val Val Ala Glu Gln Val
130                 135                 140

Lys Asn Leu Ala Asn Glu Ser Ala Lys Ala Ala Gly Arg Thr Thr Glu
145                 150                 155                 160
```

```
Leu Ile Glu Thr Thr Val Ser Val Met Asp Arg Ser Ile Ser Ile Ala
165                 170                 175

Asp Glu Thr Ala Glu Asn Met Asn Leu Gly Asn Asp Xaa Arg Lys Xaa
180                 185                 190

Gly Tyr Arg Lys Asp Gly Thr Glu Leu Arg Xaa Met Phe Glu Gly Lys
195                 200                 205

Pro Ile Thr Pro Cys Leu Asp Leu Asn Glu Lys Leu Pro Phe Xaa Gly
210                 215                 220

Xaa Xaa Met Pro Gly
225

<210> SEQ ID NO 60
<211> LENGTH: 75
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 15, 16, 20, 52
<223> OTHER INFORMATION: Xaa = any amino acid

<400> SEQUENCE: 60

Arg Glu Ala Leu His Glu Ile Val Glu Asp Leu Lys Gln Asn Xaa Xaa
1               5                   10                  15

Thr Asn Gly Xaa Lys Gly Arg Gly Tyr Thr Gly Gln Arg Thr Gly Ser
20                  25                  30

Gly Lys Leu Trp Glu Thr Gly Gly Lys Asp Gly Lys Cys Ile Thr Asn
35                  40                  45

Arg Asn Cys Xaa Ser Thr Arg Ala Gly Ser Asp Phe Tyr Arg Gly Arg
50                  55                  60

Val Trp Arg Ile Ser Tyr Ile Gly Glu Leu Leu
65                  70                  75

<210> SEQ ID NO 61
<211> LENGTH: 98
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 67, 71, 76, 87, 90
<223> OTHER INFORMATION: Xaa = any amino acid

<400> SEQUENCE: 61

Ile Trp Gln Arg Val Gln Lys Lys Asn Leu Asn Thr Val Pro Gly Leu
1               5                   10                  15

Gly Ile His Val His Ile Pro Gly Gln Glu Asp Tyr Met Asn Gly Gln
20                  25                  30

Ile Asp Leu Val Ser Gly Arg Thr Ile Asp Val Ser Ile Leu Glu Tyr
35                  40                  45

Ile Pro Ser Met Arg Lys Glu Pro Arg Val Met Glu Lys Val Ala Glu
50                  55                  60

Leu Ile Xaa Arg Leu Pro Xaa Tyr Glu Ile Ile Xaa Asp Ile Gln Pro
65                  70                  75                  80

Glu Leu Ser Leu Trp Leu Xaa Val Pro Xaa Pro His Gly Lys Ser Ile
85                  90                  95
```

-continued

Leu Ile

<210> SEQ ID NO 62
<211> LENGTH: 220
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 21, 110, 175, 181, 204, 212, 213, 218, 220
<223> OTHER INFORMATION: Xaa = any amino acid

<400> SEQUENCE: 62

Arg Ala Ala Ala Ser Leu Gly Ile Pro Ala Ala Val His Glu Ser Asn
1               5                   10                  15

Ala Ile Pro Gly Xaa Thr Thr Arg Leu Leu Glu Lys His Ala Asp Leu
            20                  25                  30

Ile Met Val Gly Phe Glu Glu Cys Arg Lys Asn Tyr Arg His Pro Glu
        35                  40                  45

Lys Val Leu Val Thr Gly Thr Pro Val Arg Gly Asp Phe Phe Arg Leu
    50                  55                  60

Thr Arg Lys Gln Ala Lys Gln Lys Leu Gly Met Asp Asp Gly Arg Pro
65                  70                  75                  80

Leu Ile Val Ser Phe Trp Gly Ser Leu Gly Ala Arg Glu Met Asn Arg
                85                  90                  95

Gln Met Ala Glu Phe Leu Ala Leu Glu Ala Arg Asn Gly Xaa Pro Phe
            100                 105                 110

His His Val His Gly Ala Gly Lys Val Gly Tyr Leu His Met Ala Glu
        115                 120                 125

Tyr Leu Lys Asp Ala Gly Ile Asp Leu Asp Arg Ala Pro Gly Leu Glu
    130                 135                 140

Val Arg Glu Tyr Ile Gln Asp Met Gly Val Met Met Arg Ala Arg His
145                 150                 155                 160

Leu Val Ile Cys Arg Ala Gly Ala Ser Thr Ile Arg Arg Thr Xaa Ala
                165                 170                 175

Leu Gly Val Pro Xaa Ile Ile Val Pro Pro Gln Arg Asp His Asn His
            180                 185                 190

Gln Glu Phe Asn Ala Pro Arg Phe Ala Asn Arg Xaa Gly Ala Glu Ile
        195                 200                 205

Ile Pro Cys Xaa Xaa Gly Pro Arg Val Xaa Leu Xaa
    210                 215                 220

<210> SEQ ID NO 63
<211> LENGTH: 234
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 149, 166, 187, 188, 189, 197, 213, 214, 216, 217, 229
<223> OTHER INFORMATION: Xaa = any amino acid

<400> SEQUENCE: 63

Lys Leu Gly Glu Pro Leu Gln Val Lys Ala Val Leu Val Arg His Phe
1               5                   10                  15

Lys Asp Gly Pro Tyr Arg Gln Leu Met Thr Asp Asp Phe Lys Lys Ile
            20                  25                  30

```
Glu Glu Asp Gly Gly Ile Arg Val Val Glu Thr Ile Gly Gly Val
 35                  40                  45

Glu Ala Ala Tyr Glu Tyr Thr Lys Arg Cys Leu Ser Ala Gly Lys His
 50                  55                  60

Val Val Thr Ala Asn Lys Gln Leu Val Ala Glu Lys Gly Cys Glu Leu
 65                  70                  75                  80

Leu Ala Leu Ala Lys Lys Asn Val Ser Tyr Leu Phe Glu Ala Ser
 85                  90                  95

Val Gly Gly Gly Ile Pro Val Leu His Pro Leu Thr Gln Cys Met Ala
100                 105                 110

Ala Asn Arg Ile Asp Glu Val Tyr Gly Ile Leu Asn Gly Thr Thr Asn
115                 120                 125

Tyr Ile Leu Thr Arg Met Val Arg Thr Gly Ala Phe Phe Ser Asp Ala
130                 135                 140

Leu Arg Glu Ala Xaa Ala Lys Gly Tyr Ala Arg Gly Gly Pro His Arg
145                 150                 155                 160

Arg Arg Gly Gly His Xaa Arg Gly Ala Glu Asn Leu Ala Phe Trp Gly
165                 170                 175

Ile Trp Pro Phe Gly Ser Lys Ser Ala Cys Xaa Xaa Xaa Thr Pro Gly
180                 185                 190

Ser Thr Cys Thr Xaa Leu Asn Leu Ser Leu Asp Phe Cys Leu Ile Asp
195                 200                 205

Pro Val Met Thr Xaa Xaa Thr Xaa Xaa Trp Ile Phe Phe Lys Asn Ala
210                 215                 220

Ser Val Ala Pro Xaa Arg Phe Leu Leu Val
225                 230

<210> SEQ ID NO 64
<211> LENGTH: 225
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 188, 189, 205, 214, 216
<223> OTHER INFORMATION: Xaa = any amino acid

<400> SEQUENCE: 64

Ile Trp Arg Glu Val Val Arg Leu Lys Glu Lys Pro Ala Ile Val
  1               5                  10                  15

Ser Met Gly Asp Tyr Ala Ala Ser Gly Gly Tyr Tyr Ile Ser Cys Ala
 20                  25                  30

Ala Asn Arg Ile Phe Ala Asp Pro Thr Thr Leu Thr Gly Ser Ile Gly
 35                  40                  45

Ile Phe Gly Met Met Tyr Ser Gly Glu Lys Leu Phe Thr Glu Thr Leu
 50                  55                  60

Gly Leu Asn Phe Asp Val Val Lys Thr Asn Lys Met Ala Asp Leu Gly
 65                  70                  75                  80

Ala Ser Leu Gly Pro Val Leu Thr Arg Pro Leu Asn Ala Ser Glu Gln
 85                  90                  95

Glu Leu Met Gln Asn Tyr Val Asn Arg Gly Tyr Lys Leu Phe Val Asn
100                 105                 110

Arg Cys Ala Glu Gly Arg Lys Met Ser Thr Glu Ala Ile Glu Lys Val
115                 120                 125
```

```
Ala Glu Gly Arg Val Trp Thr Gly Ala Met Ala Lys Asp Leu Gly Leu
130                 135                 140

Val Asp Gln Leu Gly Gly Ile Asp Lys Ala Leu Asn Ala Ala Ala Thr
145                 150                 155                 160

Gln Ala Gly Ile Glu Asn Tyr Ser Ile Ile Ala Ser Lys Arg Lys Tyr
165                 170                 175

Phe Arg Lys Pro Ala Gly Gln Ser Glu Lys Thr Xaa Xaa Lys Gln Arg
180                 185                 190

Asn Arg Ile Phe Trp Glu Ala Ile Ile Gln Leu Gln Xaa Ala Trp Arg
195                 200                 205

Thr Lys Thr Pro Leu Xaa Thr Xaa Pro Met Pro Val Trp Thr Leu Tyr
210                 215                 220

Ser
225

<210> SEQ ID NO 65
<211> LENGTH: 224
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 81, 140, 186, 190, 204, 213
<223> OTHER INFORMATION: Xaa = any amino acid

<400> SEQUENCE: 65

Met Pro Glu Lys Leu Phe Glu Arg Tyr Cys Gln Asn Ser Asp Lys Ile
1               5                   10                  15

Ser Trp Phe Tyr Lys Asn Gly Asp Lys Gly Ile Glu Tyr Phe Ser Ile
                20                  25                  30

Val Tyr Glu Asp Asn Phe Gly Lys Gln Lys Ser Phe Tyr Pro Asp Tyr
35                  40                  45

Val Val Gly Thr Val Asp Gly Lys Val Trp Ile Ile Glu Thr Lys Gly
50                  55                  60

Gly Phe Thr Arg Val Gly Asp Ser Glu Asp Ile Asp Lys Tyr Thr Ala
65                  70                  75                  80

Xaa Lys Phe Leu Val Leu Lys Lys Tyr Leu Ala Lys Tyr Glu Leu His
85                  90                  95

Gly Gly Ile Val Arg Gln Asp Lys Gln Ser Ser Glu Leu Cys Ile Cys
100                 105                 110

Thr Asp Thr Tyr Ser Asp Asp Ile Lys Ser Asp Ser Trp Cys Leu Leu
115                 120                 125

Ser Asp Val Met Asn Arg Arg Ile Leu Gln Trp Xaa Ile Arg Thr Thr
130                 135                 140

Lys Arg Met Ser Gln Ser Ile Phe Ile Ile Leu Gln Phe Pro Ser Lys
145                 150                 155                 160

Lys Thr Val Pro Met Ser Pro His Ile Ile Ser Asn Arg Leu Leu Lys
165                 170                 175

Pro Phe Ser Lys Leu Val Gly Tyr Thr Xaa Gly Gln Glu Xaa Thr Asn
180                 185                 190

Pro Gln Ser Arg Tyr Gln Ile Cys Lys Lys Leu Xaa Gly Trp Ile Phe
195                 200                 205

Cys Phe Arg Trp Xaa Leu Tyr Asn Phe Val Arg Lys Tyr Asn His Val
210                 215                 220
```

```
<210> SEQ ID NO 66
<211> LENGTH: 232
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 150, 153, 158, 168, 182, 186, 188, 201, 206, 212, 223, 225,
      229, 232
<223> OTHER INFORMATION: Xaa = any amino acid

<400> SEQUENCE: 66

Leu Pro Leu Arg Gln Thr Gly Arg Asp Pro Ala Gly Arg Pro Glu Ser
1               5                  10                  15

Pro Gly Gly Ala Ala Gly Glu Asn Thr Gly Glu Arg Arg Arg Glu Ser
            20                  25                  30

Val Ser Leu Ser Val Asn Glu Leu Ser Asp Tyr Val Ile Ser Leu Arg
        35                  40                  45

Arg Glu Phe His Arg His Pro Glu Ile Ser Met Glu Glu Glu Trp Thr
50                  55                  60

Cys Ala Arg Ile Cys Gln Glu Leu Ser Ala Leu Gly Ile Pro Cys Glu
65                  70                  75                  80

Ile Val Gly Asp Lys Asn Val Ile Gly Arg Leu Glu Phe Gly Glu Gly
                85                  90                  95

Arg Arg Ile Ser Phe Arg Ala Asp Phe Asp Ala Leu Pro Val Gly Glu
            100                 105                 110

Thr Leu Asp Val Pro Trp Lys Ser Gln Gln Glu Asp Ala Met His Ala
        115                 120                 125

Cys Gly His Asp Gly His Thr Ala Ala Leu Leu Gly Ala Gly Arg Leu
    130                 135                 140

Leu Arg Ser Pro Gly Xaa Arg Leu Xaa Gly Thr Val Tyr Xaa Leu Leu
145                 150                 155                 160

Ser Thr Arg Pro Gly Gly Gly Xaa Arg Pro Pro Gly Met Pro Gly Val
                165                 170                 175

Ser Lys Thr Glu Arg Xaa Ser Gly Tyr Xaa His Xaa Arg Pro Phe Phe
            180                 185                 190

Ser Pro Phe Glu Asn Arg Asp His Xaa Leu Pro Arg Phe Xaa Gly Pro
        195                 200                 205

Lys Ala Pro Xaa Phe Phe Thr Phe Thr Leu Thr Gly Lys Arg Xaa Asp
    210                 215                 220

Xaa Gly Ser Leu Xaa His Ser Xaa
225                 230

<210> SEQ ID NO 67
<211> LENGTH: 207
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 76, 90, 162, 168, 183, 192, 196, 204
<223> OTHER INFORMATION: Xaa = any amino acid

<400> SEQUENCE: 67

Glu Lys Arg Ala Ile Lys Met Val Pro Gln Glu Ser Gln Ala Glu Gln
1               5                  10                  15

Ala Gln Val Trp Asp Tyr Leu Val Lys Thr Ala Pro Lys Ala Asp Met
```

```
                20                  25                  30
Gln Asp Asn Thr Val Lys Gly Ser Gln Phe Lys Gln Pro Tyr Leu Glu
 35                  40                  45

Phe Ser Gly Ser Cys Ala Gly Cys Ala Glu Thr Ser Tyr Ala Arg Leu
 50                  55                  60

Val Thr Gln Leu Phe Gly Asp Arg Met Tyr Ile Xaa Asn Ala Thr Gly
 65                  70                  75                  80

Cys Ser Ser Ile Trp Gly Gly Pro Ala Xaa Thr Ser Pro Tyr Cys Ala
 85                  90                  95

Asn Lys Glu Gly Lys Gly Pro Ala Trp Cys Asn Ser Leu Phe Glu Asp
100                 105                 110

Asn Ala Glu His Gly Leu Gly Met Tyr Ile Gly Gln Lys Ala Ile Arg
115                 120                 125

Ser Ala Leu Ala Glu Glu Thr Lys Gln Leu Ile Ala Val Glu Trp Ala
130                 135                 140

Tyr Gln Pro Leu Lys Asp Ala Ala Gln Lys Trp Leu Asp Thr Met Glu
145                 150                 155                 160

Asp Xaa Glu Ala Asn Gln Ala Xaa Arg Gln Gly Val His Cys Pro Cys
165                 170                 175

Trp Arg Arg Ser Leu Ile Xaa Leu Asp Glu Asn Glu Gly Val Tyr Xaa
180                 185                 190

Gln Pro Gln Xaa Arg Gly Lys Phe Ser Ala Thr Xaa Ala Thr Pro
195                 200                 205

<210> SEQ ID NO 68
<211> LENGTH: 208
<212> TYPE: PRT
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT
<220> FEATURE:
<221> NAME/KEY: VARIANT
<222> LOCATION: 185, 187, 201
<223> OTHER INFORMATION: Xaa = any amino acid

<400> SEQUENCE: 68

Arg Thr Arg Glu Pro Val Ser His Ser Ile Thr Ile Asn Gly Ala Ser
  1               5                  10                  15

Ala Pro Arg Val Ser Ser Glu Pro Gln Val Arg Thr Arg Glu Thr Ala
 20                  25                  30

Val His Asp Ala Tyr Thr Ala Ile Glu Gln Ala Pro Gln Ser Lys Pro
 35                  40                  45

Glu Arg Pro Gln Ile Lys Thr Arg Glu Ala Leu Ile Ser Gly Ser Pro
 50                  55                  60

Asp Arg Gly Ala Thr Ile Pro Pro Asp Arg Lys Pro Gly Pro Ser Asp
 65                  70                  75                  80

Pro Phe Ser Leu Lys Thr Lys Asp Ala Tyr Ile Gln Arg Gln Ser Thr
 85                  90                  95

Ala Pro Pro Glu Gln Pro Gln Ala Phe Thr Gln Gly Gln Gln Arg
100                 105                 110

Phe Ile Lys Ser Arg Ser Glu Ala Thr Thr Arg Lys Arg Ala Glu Val
115                 120                 125

Pro Arg Thr Gly Arg Ser Pro Val Val Gln Ala Lys Gly Gly Arg Glu
130                 135                 140

Ala Val Pro Ser Ala Pro Ala Arg Arg Gly Tyr Ala Gly Ser Gln Asn
145                 150                 155                 160
```

```
Arg Tyr Val Pro Val Gln Ala Val Arg Arg Thr Asp Arg Ser Gly Asn
165                 170                 175

Ala Arg Tyr Pro Thr Cys Ala Gly Xaa Gln Xaa Ala Gly His Gln Ser
        180                 185                 190

Ile Pro Phe Pro Ala Lys Lys Thr Xaa Ser Ala Pro Pro Ala Asn Ile
195                 200                 205
```

<210> SEQ ID NO 69
<211> LENGTH: 208
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: VARIANT
<222> LOCATION: 192, 200, 208
<223> OTHER INFORMATION: Xaa = any amino acid

<400> SEQUENCE: 69

```
Met Asn Gln Pro Glu Asn Pro Asp Ala Ala Ser Leu Val Ile Ala Val
1               5                   10                  15

Pro Thr Asp Glu Gln Val Ser Gly Gly Ser Phe Asn Pro Trp Gly Pro
            20                  25                  30

Thr Gly Pro Thr Glu Tyr Asn Asp Ile Thr Leu Glu Ala Gly Lys Leu
35                  40                  45

Glu Tyr Thr Gly Thr Asp Gly Asn Asp Asn Phe Ile Gly Asp Leu Ser
50                  55                  60

Gly Ser Ser Ser Arg Ser Thr Leu Gln Arg Asp Asp Val Ile Asp Gly
65                  70                  75                  80

Asn Gly Gly Asp Asp Met Leu Thr Val Ser Met Ala Arg Ser Trp Gly
            85                  90                  95

Gly Phe Ser Ser Lys Gly Gly Met Asp Asn Val Glu Thr Val Asn Leu
        100                 105                 110

Asn Asn Val Gly Asn Gly Ser Tyr Thr Phe Ser Ala Arg Gly Ile Asp
115                 120                 125

Gly Ala Asp Thr Phe Asn Ile Asp Gly Asn Ile Gly Leu Leu Asp Leu
130                 135                 140

Ser Ala Gly Thr Thr Val Asn Leu Thr Asn Thr Ser Ala Asn Thr Asn
145                 150                 155                 160

Ile Asp Phe Ile Pro Ser Glu Val Asn Asn Leu Asp Asp Ser Phe Thr
                165                 170                 175

Leu Gly Leu Asn Asn Val Arg His Val His Ser Arg Gly Asn Ile Xaa
        180                 185                 190

Leu Val Arg Val Asp Ala Ser Xaa Ile Glu Asn Leu Met Leu Asn Xaa
195                 200                 205
```

<210> SEQ ID NO 70
<211> LENGTH: 102
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: VARIANT
<222> LOCATION: 31
<223> OTHER INFORMATION: Xaa = any amino acid

<400> SEQUENCE: 70

```
Gly Gly Arg Asn Gln Val Gly Arg His Ala Glu Leu Ala Ala Gly Leu
1               5                   10                  15

Ala His Val Glu Pro Glu Ala Asp Asp Gly Gly Phe Ala Ala Xaa Leu
        20                  25                  30

Pro Val Val Gly Glu Val Ala Gly Gly Val Asp Ala Pro Arg Asp Pro
    35                  40                  45

Leu Leu Asp His Ala Arg Arg Asp Asp Gly Pro His Phe Gly Arg Arg
50                  55                  60

Ile Ala Cys Gly Val His Gly Arg Asp Asp Gly Ala His Arg Gly Ser
65                  70                  75                  80

Arg His Ala Leu Ser Ser Ser Val Arg Met Arg Ala Arg Tyr Pro Gly
            85                  90                  95

Ser Thr Cys Ser Gln Ala
            100
```

<210> SEQ ID NO 71
<211> LENGTH: 212
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT
<220> FEATURE:
<221> NAME/KEY: VARIANT
<222> LOCATION: 114, 123, 144, 148, 152, 159, 168, 179, 185, 186, 190, 195, 201, 206, 211
<223> OTHER INFORMATION: Xaa = any amino acid

<400> SEQUENCE: 71

```
Phe Lys Arg Arg Gly Gly Gln Gly Cys Leu Thr Gly Ala Glu Cys Gly
1               5                   10                  15

Glu Val Thr Val Lys Thr Asp Gly Tyr His Val Ala Val Gly Gly Val
        20                  25                  30

Val Leu His Pro Val Pro Arg Glu Ile Arg Glu Glu Leu Gly Glu Gln
    35                  40                  45

Gly Arg Val Ala Ile Thr Gly Ala Glu Thr Glu Leu Gly Gln Leu Pro
50                  55                  60

Gly Leu Gly Leu Pro Gly Ile Gly Asp Arg His Leu Ala Gly Asp Val
65                  70                  75                  80

Arg Leu His Glu His Gly Leu Gly Leu His Gly Gly Val His Leu Glu
            85                  90                  95

Gly Lys Gly Gly Gln Gly Gly Asp Ala Gly Leu Val Gly His Glu
100                 105                 110

Pro Xaa Gly Ile Gly Val Arg Val Leu Gly Xaa Arg Asp Ile Gly Val
    115                 120                 125

Ala Ala Gly His Gly Asn Gly Leu Asp Ala Leu Val Gly Ala His Xaa
130                 135                 140

Val Ser Glu Xaa Val Gly Leu Xaa Glu Leu His Leu Leu Gly Xaa Val
    145                 150                 155                 160

Pro Glu Gly Thr Gly Pro Ile Xaa Arg Val Leu Tyr His His Pro Gln
    165                 170                 175

Leu Ile Xaa Ala Gly Leu Gly Ser Xaa Xaa Val Ser Lys Xaa Asp Lys
180                 185                 190

Thr Ala Xaa Ala Arg Arg Lys Lys Xaa Gly Ile Phe Thr Xaa Pro Glu
195                 200                 205

Leu Met Xaa Thr
210
```

```
<210> SEQ ID NO 72
<211> LENGTH: 19
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 72
ggcccttctc caggacaga                                                      19

<210> SEQ ID NO 73
<211> LENGTH: 20
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 73
gctgatcatg gctgggttgt                                                     20

<210> SEQ ID NO 74
<211> LENGTH: 29
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 74
acttcatgca tcagctctcc actgtggat                                           29

<210> SEQ ID NO 75
<211> LENGTH: 22
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 75
cctgcagagt taagcatgcc ag                                                  22

<210> SEQ ID NO 76
<211> LENGTH: 23
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 76
tgcttgatca catgtctcga tcc                                                 23

<210> SEQ ID NO 77
<211> LENGTH: 23
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 77
tggccgagcc caagaccgtc tac                                                 23
```

<210> SEQ ID NO 78
<211> LENGTH: 20
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 78
gtacatcacc atggcgtatg                                         20

<210> SEQ ID NO 79
<211> LENGTH: 21
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 79
gctttcgtca agtcttcatt g                                       21

<210> SEQ ID NO 80
<211> LENGTH: 1501
<212> TYPE: DNA
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 80
cacagagcac acagagtaac acagagacga ttttaagttg ttgattcgta gtaaaaaact     60
ctgtgatact ctgctctgtg atactctgct ctgtgctgct ctgtggtgag ttctggcaca    120
gcacctttca gctaaatcac tcctgagtca agtctacagc gtaatagccg cgttttcctg    180
aagggaatac tcctgtgagg aagagtacct ggttcggtga cttcacagca gctttcatca    240
cttcttcaag gtcgctgact ttgcgcatag gctgatcgtt ggctttcagg atgatgaagc    300
ccttccgcac accggcatcc gccatcttgc ccgaagtgac tccggtaacc tgcaagccgt    360
atccgagatt gagttgtttc ttcaagtcgt ccggcaactc cttgaaggca gcgcccagaa    420
tctccatacc cgcatccttc acaatctttg ttgtaccttg ttcgttcttc aatgttatat    480
tgatattctt ttctttcttg tcacgcatca ccttcacggt cactttatcg cccggacgat    540
gctgtgcaat ggcttcctgc aggtcggcaa agttctgcac tttcttgcca tcgataccga    600
tgatgacatc atctaccttg atatcggaac cggcagcaga acctccatct acgatttcgc    660
gtacccaaac gccatccact acgccgaact cttgcgctt atcggacagt gtggctcccg    720
atttgtcgat cggctgatcg gacatcatat caccgtcacc gcaagcgaa gtaccttga    780 tacccagcaa cgcacgttgt acggttccgt attgtttcag gtcgctgacc actttggtca    840
tcacactggt cggaatggca aaaccgtatc cggcataagc gcctgtgggc gaagaaagca    900
cggcattgat acctaccaat tcaccttttg cattcaccaa agctccaccg ctgtttccct    960
gattgatggc ggcatctgtc tggatgaacg attctactcc cccgatgccg tacacaccga   1020
gcgtacgtgc cttggcactg acgataccgg cagttacagt cgaggtaaga ttgaacgggt   1080
tacctaccgc caatacccac tctcctactt tcaaggcatc agaatcgccc acggggatgg   1140
tcgggaaatc gtctccctcg atcttgacca gagccaaatc agaattcggg tcggtaccga   1200
tcatgcgacc tttaaaactcg cggttgtcat tcagcttaac gataatttcg tccgcaccgt   1260
cgatcacgtg attattggtg acgatgtaac cgtctttgga aatgatgaca ccggaaccga   1320

-continued

```
agccgacacg cggctgggtc tgtacacggc gctgctgtct gccaccatta ccgaagatat    1380
ccccgaatat ctctgcaaac gggtcgcgta cggtcacagt ttgttcttta gcctgttgag    1440
tcgattttat atgtactaca gcatgaagcg aattttccgc cgcctgcgtc agatctacag    1500
g                                                                   1501
```

<210> SEQ ID NO 81
<211> LENGTH: 515
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 81

```
Met Lys Gln Thr Thr Lys Asn Ile Leu Gly Ile Gly Ala Val Val Leu
1               5                   10                  15

Leu Ser Ala Gly Val Ala Gly Val Thr Thr Tyr Thr Met Leu Lys Pro
            20                  25                  30

Glu Asn Arg Asp Ser Leu Ser Phe Asn Glu Gln Phe Arg Gln Asn Pro
        35                  40                  45

Gly Ala Arg Leu Ala Ala Tyr Asp Ala Ile Asn Ala Gln Pro Val Asp
    50                  55                  60

Leu Thr Gln Ala Ala Glu Asn Ser Leu His Ala Val Val His Ile Lys
65                  70                  75                  80

Ser Thr Gln Gln Ala Lys Glu Gln Thr Val Thr Val Arg Asp Pro Phe
                85                  90                  95

Ala Glu Ile Phe Gly Asp Ile Phe Gly Asn Gly Gly Arg Gln Gln Arg
            100                 105                 110

Arg Val Gln Thr Gln Pro Arg Val Gly Phe Gly Ser Gly Val Ile Ile
        115                 120                 125

Ser Lys Asp Gly Tyr Ile Val Thr Asn Asn His Val Ile Asp Gly Ala
    130                 135                 140

Asp Glu Ile Ile Val Lys Leu Asn Asp Asn Arg Glu Phe Lys Gly Arg
145                 150                 155                 160

Met Ile Gly Thr Asp Pro Asn Ser Asp Leu Ala Leu Val Lys Ile Glu
                165                 170                 175

Gly Asp Asp Phe Pro Thr Ile Pro Val Gly Asp Ser Asp Ala Leu Lys
            180                 185                 190

Val Gly Glu Trp Val Leu Ala Val Gly Asn Pro Phe Asn Leu Thr Ser
        195                 200                 205

Thr Val Thr Ala Gly Ile Val Ser Ala Lys Ala Arg Thr Leu Gly Val
    210                 215                 220

Tyr Gly Ile Gly Gly Val Glu Ser Phe Ile Gln Thr Asp Ala Ala Ile
225                 230                 235                 240

Asn Gln Gly Asn Ser Gly Gly Ala Leu Val Asn Ala Lys Gly Glu Leu
                245                 250                 255

Val Gly Ile Asn Ala Val Leu Ser Ser Pro Thr Gly Ala Tyr Ala Gly
            260                 265                 270

Tyr Gly Phe Ala Ile Pro Thr Ser Val Met Thr Lys Val Val Ser Asp
        275                 280                 285

Leu Lys Gln Tyr Gly Thr Val Gln Arg Ala Leu Leu Gly Ile Lys Gly
    290                 295                 300

Thr Ser Leu Ala Gly Asp Gly Asp Met Met Ser Asp Gln Pro Ile Asp
305                 310                 315                 320
```

```
Lys Ser Gly Ala Thr Leu Ser Asp Lys Arg Lys Glu Phe Gly Val Val
325                 330                 335
Asp Gly Val Trp Val Arg Glu Ile Val Asp Gly Ser Ala Ala Gly
340                 345                 350
Ser Asp Ile Lys Val Asp Val Ile Ile Gly Ile Asp Gly Lys Lys
355                 360                 365
Val Gln Asn Phe Ala Asp Leu Gln Glu Ala Ile Ala Gln His Arg Pro
370                 375                 380
Gly Asp Lys Val Thr Val Lys Val Met Arg Asp Lys Lys Glu Lys Asn
385                 390                 395                 400
Ile Asn Ile Thr Leu Lys Asn Glu Gln Gly Thr Thr Lys Ile Val Lys
405                 410                 415
Asp Ala Gly Met Glu Ile Leu Gly Ala Ala Phe Lys Glu Leu Pro Asp
420                 425                 430
Asp Leu Lys Lys Gln Leu Asn Leu Gly Tyr Gly Leu Gln Val Thr Gly
435                 440                 445
Val Thr Ser Gly Lys Met Ala Asp Ala Gly Val Arg Lys Gly Phe Ile
450                 455                 460
Ile Leu Lys Ala Asn Asp Gln Pro Met Arg Lys Val Ser Asp Leu Glu
465                 470                 475                 480
Glu Val Met Lys Ala Ala Val Lys Ser Pro Asn Gln Val Leu Phe Leu
485                 490                 495
Thr Gly Val Phe Pro Ser Gly Lys Arg Gly Tyr Tyr Ala Val Asp Leu
500                 505                 510
Thr Gln Glu
515

<210> SEQ ID NO 82
<211> LENGTH: 1346
<212> TYPE: DNA
<213> ORGANISM: Artificial Sequence
<220> FEATURE:
<223> OTHER INFORMATION: DESCRIPTION OF ARTIFICIAL SEQUENCE: NOTE =
      SYNTHETIC CONSTRUCT

<400> SEQUENCE: 82
atggttttat tgatggccgt aagcttatca ttcgctcaaa tgaagaatgt aaaagaagcc      60
aaaagcattg ccagtgatgt aaaaccgaat tttaatcaag ctgaaaagct gattaatgaa     120
gccattaaga accctgagac caaggatctt cctgacacat gggacgttgc tggatttatt     180
cagaaacgtt ttatcgaaga gaacgtgat aagaaggtg ttctgaaaca gccgtttgac      240
acattgaagg catacaacag catttttaaaa atgtttgagt attatactaa atgtgatgat     300
ctagctcaag tacctaatga aaaaggtaaa attaaaaaca atatagaaa agcaaatgct     360 tcaactatat tggttgaacg tcctaatttg atcaacggtg gtattcaatt ctttaacctt     420
gataagaata aggaagcttt gcaattcttt gcaacatacg tagaatcagc ttcttatcct     480
atgttggcag agcaaaattt ggctaaaaca gatactcttt tggcacaaat agcatattac     540
gcaacattgg ctgctgacag agtaggagat aaagatgcaa ttattaaata tgctcctgct     600
gcattggatg acaaagatgg cggtaagttt gcaatgcaat tgatggcaga tgcatataaa     660
gctaaaggtg atactgcggc atgggttaaa tcattggaag aaggtatttt aaaattccct     720
ggaaatgatt atttctttgc gaatttggta gattactata ctagctctaa ccaagcttct     780
aaagctatgg aatttgctga tagaatgttg tctactgatg ccaataacaa gttgtatctt     840
```

```
tatgtgaaag catatcttta tcataatatg aaagaatatg ataatgctat tgagttctac    900
aagaaagcta ttgctgcaga tcctgaatat gcagaagcat attctaatgt aggattagtg    960
tatttgatga aggctcagga ttatgctgat aaagctacaa cagatatcaa tgatcctaaa   1020
tatgcagagg cacaagctac agtgaagaaa ttctatgaag aagctaagcc attctacgaa   1080
aaagccagag ctttgaaacc tgatcaaaaa gatttgtggt tacagggggct ttaccgtgtt   1140 tactataatc tgaacatggg tcctgaattt gaagaaatcg ataagatgat gaaataatta   1200
tattaagtca gttattataa aagactatcc caaaatttaa attgggatag tcttttatt    1260 tttacaaata aagaagcttg aatgatgatt ctgattttta tcaaactata taatgatgat   1320 tctcttttg tgagaaaata aaaag                                          1346
```

<210> SEQ ID NO 83
<211> LENGTH: 398
<212> TYPE: PRT
<213> ORGANISM: Artificial Sequence
<220> FEATURE:
<223> OTHER INFORMATION: DESCRIPTION OF ARTIFICIAL SEQUENCE: NOTE = SYNTHETIC CONSTRUCT

<400> SEQUENCE: 83

```
Met Val Leu Leu Met Ala Val Ser Leu Ser Phe Ala Gln Met Lys Asn
1               5                   10                  15

Val Lys Glu Ala Lys Ser Ile Ala Ser Asp Val Lys Pro Asn Phe Asn
            20                  25                  30

Gln Ala Glu Lys Leu Ile Asn Glu Ala Ile Lys Asn Pro Glu Thr Lys
        35                  40                  45

Asp Leu Pro Asp Thr Trp Asp Val Ala Gly Phe Ile Gln Lys Arg Phe
    50                  55                  60

Ile Glu Glu Glu Arg Asp Lys Lys Gly Val Leu Lys Gln Pro Phe Asp
65                  70                  75                  80

Thr Leu Lys Ala Tyr Asn Ser Ile Leu Lys Met Phe Glu Tyr Tyr Thr
                85                  90                  95

Lys Cys Asp Asp Leu Ala Gln Val Pro Asn Glu Lys Gly Lys Ile Lys
            100                 105                 110

Asn Lys Tyr Arg Lys Ala Asn Ala Ser Thr Ile Leu Val Glu Arg Pro
        115                 120                 125

Asn Leu Ile Asn Gly Gly Ile Gln Phe Phe Asn Leu Asp Lys Asn Lys
    130                 135                 140

Glu Ala Leu Gln Phe Phe Ala Thr Tyr Val Ser Ala Ser Tyr Pro
145                 150                 155                 160

Met Leu Ala Glu Gln Asn Leu Ala Lys Thr Asp Thr Leu Leu Ala Gln
                165                 170                 175

Ile Ala Tyr Tyr Ala Thr Leu Ala Ala Asp Arg Val Gly Asp Lys Asp
            180                 185                 190

Ala Ile Ile Lys Tyr Ala Pro Ala Ala Leu Asp Asp Lys Asp Gly Gly
        195                 200                 205

Lys Phe Ala Met Gln Leu Met Asp Ala Tyr Lys Ala Lys Gly Asp
    210                 215                 220

Thr Ala Ala Trp Val Lys Ser Leu Glu Glu Gly Ile Leu Lys Phe Pro
225                 230                 235                 240

Gly Asn Asp Tyr Phe Phe Ala Asn Leu Val Asp Tyr Tyr Thr Ser Ser
                245                 250                 255

Asn Gln Ala Ser Lys Ala Met Glu Phe Ala Asp Arg Met Leu Ser Thr
            260                 265                 270
```

```
Asp Ala Asn Asn Lys Leu Tyr Leu Tyr Val Lys Ala Tyr Leu Tyr His
275                 280                 285

Asn Met Lys Glu Tyr Asp Asn Ala Ile Glu Phe Tyr Lys Lys Ala Ile
290                 295                 300

Ala Ala Asp Pro Glu Tyr Ala Glu Ala Tyr Ser Asn Val Gly Leu Val
305                 310                 315                 320

Tyr Leu Met Lys Ala Gln Asp Tyr Ala Asp Lys Ala Thr Thr Asp Ile
325                 330                 335

Asn Asp Pro Lys Tyr Ala Glu Ala Gln Ala Thr Val Lys Lys Phe Tyr
340                 345                 350

Glu Glu Ala Lys Pro Phe Tyr Glu Lys Ala Arg Ala Leu Lys Pro Asp
355                 360                 365

Gln Lys Asp Leu Trp Leu Gln Gly Leu Tyr Arg Val Tyr Tyr Asn Leu
370                 375                 380

Asn Met Gly Pro Glu Phe Glu Glu Ile Asp Lys Met Met Lys
385                 390                 395
```

COMPOSITIONS AND METHODS FOR THE IDENTIFICATION AND TREATMENT OF IMMUNE-MEDIATED INFLAMMATORY DISEASES

CROSS-REFERENCE TO RELATED APPLICATIONS

This application claims benefit of U.S. Provisional Application No. 60/762,063, filed Jan. 24, 2006. U.S. Provisional Application No. 60/762,063, filed Jan. 24, 2006 is hereby incorporated herein by reference in its entirety.

ACKNOWLEDGEMENTS

This invention was made with government support under grants PO1 DK-44240 and NICE-01 from the National Institutes of Health and the National Institute of Diabetes and Digestive and Kidney, Broad Medical Foundation. The government has certain rights in the invention.

FIELD OF INVENTION

The present invention relates generally to therapy and diagnosis of immune-mediated inflammatory diseases (IMID) including inflammatory diseases such as Crohn's disease and ulcerative colitis (collectively referred to as inflammatory bowel disease, or IBD). The invention is more particularly related to polypeptides comprising at least a portion of a protein that is recognized, and to which individuals with immune-mediated inflammatory diseases mount an aberrant immune response. The invention also relates to polynucleotides encoding such polypeptides. Such polypeptides and polynucleotides are useful in pharmaceutical compositions, e.g., vaccines, and other compositions for the diagnosis and treatment of immune-mediated inflammatory disease.

BACKGROUND

The intestinal microbiota represent the largest mass and diversity of antigens encountered by the host immune system. Exposure to the microbiota is known to have profound effects on the mucosal immune system, which develop largely in response to microbial stimulation. The effects on the systemic immune system are less clear, but there are increasing data indicating that exposure to the microbes in the intestine can alter the development of immune diseases later in life. For example, provision of probiotic bacteria to newborn infants who had a high susceptibility to atopy reduced the incidence of this condition by 50% by age 5. One explanation of such data is that exposure to the microbiota, and possibly intestinal pathogens, early in life defines patterns of immune reactivity that can result in inflammatory or autoimmune diseases as individuals age.

The host immune response to the microbiota continues throughout life. This likely explains why the majority of lymphocytes and immunoglobulins in the body are located in the intestine. Some 3-5 gm of IgA are produced daily in the normal human intestine. There appears to be active communication among the microbiota, the intestinal epithelium, and the immune system. The innate immune system plays a particularly important role in the host response to the microbiota and, in turn, is sustained by this exposure. Adaptive immune responses to antigens of the microbiota in mice are compartmented tightly to the intestine and consist mainly of IgA in the secretions. Recent data indicate that there is no serum IgG antibody or systemic T cell reactivity to microbiota antigens detectable in normal mice; however, detectable levels of serum IgG antibody and systemic T cell reactivity were present in mice with colitis. The human response to the microbiota is largely undefined, but there do appear to be serum IgG antibodies to microbial antigens in normal humans. What those antigens are is yet to be defined.

A set of immunodominant microbiota antigens from mice has been cloned. These were defined using serum from colitic mice to screen a DNA library derived from murine commensal bacteria. These recombinant proteins represent a small fraction of the total potential proteins of the microbiota. Among these antigens, commensal bacterial flagellins represented some 20-25% of the total, which is entirely disproportionate to their representation in the total antigen pool. In addition, half of the subjects with Crohn's disease were found to have IgG antibodies to certain flagellin molecules, a reactivity that was not detected in normal humans or in subjects with a related inflammatory bowel disease, ulcerative colitis. Subsequent studies have found that Crohn's subjects with IgG antibodies to certain flagellin antigens have a more refractory or complicated course, illustrating that this seroreactivity is reflecting a pattern of host immune reactivity. Thus, IgG antibodies to these flagellin proteins of the microbiota can represent a biologic marker of prognostic value in Crohn's disease.

Crohn's Disease and ulcerative colitis (collectively referred to as inflammatory bowel disease, or IBD) are chronic, inflammatory diseases of the gastrointestinal tract. While the clinical features vary somewhat between these two disorders, both are characterized by abdominal pain, diarrhea (often bloody), a variable group of extra-intestinal manifestations (such as arthritis, uveitis, skin changes, etc.) and the accumulation of inflammatory cells within the small intestine and colon (observed in pathologic biopsy or surgical specimens).

IBD affects both children and adults, and has a bimodal age distribution (one peak around 20, and a second around 40). IBD is a chronic, lifelong disease, and is often grouped with other so-called "autoimmune" disorders (e.g. rheumatoid arthritis, type I diabetes mellitus, multiple sclerosis, etc.). IBD is found almost exclusively in the industrialized world. The most recent data from the Mayo Clinic suggest an overall incidence greater than 1 in 100,000 people in the United States, with prevalence data in some studies greater than 1 in 1000. There is a clear trend towards the increasing incidence of IBD in the US and Europe, particularly Crohn's Disease. The basis for this increase is not presently clear. As such, IBD represents the 2.sup.nd most common autoimmune disease in the United States (after rheumatoid arthritis).

Treatment of IBD is varied. First line therapy typically includes salicylate derivatives (e.g., 5-ASA) given orally or rectally. Response rates in uncomplicated Crohn's Disease are approximately 40% (compared to 20% for placebo). Corticosteroids remain a mainstay in the treatment of subjects with more "refractory" disease, despite the side-effects. Newer treatment options include anti-metabolites (e.g., methotrexate, 6-mercaptopurine) and immunomodulators (e.g. Remicade—a chimeric human antibody directed at the TNFα receptor).

There are many parallels between IBD and other immune-mediated inflammatory diseases (collectively known as IMIDs). IMIDs also affect both children and adults. As with IBD, treatments of IMIDs are varied but unsatisfactory because they do not change the natural history of these diseases. In spite of considerable research into therapies for these disorders, IMIDs remain difficult to diagnose and treat effectively. Furthermore, there are few laboratory tests that are diagnostic for IMIDS, and suitable laboratory tests that serve as "surrogate marker" that are uniformly useful to follow the course of disease in subjects are lacking. Accordingly, there is a need in the art for improved methods of detecting and treating such inflammatory bowel diseases. The present invention fulfills these needs and further provides other related advantages.

The properties that make a protein antigenic in one species are general and likely to be shared among other species. Thus, immunodominant antigens in mice will also be immunodominant in humans. Autoantigens are highly conserved among species and are not restricted to a given species. The same is true for antigens of the microbiota. Thus, the use of antigens of microbiota are widely useful.

Furthermore, because the microbiota represent the greatest mass of foreign antigen that the body encounters, the host immune response to the microbiota influences or determines immune reactivity to other antigens, including autoantigens. At a minimum, reactivity to the microbiota reflects the pattern of an individual's host immune reactivity.

Measurement of antibody reactivity to a panel or array of immunodominant antigens of the microbial flora reveals patterns of host immune reactivity that determine susceptibility to or severity of immune-mediated inflammatory and autoimmune diseases. Antibodies to the microbiota serve as a register and archive of the host antigenic experience with this large mass of microbial environmental antigens, both past and present. These antibody biomarkers provide a window into the immune system that was not previously available. These antigens and polynucleotides that encode them provide novel therapies because: alteration of the immune response to these microbiota antigens modulate immune reactivity to other antigens that drive the disease process.

SUMMARY OF THE INVENTION

In accordance with the purposes of this invention, as embodied and broadly described herein, this invention, in one aspect, relates to compositions and methods for the treatment and diagnosis of immune-mediated inflammatory diseases. The compositions disclosed herein include polypeptides, polynucleotides that encode such polypeptides, fragments, variants and derivatives of the disclosed polypeptide and polynucleotide sequences, antibodies and antibody fragments that specifically bind the disclosed polypeptides, antigen presenting cells that express such polypeptides, and T cells that are specific for cells expressing such polypeptides. Also disclosed are uses of the disclosed compostions including the diagnosis, prevention and treatment of immune-mediated inflammatory diseases.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects described below.

FIG. 10 shows IgG response to rIB and OVA in C3H/HeJ mice. Groups of mice were injected i.p. with rIB plus OVA in CFA on days 1 and 28 and serum IgG responses to each were measured by ELISA. IgG anti-rIB and anti-OVA titers in a serum pool of 5 C3H/HeJ mice before (day 0, -x-,), after the first i.p. immunization (day 28, -▲-), and 1 wk after the booster immunization (day 35, -o-). A, response to rIB 14 plus OVA. B, response to rIB 19 plus OVA. Data are expressed as OD-units at serial $\log_{10}$ dilutions of sera.

DETAILED DESCRIPTION

Figure 1A:
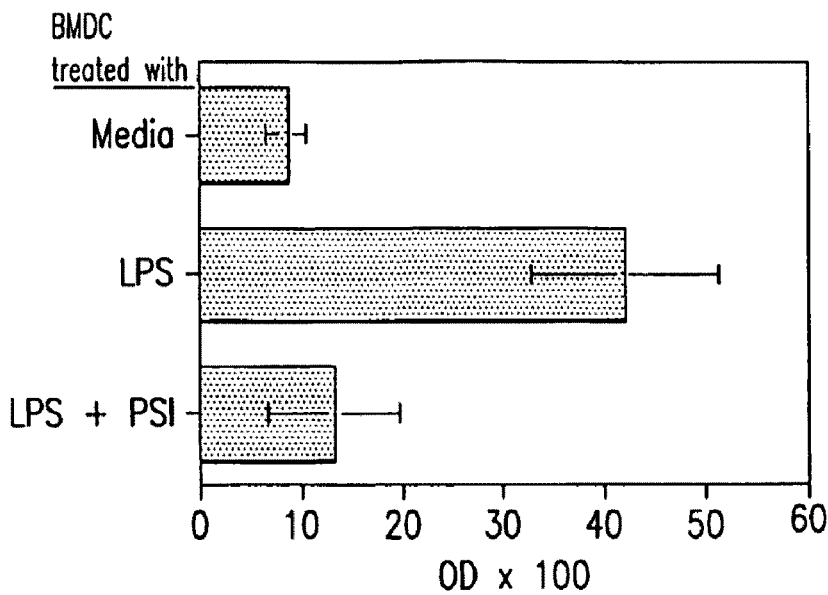
FIG. 1 shows PSI treatment inhibited BMDC NF-κβ activation and PSI-treated BMDC inhibited T cell proliferation and cytokine production. A. BMDC derived from BALB/c mice were cultured with media alone, with 1 μg/ml LPS, or with LPS and 1 μM PSI for 60 min. NF-κβ p65 in nuclear extracts was measured. B. BMDC derived from BALB/c mice were pulsed with or without 1 μM PSI for 4 hrs and then with 5 μg/ml OVA peptide for an additional 20 hrs, and then $2\times10^4$ pulsed BMDC were cultured with $1\times10^5$ CD4$^+$ T cells from DO11.10 RAG2$^{-/-}$ mice. $^3$H-TdR was added in the final 18 hrs of a 3-day culture. The results are expressed in mean CPM of triplicates+SD. C. Culture supernatants were collected at day 3 for measurement of IL-4, IL-10, and IFNα production, and day 1 for IL-2 production. Cytokines were measured by ELISA. One representative of three experiments is shown.

Before the present compounds, compositions, articles, devices, or methods are disclosed and described, it is to be understood that the aspects described below are not limited to specific synthetic methods or specific administration methods, as such may, of course, vary. It is also to be understood that the terminology used herein is for the purpose of describing particular aspects only and is not intended to be limiting.

It must be noted that, as used in the specification and the appended claims, the singular forms "a," "an" and "the" include plural referents unless the context clearly dictates otherwise.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human.

"Optional" or "optionally" means that the subsequently described event or circumstance can or cannot occur, and that the description includes instances where the event or circumstance occurs and instances where it does not. For example, the phrase "optionally the composition can comprise a combination" means that the composition may comprise a combination of different molecules or may not include a combination such that the description includes both the combination and the absence of the combination (i.e., individual members of the combination).

The term "vector" or "construct" refers to a nucleic acid molecule capable of transporting another nucleic acid to which it has been linked. The term "expression vector" or "expression construct" includes any vector, (e.g., a plasmid, cosmid or phage chromosome) containing a gene construct in a form suitable for expression by a cell (e.g., linked to a control element). "Plasmid" and "vector" are used interchangeably, as a plasmid is a commonly used form of vector. Moreover, the invention is intended to include other vectors which serve equivalent functions.

The terms "transformation" and "transfection" mean the introduction of a nucleic acid, e.g., an expression vector, into a recipient cell including introduction of a nucleic acid to the chromosomal DNA of said cell.

Ranges can be expressed herein as from "about" one particular value, or to "about" another particular value. When such a range is expressed, another embodiment includes from the one particular value or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

The present invention is directed generally to compositions and their use in the therapy and diagnosis of immune-mediated inflammatory diseases (herein also referred to as "IMIDs" or "inflammatory diseases"). IMIDs include, but are not limited to inflammatory bowel disease (IBD), systemic lupus erythematosus, Hashimoto's disease, rheumatoid arthritis, graft-versus-host disease, Sjögren's syndrome, pernicious anemia, Addison disease, scleroderma, Goodpasture's syndrome, ulcerative colitis, Crohn's disease, autoimmune hemolytic anemia, sterility, myasthenia gravis, multiple sclerosis, Basedow's disease, thrombopenia purpura, insulin-dependent diabetes mellitus, allergy; asthma, atopic disease, arteriosclerosis, myocarditis, cardiomyopathy, glomerular nephritis, hypoplastic anemia, and rejection after organ transplantation.

As described further below, illustrative compositions of the present invention include, but are not restricted to, polypeptides, polynucleotides encoding such polypeptides, antibodies and other binding agents, antigen presenting cells (APCs) and immune system cells (e.g., T and B cells).

Specifically disclosed are isolated polypeptides encoded by nucleotide sequences selected from the group consisting of SEQ ID NOs: 1-21, 23, 25, 27, 29, 31, 33, 35, 37, 39, 41, 43, 45, 47, 49, 80 or 82 or a sequence that hybridizes under stringent conditions to a polynucleotide sequence set forth in any one of SEQ ID NOs: 1-21, 23, 25, 27, 29, 31, 33, 35, 37, 39, 41, 43, 45, 47, 49, 80 or 82.

Also disclosed are isolated polypeptides that comprise an amino acid sequence selected from the group consisting of SEQ ID NOs: 22, 24, 26, 28, 30, 32, 35, 36, 38, 40, 42, 44, 46, 48, 50-71, 81 or 83. Further disclosed are isolated polypeptides having at least about 80, 85, 90, or 95% identity to isolated polypeptides encoded by nucleotide sequences selected from the group consisting of SEQ ID NOs: 1-21, 23, 25, 27, 29, 31, 33, 35, 37, 39, 41, 43, 45, 47, 49, 80 or 82. Also disclosed are isolated polypeptides having at least about 80, 85, 90, or 95% identity to polypeptides that comprise an amino acid sequence selected from the group consisting of SEQ ID NOs: 22, 24, 26, 28, 30, 32, 35, 36, 38, 40, 42, 44, 46, 48, 50-71, 81 or 83.

Further disclosed are isolated polypeptides having at least about 70, 75, 80, 85, 90, or 95% similarity to the isolated polypeptides encoded by a nucleotide sequence selected from the group consisting of SEQ ID NOs: 1-21, 23, 25, 27, 29, 31, 33, 35, 37, 39, 41, 43, 45, 47, 49, 80 or 82. Also disclosed are isolated polypeptides having at least about 70, 75, 80, 85, 90, or 95% similarity to polypeptides that comprise an amino acid sequence selected from the group consisting of SEQ ID NOs: 22, 24, 26, 28, 30, 32, 35, 36, 38, 40, 42, 44, 46, 48, 50-71, 81 or 83.

Also disclosed are fragments of polypeptides encoded by a nucleotide sequence selected from the group consisting of SEQ ID NOs: 1-21, 23, 25, 27, 29, 31, 33, 35, 37, 39, 41, 43, 45, 47, 49, 80 or 82. The fragments can comprise at least 10 contiguous amino acid residues of the encoded polypeptide.

Also disclosed are isolated polynucleotides comprising a sequence of SEQ ID NOs: 1-21, 23, 25, 27, 29, 31, 33, 35, 37, 39, 41, 43, 45, 47, 49, 80 or 82. Also disclosed are fragments of isolated polynucleotides comprising a sequence of SEQ ID NOs: 1-21, 23, 25, 27, 29, 31, 33, 35, 37, 39, 41, 43, 45, 47, 49, 80 or 82. Optionally, the fragment can comprise at least 20 contiguous residues of a sequence selected from the group consisting of SEQ ID NOs: 1-21, 23, 25, 27, 29, 31, 33, 35, 37, 39, 41, 43, 45, 47, 49, 80 or 82 and complements thereof.

An "isolated" polypeptide or an "isolated" polynucleotide is one that is removed from its original environment. For example, a naturally-occurring polypeptide or polynucleotide is isolated if it is separated from some or all of the coexisting materials in the natural system.

Optionally, isolated polypeptides or isolated nucleotides can also be purified, e.g., are at least about 90% pure, more preferably at least about 95% pure and most preferably at least about 99% pure.

Also disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular polypeptide is disclosed and discussed and a number of modifications that can be made to a number of molecules including the polypeptide are discussed, specifically contemplated is each and every combination and permutation of polypeptide and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that one way to define any known variants and derivatives or those that might arise, of the disclosed genes and proteins herein is through defining the variants and derivatives in terms of homology to specific known sequences. For example SEQ ID NO: 1 sets forth a particular sequence of a bacterial antigen and SEQ ID NO: 51 sets forth a particular sequence of the protein encoded by SEQ ID NO: 1, a bacterial protein. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference in its entirety and at least for material related to hybridization of nucleic acids). As used herein "stringent hybridization" for a DNA:DNA hybridization is about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

The invention provides polypeptides related to novel microbiota antigens. As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Thus, a "bacterial polypeptide" or "bacterial protein," refers generally to a polypeptide sequence of the present invention that is present in samples isolated from a substantial proportion of subjects with immune-mediated inflammatory diseases, for example preferably greater than about 20%, more preferably greater than about 30%, and most preferably greater than about 50% or more of subjects tested as determined using a representative assay provided herein. A bacterial polypeptide sequence of the invention, based upon its expression in enteric bacterial samples isolated from individuals with immune-mediated inflammatory diseases, has particular utility both as a diagnostic marker as well as a therapeutic target, as further described below. In one particular embodiment of the present invention, a bacterial polypeptide or bacterial protein comprises a flagellin protein.

The polypeptides of the present invention are sometimes herein referred to as bacterial proteins or bacterial polypeptides, as an indication that their identification has been based at least in part upon their expression in enteric bacterial samples isolated from the ceca of C3H/HeJ mice (SEQ ID NOs 1-20) or from cultures of enteric bacteria (SEQ ID Nos 21, 23, 25, 27, 29, 31, 33, 35, 37, 39, 41, 43, 45, 47 or 49 or from lysates of *Bacteroides thetaiotaomicron* or *Bacteroides fragilis* (SEQ ID Nos: 80 and 82, respectively). The peptides described herein may be identified from a lesion in the colon from a subject with IBD. Accordingly, such a peptide may not be present in adjacent normal tissue. Alternatively, a peptide of the present invention may be identified from an enteric bacterial sample isolated from the colon of an individual with IBD said enteric bacteria being absent from individuals not affected with IBD.

Optionally, the polypeptides of the present invention are identified by their ability to activate T cells from individuals affected with immune-mediated inflammatory diseases. Additionally, polypeptides described herein may be identified by their different reactivity with sera from subjects with immune-mediated inflammatory diseases as compared to sera from unaffected individuals. For example, polypeptides described herein may be identified by their reactivity with sera from subjects with immune-mediated inflammatory diseases as compared to their lack of reactivity to sera from unaffected individuals. Additionally, polypeptides described herein may be identified by their reactivity with sera from subjects with immune-mediated inflammatory diseases as compared to their higher reactivity to sera from unaffected individuals. Additionally, polypeptides described herein may be identified by their reactivity with sera from subjects with immune-mediated inflammatory diseases as compared to their lower reactivity to sera from unaffected individuals.

Optionally, the polypeptides of the invention can be immunogenic, i.e., they react detectably within an immunoassay (such as an ELISA or T-cell stimulation assay) with antisera or T-cells from a subject with an immune-mediated inflammatory disease. For example, the polypeptides of the invention react detectably within an immunoassay with antisera or T-cells from a subject with IBD. Screening for immunogenic activity can be performed using techniques well known to the skilled artisan. For example, such screens can be performed using methods such as those described in Harlow and Lane, Antibodies: A Laboratory Manual, Cold Spring Harbor Laboratory, 1988. In one illustrative example, a polypeptide may be immobilized on a solid support and contacted with subject sera to allow binding of antibodies within the sera to the immobilized polypeptide. For example, disclosed herein are solid supports comprising one or more polypeptides encoded by a nucleotide sequence selected from the group consisting of SEQ ID NOs: 1-21, 23, 25, 27, 29, 31, 33, 35, 37, 39, 41, 43, 45, 47, 49, 80 or 82 attached to the solid support. Additionally disclosed are solid supports comprising one or more polypeptides encoded by a nucleotide sequence selected from the group consisting of SEQ ID NOs: 1-21, 23, 25, 27, 29, 31, 33, 35, 37, 39, 41, 43, 45, 47, 49, 80 or 82 comprising an amino acid sequence of selected from the group consisting of SEQ ID NOs: 22, 24, 26, 28, 30, 32, 35, 36, 38, 40, 42, 44, 46, 48, 50-71, 81 or 83 attached to the solid support.

Solid supports are solid-state substrates or supports with which molecules, such as analytes and analyte binding molecules, can be associated. Analytes, such as calcifying nano-particles and proteins, can be associated with solid supports directly or indirectly. For example, analytes can be directly immobilized on solid supports. Analyte capture agents, such a capture compounds, can also be immobilized on solid supports. A preferred form of solid support is an array. Another form of solid support is an array detector. An array detector is a solid support to which multiple different capture compounds or detection compounds have been coupled in an array, grid, or other organized pattern.

Solid-state substrates for use in solid supports can include any solid material to which molecules can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A preferred form for a solid-state substrate is a microtiter dish, such as a standard 96-well type. In preferred embodiments, a multiwell glass slide can be employed that normally contain one array per well. This feature allows for greater control of assay reproducibility, increased throughput and sample handling, and ease of automation.

Different compounds can be used together as a set. The set can be used as a mixture of all or subsets of the compounds used separately in separate reactions, or immobilized in an array. Compounds used separately or as mixtures can be physically separable through, for example, association with or immobilization on a solid support. An array can include a plurality of compounds immobilized at identified or predefined locations on the array. Each predefined location on the array generally can have one type of component (that is, all the components at that location are the same). Each location will have multiple copies of the component. The spatial separation of different components in the array allows separate detection and identification of the polynucleotides or polypeptides disclosed herein.

Although preferred, it is not required that a given array be a single unit or structure. The set of compounds may be distributed over any number of solid supports. For example, at one extreme, each compound may be immobilized in a separate reaction tube or container, or on separate beads or microparticles. Different modes of the disclosed method can be performed with different components (for example, different compounds specific for different proteins) immobilized on a solid support.

Some solid supports can have capture compounds, such as antibodies, attached to a solid-state substrate. Such capture compounds can be specific for calcifying nano-particles or a protein on calcifying nano-particles. Captured calcifying nano-particles or proteins can then be detected by binding of a second, detection compound, such as an antibody. The detection compound can be specific for the same or a different protein on the calcifying nano-particle.

Methods for immobilizing antibodies (and other proteins) to solid-state substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is the heterobifunctional cross-linker N-[γ-Maleimidobutyryloxy]succinimide ester (GMBS). These and other attachment agents, as well as methods for their use in attachment, are described in *Protein immobilization: fundamentals and applications*, Richard F. Taylor, ed. (M. Dekker, New York, 1991); Johnstone and Thorpe, *Immunochemistry In Practice* (Blackwell Scientific Publications, Oxford, England, 1987) pages 209-216 and 241-242, and *Immobilized Affinity Ligands*; Craig T. Hermanson et al., eds. (Academic Press, New York, 1992) which are incorporated by reference in their entirety for methods of attaching antibodies to a solid-state substrate. Antibodies can be attached to a substrate by chemically cross-linking a free amino group on the antibody to reactive side groups present within the solid-state substrate. For example, antibodies may be chemically cross-linked to a substrate that contains free amino, carboxyl, or sulfur groups using glutaraldehyde, carbodiimides, or GMBS, respectively, as cross-linker agents. In this method, aqueous solutions containing free antibodies are incubated with the solid-state substrate in the presence of glutaraldehyde or carbodiimide.

A preferred method for attaching antibodies or other proteins to a solid-state substrate is to functionalize the substrate with an amino- or thiol-silane, and then to activate the functionalized substrate with a homobifunctional cross-linker agent such as (Bis-sulfo-succinimidyl suberate ($BS^3$) or a heterobifunctional cross-linker agent such as GMBS. For cross-linking with GMBS, glass substrates are chemically functionalized by immersing in a solution of mercaptopropyltrimethoxysilane (1% vol/vol in 95% ethanol pH 5.5) for 1 hour, rinsing in 95% ethanol and heating at 120° C. for 4 hrs. Thiol-derivatized slides are activated by immersing in a 0.5 mg/ml solution of GMBS in 1% dimethylformamide, 99% ethanol for 1 hour at room temperature. Antibodies or proteins are added directly to the activated substrate, which are then blocked with solutions containing agents such as 2% bovine serum albumin, and air-dried. Other standard immobilization chemistries are known by those of skill in the art.

Each of the components (compounds, for example) immobilized on the solid support preferably is located in a different predefined region of the solid support. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components preferably are immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

Optionally, at least one address on the solid support is the sequences or part of the sequences set forth in any of the nucleic acid sequences disclosed herein. Also disclosed are solid supports where at least one address is the sequences or portion of sequences set forth in any of the peptide sequences disclosed herein. Solid supports can also contain at least one address is a variant of the sequences or part of the sequences set forth in any of the nucleic acid sequences disclosed herein. Solid supports can also contain at least one address is a variant of the sequences or portion of sequences set forth in any of the peptide sequences disclosed herein.

Also disclosed are antigen microarrays for multiplex characterization of antibody responses. For example, disclosed are antigen arrays and miniaturized antigen arrays to perform large-scale multiplex characterization of antibody responses directed against the polypeptides, polynucleotides and antibodies described herein, using submicroliter quantities of biological samples as described in Robinson et al., Autoantigen microarrays for multiplex characterization of autoantibody responses, Nat Med., 8(3):295-301 (2002), which in herein incorporated by reference in its entirety for its teaching of contracting and using antigen arrays to perform large-scale multiplex characterization of antibody responses directed against structurally diverse antigens, using submicroliter quantities of biological samples.

Protein variants and derivatives are well understood to those of skill in the art and can involve amino acid sequence modifications. For example, amino acid sequence modifications typically fall into one or more of three classes: substitutional, insertional or deletional variants. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

Provided herein are polypeptides encoded by nucleotide sequences selected from the group consisting of SEQ ID NOs: 1-21, 23, 25, 27, 29, 31, 33, 35, 37, 39, 41, 43, 45, 47, 49, 80 or 82 or by a sequence that hybridizes under stringent conditions to a polynucleotide sequence set forth in any one of SEQ ID NOs: 1-21, 23, 25, 27, 29, 31, 33, 35, 37, 39, 41, 43, 45, 47, 49, 80 or 82 with substituted, inserted or deletional variations.

Also disclosed are isolated polypeptides that comprise an amino acid sequence selected from the group consisting of SEQ ID NOs: 22, 24, 26, 28, 30, 32, 35, 36, 38, 40, 42, 44, 46, 48, 50-71, 81 or 83 with substituted, inserted or deletional variations.

Insertions include amino or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion.

Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture.

Provided herein are polypeptides encoded by nucleotide sequences selected from the group consisting of SEQ ID NOs: 1-21, 23, 25, 27, 29, 31, 33, 35, 37, 39, 41, 43, 45, 47, 49, 80 or 82 or by a sequence that hybridizes under stringent conditions to a polynucleotide sequence set forth in any one of SEQ ID NOs: 1-21, 23, 25, 27, 29, 31, 33, 35, 37, 39, 41, 43, 45, 47, 49, 80 or 82 comprising one or more conserved amino acids. Also disclosed are isolated polypeptides that comprise an amino acid sequence selected from the group consisting of SEQ ID NOs: 22, 24, 26, 28, 30, 32, 35, 36, 38, 40, 42, 44, 46, 48, 50-71, 81 or 83 comprising one or more conserved amino acids.

Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 1 and are referred to as conservative substitutions.

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation or glycosylation.

For example, the replacement of one amino acid residue with another that is biologically and chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

TABLE 1

Amino Acid Substitutions
Original Residue Exemplary Conservative Substitutions,
others are known in the art.

ala; ser
arg; lys; gln
asn; gln; his
asp; glu
cys; ser
gln; asn; lys
glu; asp
gly; pro
his; asn; gln
ile; leu; val
Leu; ile; val
lys; arg; gln;
Met; leu; ile
phe; met; leu; tyr
ser; thr
thr; ser
trp; tyr
tyr; trp; phe
val; ile; leu It is understood that the description of conservative mutations and homology can be combined together in any combination, such as embodiments that have at least 70% homology to a particular sequence wherein the variants are conservative mutations.

It is understood that there are numerous amino acid and peptide analogs which can be incorporated into the disclosed compositions. For example, there are numerous D amino acids or amino acids which have a different functional substituent then the amino acids shown in Table 1. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —$CH$=$CH$— (cis and trans), —$COCH_2$—, —$CH(OH)$ $CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CH$ $H_2$—S); Hann J. Chem. Soc Perkin Trans. I 307-314 (1982) (—$CH$—$CH$—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—$CH(OH)CH_2$—); Holladay et al. Tetrahedron. Lett 24:4401-4404 (1983) (—C (OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Also disclosed are fusion polypeptides. A polypeptide may be a fusion polypeptide that comprises multiple polypeptides as described herein, or that comprises at least one polypeptide as described herein and an unrelated sequence, such as a known bacterial protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptides can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. New Engl. J. Med., 336:86-91, 1997).

Optionally, the immunologic fusion protein can be constructed by inserting a non-flagellin bacterial polypeptide sequence into the hypervariable region of a flagellin molecule as described by Cuadros, et. al. (Cuadros, et. al.: Flagellin Fusion Proteins as Adjuvants or Vaccines Induce Specific Immune Responses, Infect Immun 72; 2810, (2004)). For example, a non-flagellin bacterial polypeptide sequence can be inserted into the hypervariable region of SEQ ID NOs 21, 23, 25, 27, 29, 31, 33, 35, 37, 39, 41, 43, 45, 47; 49, 80, 82, or a flagellin derived from a pathogen such as $Salmonella$. Flagellins are both immunogenic and have adjuvant activity and thus these fusion proteins would have both properties.

Optionally, the immunological fusion partner is derived from a $Mycobacterium$ sp., such as a $Mycobacterium$ $tuberculosis$-derived Ra12 fragment. Ra12 compositions and methods for their use in enhancing the expression or immunogenicity of heterologous polynucleotide/polypeptide sequences is described in U.S. Patent Application No. 60/158, 585, the disclosure of which is incorporated herein by reference in its entirety. Briefly, Ra12 refers to a polynucleotide region that is a subsequence of a $Mycobacterium$ $tuberculosis$ MTB32A nucleic acid. MTB32A is a serine protease of 32 KD molecular weight encoded by a gene in virulent and avirulent strains of $M.$ $tuberculosis$. The nucleotide sequence and amino acid sequence of MTB32A have been described (for example, U.S. Patent Application No. 60/158,585; see also, Skeiky et al., Infection and Immun. (1999) 67:3998-4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions or insertions such that the biological activity of the encoded fusion polypeptide is not substantially diminished, relative to a fusion polypeptide comprising a native Ra12 polypeptide.

Optionally, an immunological fusion partner can be derived from protein D, a surface protein of the gram-negative bacterium $Haemophilus$ $influenza$ B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in $E.$ $coli$ (thus functioning as an expression enhancer). The lipid tail ensures optimal presentation of the antigen to antigen presenting cells. Other fusion partners include the non-structural protein from influenzae virus, NSI (hemaglutinin). Typically, the N-terminal 81 amino acids are used, although different fragments that include T-helper epitopes may be used.

Also disclosed is where the immunological fusion partner is the protein known as LYTA, or a portion thereof (preferably a C-terminal portion). LYTA is derived from $Streptococcus$ $pneumoniae$, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of E. coli C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Additionally, the fusion partner can comprise a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of CD4+ T-cells specific for the polypeptide.

Also disclosed is an immunogenic compositions comprising a polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82, an antigen and a suitable carrier. Suitable carriers are described below.

As this specification discusses various polypeptides and polypeptide sequences it is understood that the nucleic acids that can encode those polypeptide sequences are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptide sequences.

There are a variety of molecules disclosed herein that are nucleic acid based, including for example the nucleic acids that encode, for example, a polypeptide comprising an amino acid sequence selected from the group consisting of SEQ ID NOs: 22, 24, 26, 28, 30, 32, 35, 36, 38, 40, 42, 44, 46, 48, 50-71, 81 or 83, as well as various functional nucleic acids.

Also disclosed are complements of isolated polynucleotides comprising a sequence of SEQ ID NOs: 1-21, 23, 25, 27, 29, 31, 33, 35, 37, 39, 41, 43, 45, 47, 49, 80 or 82.

Also disclosed are fragments of isolated polynucleotides comprising a sequence of SEQ ID NOs: 1-21, 23, 25, 27, 29, 31, 33, 35, 37, 39, 41, 43, 45, 47, 49, 80 or 82. Optionally, the fragment can comprise at least 20 contiguous residues of a sequence selected from the group consisting of SEQ ID NOs: 1-21, 23, 25, 27, 29, 31, 33, 35, 37, 39, 41, 43, 45, 47, 49, 80 or 82 and complements thereof.

Also disclosed are isolated polynucleotides having at least 78, 80, 85, 90, or 95% identity to an isolated polynucleotide comprising a sequence of SEQ ID NOs: 1-21, 23, 25, 27, 29, 31, 33, 35, 37, 39, 41, 43, 45, 47, 49, 80 or 82. Further disclosed are degenerate variants of an isolated polynucleotide comprising a sequence of SEQ ID NOs: 1-21, 23, 25, 27, 29, 31, 33, 35, 37, 39, 41, 43, 45, 47, 49, 80 or 82.

Also disclosed are isolated polynucleotides comprising a sequence that selectively hybridizes under stringent conditions to a polynucleotide comprising a sequence of SEQ ID NOs: 1-21, 23, 25, 27, 29, 31, 33, 35, 37, 39, 41, 43, 45, 47, 49, 80 or 82. Also disclosed are isolated polynucleotides having at least 90% identity to an isolated polynucleotide comprising a sequence of SEQ ID NOs: 1-21, 23, 25, 27, 29, 31, 33, 35, 37, 39, 41; 43, 45, 47, 49, 80 or 82. Further disclosed are degenerate variants of an isolated polynucleotide comprising a sequence of SEQ ID NOs: 1-21, 23, 25, 27, 29, 31, 33, 35, 37, 39, 41, 43, 45, 47, 49, 80 or 82.

Also disclosed are isolated polynucleotides comprising a sequence that selectively hybridizes under stringent conditions to a polynucleotide comprising a sequence of SEQ ID NOs: 1-21, 23, 25, 27, 29, 31, 33, 35, 37, 39, 41, 43, 45, 47, 49, 80 or 82.

Optionally, one or more of the isolated polynucleotides of the invention are attached to a solid support. Solid supports are disclosed herein.

The disclosed nucleic acids are made up of for example, nucleotides, nucleotide analogs, or nucleotide substitutes. Non-limiting examples of these and other molecules are discussed herein. It is understood that for example, when a vector is expressed in a cell that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

The nucleotides of the invention can comprise one or more nucleotide analogs or substitutions. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[(CH$_2$)$_n$ O]$_m$ CH$_3$, —O(CH$_2$)$_n$ OCH$_3$, —O(CH$_2$)$_n$ NH$_2$, —O(CH$_2$)$_n$ CH$_3$, —O(CH$_2$)$_n$—ONH$_2$, and —O(CH$_2$)$_n$ON[(CH$_2$)$_n$ CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S, Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981, 957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety for their teaching of modifications and methods related to the same.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety for their teaching of modifications and methods related to the same.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety or sugar moieties replaced. Nucleotide substitutes do not contain a standard phosphorus atom. Substitutes for the phosphate can be, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185, 444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety for their teaching of modifications and methods related to the same.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference in its entirety for their teaching of modifications and methods related to the same. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference in its entirety for their teaching of modifications and methods related to the same.

The same methods of calculating homology as described above concerning polypeptides can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

Disclosed are compositions including primers and probes, which are capable of interacting with the polynucleotide sequences disclosed herein. In certain embodiments the primers are used to support DNA amplification reactions. Typically the primers will be capable of being extended in a sequence specific manner. Extension of a primer in a sequence specific manner includes any methods wherein the sequence or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the polynucleotide sequences disclosed herein or region of the polynucleotide sequences disclosed herein or they hybridize with the complement of the polynucleotide sequences disclosed herein or complement of a region of the polynucleotide sequences disclosed herein.

The size of the primers or probes for interaction with the polynucleotide sequences disclosed herein in certain embodiments can be any size that supports the desired enzymatic manipulation of the primer, such as DNA amplification or the simple hybridization of the probe or primer. A typical primer or probe would be at least 6, 7, 8, 9, 10, 20, 30, 40, 50, 60, 70, 80, 90, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long or any length inbetween.

Also disclosed are functional nucleic acids that can interact with the disclosed polynucleotides. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of polynucleotide sequences disclosed herein or the genomic DNA of the polynucleotide sequences disclosed herein or they can interact with the polypeptide encoded by the polynucleotide sequences disclosed herein. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Disclosed herein are antisense molecules that interact with the disclosed polynucleotides. Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437 each of which is herein incorporated by reference in its entirety for their teaching of modifications and methods related to the same.

Also disclosed are aptamers that interact with the disclosed polynucleotides. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. For example, when determining the specificity of aptamers, the background protein could be ef-1α. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Also disclosed are ribozymes that interact with the disclosed polynucleotides. Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Also disclosed are triplex forming functional nucleic acid molecules that interact with the disclosed polynucleotides. Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

Also disclosed are external guide sequences that form a complex with the disclosed polynucleotides. External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J. 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

Also disclosed are polynucleotides that contain peptide nucleic acids (PNAs) compositions. PNA is a DNA mimic in which the nucleobases are attached to a pseudopeptide backbone (Good and Nielsen, Antisense Nucleic Acid Drug Dev. 1997; 7(4) 431-37). PNA is able to be utilized in a number of methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (Trends Biotechnol 1997 June; 15(6): 224-9). As such, in certain embodiments, one may prepare PNA sequences that are complementary to one or more portions of an mRNA sequence based on the disclosed polynucleotides, and such PNA compositions may be used to regulate, alter, decrease, or reduce the translation of the disclosed polynucleotides transcribed mRNA, and thereby alter the level of the disclosed polynucleotide's activity in a host cell to which such PNA compositions have been administered.

PNAs have 2-aminoethyl-glycine linkages replacing the normal phosphodiester backbone of DNA (Nielsen et al., Science Dec. 6, 1991; 254(5037):1497-500; Hanvey et al., Science. Nov. 27, 1992; 258(5087):1481-5; Hyrup and Nielsen, Bioorg Med Chem. 1996 January; 4(1):5-23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 April; 3(4):437-45).

The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 April; 3(4):437-45; Petersen et al., J Pept Sci. 1995 May-June; 1(3):175-83; Orum et al., Biotechniques. 1995 September; 19(3):472-80; Footer et al., Biochemistry. Aug. 20, 1996; 35(33): 10673-9; Griffith et al., Nucleic Acids Res. Aug. 11, 1995; 23(15):3003-8; Pardridge et al., Proc Natl Acad Sci USA. Jun. 6, 1995; 92(12):5592-6; Boffa et al., Proc Natl Acad Sci USA. Mar. 14, 1995; 92(6):1901-5; Gambacorti-Passerini et al., Blood. Aug. 15, 1996; 88(4):1411-7; Armitage et al., Proc Natl Acad Sci USA. Nov. 11, 1997; 94(23):12320-5; Seeger et al., Biotechniques. 1997 September; 23(3):512-7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. Dec. 15, 1993; 65(24):3545-9) and Jensen et al. (Biochemistry. Apr. 22, 1997; 36(16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Disclosed herein are expression vectors comprising the polynucleotides of the invention operably linked to a control element. Also disclosed herein are host cells transformed or transfected with an expression vector comprising the polynucleotides of the invention. Also disclosed herein are methods of delivering the polynucleotides of the invention into cells. Also disclosed are host cells transformed or transfected with an expression vector comprising an isolated polynucleotide comprising a sequence of SEQ ID NOs: 1-21, 23, 25, 27, 29, 31, 33, 35, 37, 39, 41, 43, 45, 47, 49, 80 or 82 operably linked to an expression control sequence.

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

Expression vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). For example, disclosed herein are expression vectors comprising an isolated polynucleotide comprising a sequence of SEQ ID NOs: 1-21, 23, 25, 27, 29, 31, 33, 35, 37, 39, 41, 43, 45, 47, 49, 80 or 82 operably linked to a control element.

The "control elements" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUE-SCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Preferred promoters controlling transcription from vectors in mammalian host cells may be obtained from various sources, for example, the genomes of viruses such as polyoma, Simian Virus 40 (SV40), adenovirus, retroviruses, hepatitis-B virus and most preferably cytomegalovirus, or from heterologous mammalian promoters (e.g. beta actin promoter). The early and late promoters of the SV40 virus are conveniently obtained as an SV40 restriction fragment, which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Additional, promoters from the host cell or related species can also be used.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108

(1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Optionally, the promoter or enhancer region can act as a constitutive promoter or enhancer to maximize expression of the polynucleotides of the invention. In certain constructs the promoter or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases.

The expression vectors can include a nucleic acid sequence encoding a marker product. This marker product is used to determine if the gene has been delivered to the cell and once delivered is being expressed. Preferred marker genes are the E. Coli lacZ gene, which encodes β-galactosidase, and the gene encoding the green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

As used herein, plasmid or viral vectors are agents that transport the disclosed nucleic acids, such as an isolated polynucleotide comprising a sequence of SEQ ID NOs: 1-21, 23, 25, 27, 29, 31, 33, 35, 37, 39, 41, 43, 45, 47, 49, 80 or 82 into the cell without degradation and include a promoter yielding expression of the gene in the cells into which it is delivered. In some embodiments the isolated polynucleotides disclosed herein are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction abilities (i.e., ability to introduce genes) than chemical or physical methods of introducing genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

Retroviral vectors, in general, are described by Verma, I. M., Retroviral vectors for gene transfer. In Microbiology— 1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference in their entirety for their teaching of methods for using retroviral vectors for gene therapy.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serves as the priming site for the synthesis of the second strand of DNA synthesis, and specific sequences near the ends of the LTRs that enable the insertion of the DNA state of the retrovirus to insert into the host genome. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)) the teachings of which are incorporated herein by reference in their entirety for their teaching of methods for using retroviral vectors for gene therapy. Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. Optionally, both the E1 and E3 genes are removed from the adenovirus genome.

Another type of viral vector that can be used to introduce the polynucleotides of the invention into a cell is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference in its entirety for material related to the AAV vector.

The disclosed vectors thus can provide DNA molecules that are capable of integration into a mammalian chromosome without substantial toxicity.

The inserted genes in viral and retroviral vectors usually contain promoters, or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Other useful systems include, for example, replicating and host-restricted non-replicating vaccinia virus vectors.

In addition, the disclosed polynucleotides can be delivered to a target cell in a non-nucliec acid based system. For example, the disclosed polynucleotides can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed expression vectors, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood, to a target organ, or inhaled into the respiratory tract to target cells of the respiratory tract. For example, a composition comprising a polynucleotide described herein and a cationic liposome can be administered to a subjects lung cells. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described herein, delivery of the compositions to cells can be via a variety of mechanisms. As one example, delivery can be via a liposome, using commercially available liposome preparations such as LIPOFECTIN™, LIPOFECTAMINE™ (GIBCO-BRL, Gaithersburg, Md.), SUPERFECT™ (QIAGEN, Hilden, Germany) and TRANSFECTAM™ (Promega Biotec, Madison, Wis.), as well as other liposomes developed according to procedures standard in the art. In addition, the disclosed nucleic acid or vector can be delivered in vivo by electroporation, the technology for which is available from Genetronics (San Diego, Calif.) as well as by means of a SONOPORATION™ machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:62.14-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

As described herein, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

The nucleic acids, such as, the polynucleotides described herein, such as SEQ ID NOs: 1-21, 23, 25, 27, 29, 31, 33, 35, 37, 39, 41, 43, 45, 47, 49, 80 or 82, can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 3rd Edition (Cold Spring Harbor Laboratory Press, Cold Spring Harbor, N.Y., 2001) Chapters 5, 6) to purely synthetic methods, for example, by the cyanoethyl phosphoramidite method using a Milligen or Beckman System 1Plus DNA synthesizer. Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

One method of producing the disclosed polypeptides, such as SEQ ID NOs: 22, 24, 26, 28, 30, 32, 35, 36, 38, 40, 42, 44, 46, 48, 50-71, 81 or 83, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which are both herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chem. IV. Academic Press, New York, pp. 257-267 (1992)).

For example, disclosed is a method of making a polypeptide comprising culturing a host cell transformed or transfected with an expression vector comprising a polynucleotide sequence selected from the group consisting of SEQ ID NOs: 1-21, 23, 25, 27, 29, 31, 33, 35, 37, 39, 41, 43, 45, 47, 49, 80 or 82 under conditions whereby the polynucleotide is expressed and recovering the polypeptide expressed by the polynucleotide.

Also disclosed herein are isolated antibodies, antibody fragments and antigen-binding fragments thereof that specifically bind to a polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82. Optionally, the isolated antibodies, antibody fragments, or antigen-binding fragment thereof can be neutralizing antibodies. The antibodies, antibody fragments and antigen-binding fragments thereof disclosed herein can be identified using the methods disclosed herein. For example, antibodies that bind to the polypeptides of the invention can be isolated using the antigen microarray described above.

The term "antibodies" is used herein in a broad sense and includes both polyclonal and monoclonal antibodies. In addition to intact immunoglobulin molecules, also disclosed are antibody fragments or polymers of those immunoglobulin molecules, and human or humanized versions of immunoglobulin molecules or fragments thereof, as long as they are chosen for their ability to interact with the polypeptides disclosed herein.

"Antibody fragments" are portions of a complete antibody. A complete antibody refers to an antibody having two complete light chains and two complete heavy chains. An antibody fragment lacks all or a portion of one or more of the chains. Examples of antibody fragments include, but are not limited to, half antibodies and fragments of half antibodies. A half antibody is composed of a single light chain and a single heavy chain. Half antibodies and half antibody fragments can be produced by reducing an antibody or antibody fragment having two light chains and two heavy chains. Such antibody fragments are referred to as reduced antibodies. Reduced antibodies have exposed and reactive sulfhydryl groups. These sulfhydryl groups can be used as reactive chemical groups or coupling of biomolecules to the antibody fragment. A preferred half antibody fragment is a F(ab). The hinge region of an antibody or antibody fragment is the region where the light chain ends and the heavy chain goes on.

Antibody fragments for use in antibody conjugates can bind antigens. Preferably, the antibody fragment is specific for an antigen. An antibody or antibody fragment is specific for an antigen if it binds with significantly greater affinity to one epitope than to other epitopes. The antigen can be any molecule, compound, composition, or portion thereof to which an antibody fragment can bind. An analyte can be any molecule, compound or composition of interest. For example, the antigen can be a polynucleotide of the invention.

The antibodies or antibody fragments can be tested for their desired activity using the in vitro assays described herein, or by analogous methods, after which their in vivo therapeutic or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. Also disclosed are "chimeric" antibodies in which a portion of the heavy or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, such as an Fv, Fab, Fab', or other antigen-binding portion of an antibody, can be accomplished using routine techniques known in the art. For instance, digestion can be performed using papain. Examples of papain digestion are described in WO 94/29348 published Dec. 22, 1994 and U.S. Pat. No. 4,342,566 which is hereby incorporated by reference in its entirety for its teaching of papain digestion of antibodies to prepare monovalent antibodies. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.,* 147(1):86-95, 1991). Human antibodies (and fragments thereof) can also be produced using phage display libraries (Hoogenboom et al., *J. Mol. Biol.,* 227:381, 1991; Marks et al., *J. Mol. Biol.,* 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Optionally, the disclosed human antibodies can be made from memory B cells using a method for Epstein-Barr virus transformation of human B cells. (See, e.g., Triaggiai et al., An efficient method to make human monoclonal antibodies from memory B cells: potent neutralization of SARS coronavirus, Nat Med. 2004 August; 10(8):871-5. (2004)), which is herein incorporated by reference in its entirety for its teaching of a method to make human monoclonal antibodies from memory B cells). In short, memory B cells from a subject who has survived a natural infection are isolated and immortalized with EBV in the presence of irradiated mononuclear cells and a CpG oligonucleotide that acts as a polyclonal activator of memory B cells. The memory B cells are cultured and analyzed for the presence of specific antibodies. EBV-B cells from the culture producing the antibodies of the desired specificity are then cloned by limiting dilution in the presence of irradiated mononuclear cells, with the addition of CpG 2006 to increase cloning efficiency, and cultured. After culture of the EBV-B cells, monoclonal antibodies can be isolated. Such a method offers (1) antibodies that are produced by immortalization of memory B lymphocytes which are stable over a lifetime and can easily be isolated from peripheral blood and (2) the antibodies isolated from a primed natural host who has survived a natural infection, thus eliminating the need for immunization of experimental animals, which may show different susceptibility and, therefore, different immune responses.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature,* 321:522-525 (1986), Reichmann et al., *Nature,* 332:323-327 (1988), and Presta, *Curr. Opin. Struct. Biol.,* 2:593-596 (1992)).

Methods for humanizing non-human antibodies are well known in the art. For example, humanized antibodies can be generated according to the methods of Winter and co-workers (Jones et al., *Nature,* 321:522-525 (1986), Riechmann et al., *Nature,* 332:323-327 (1988), Verhoeyen et al., *Science,* 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

The antibodies disclosed herein can also be administered to a subject. Nucleic acid approaches for antibody delivery also exist. The broadly neutralizing antibodies to the polypeptides disclosed herein and antibody fragments can also be administered to subjects or subjects as a nucleic acid preparation (e.g., DNA or RNA) that encodes the antibody or antibody fragment, such that the subject's own cells take up the nucleic acid and produce and secrete the encoded antibody or antibody fragment.

Disclosed herein are polynucleotide, polypeptide, antibody, T-cell, TCR, or APC compositions in pharmaceutically-acceptable carriers for administration to a cell or a subject, either alone, or in combination with one or more other modalities of therapy. For example, disclosed herein is a composition comprising a physiologically acceptable carrier and a polypeptide as described herein. Such compositions can be administered in vivo. By "pharmaceutically acceptable" is meant a material that is not biologically or otherwise undesirable, i.e., the material may be administered to a subject, along with the polypeptide, antibody, polynucleotide or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the inflammatory disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated herein by reference in its entirety for its teaching of an approach for parenteral administration.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)), all of which are herein incorporated by reference in their entirety for their taching of the same. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carriers include, but are not limited to, sterile water, saline, Ringer's solution, dextrose solution, and buffered solutions at physiological pH. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the polynucleotide, polypeptide, antibody, T-cell, TCR, or APC compositions disclosed herein. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Also disclosed are illustrative immunogenic compositions, e.g., vaccine compositions, that comprise DNA encoding one or more of the polypeptides as described above, such that the polypeptide is generated in situ. Numerous gene delivery techniques are well known in the art, such as those described by Rolland, Crit. Rev. Therap. Drug Carrier Systems 15:143-198, 1998, and references cited therein, all of which are herein incorporated by reference in their entirety for their teaching of gene delivery techniques. Appropriate polynucleotide expression systems contain the necessary regulatory DNA regulatory sequences for expression in a subject (such as a suitable promoter and terminating signal). Alternatively, bacterial delivery systems may involve the administration of a bacterium (such as *Bacillus*-Calmette-Guerrin) that expresses an immunogenic portion of the polypeptide on its cell surface or secretes such an epitope.

Additionally, the pharmaceutical compositions described herein can comprise one or more immunostimulants in addition to the polynucleotide, polypeptide, antibody, T-cell, TCR, or APC compositions of this invention. An immunostimulant refers to essentially any substance that enhances or potentiates an immune response (antibody or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Rahway, N.J.); AS-2 (GlaxoSmithKline, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

The adjuvant composition can be a composition that induces an anti-inflammatory immune response (antibody or cell-mediated). Accordingly, high levels of anti-inflammatory cytokines (anti-inflammatory cytokines may include, but are not limited to, interleukin 4 (IL-4), interleukin 5 (IL-5), interleukin 10 (IL-10), and transforming growth factor beta (TGFβ). Optionally, an anti-inflammatory response would be mediated by CD4+ T helper cells. Bacterial flagellin has been shown to have adjuvant activity (McSorley et al., J. Immunol. 169:3914-19, 2002). Also disclosed are polypeptide sequences that encode flagellin proteins that can be used in adjuvant compositions.

Optionally, the adjuvants used in conjunction with the compositions of the present invention increase lipopolysaccharide (LPS) responsiveness. Illustrative adjuvants include but are not limited to, monophosphoryl lipid A (MPL), aminoalkyl glucosaminide 4-phosphates (AGPs), including, but not limited to RC-512, RC-522, RC-527, RC-529, RC-544, and RC-560 (Corixa, Hamilton, Mont.) and other AGPs such as those described in pending U.S. patent application Ser. Nos. 08/853,826 and 09/074,720, the disclosures of which are incorporated herein by reference in their entireties.

In addition, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a subject will support an immune response that includes Th1- and Th2-type responses. Optionally, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989, which is hereby incorporated by reference for its teaching of families of cytokines. The level of Th2-type cytokines can increase to a greater extent than the level of Th1-type cytokines.

Certain adjuvants for eliciting a predominantly Th1-type response include, for example, a combination of monophosphoryl lipid A, preferably 3-de-O-acylated monophosphoryl lipid A, together with an aluminum salt adjuvants are available from Corixa Corporation (Seattle, Wash.; see, for example, U.S. Pat. Nos. 4,436,727; 4,877,611; 4,866,034 and 4,912,094, which are hereby incorporated by reference for their teaching of the same). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other formulations can include more than one saponin in the adjuvant combinations of the present invention, for example combinations of at least two of the following group comprising QS21, QS7, Quil A, β-escin, or digitonin.

Saponin formulations can also be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins can also be formulated in the presence of cholesterol to form particulate structures such as liposomes or immune-stimulating complexes (ISCOMs). Furthermore, the saponins may be formulated together with a polyoxyethylene ether or ester, in either a non-particulate solution or suspension, or in a particulate structure such as a paucilamelar liposome or ISCOM. The saponins can also be formulated with excipients such as CARBOPOL™ (Noveon, Cleveland, Ohio) to increase viscosity, or may be formulated in a dry powder form with a powder excipient such as lactose.

Optionally, the adjuvant system includes the combination of a monophosphoryl lipid A and a saponin derivative, such as the combination of QS21 and 3D-MPL. adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Optionally the formulation additionally comprises an oil in water emulsion and tocopherol.

Additional illustrative adjuvants for use in the pharmaceutical compositions of the invention include Montamide ISA 720 (Seppic, France), SAF (Chiron, Calif., United States), ISCOMS (CSL), MF-59 (Chiron), the SBAS series of adjuvants (e.g., SBAS-2 or SBAS-4, available from GlaxoSmithKline, Philadelphia, Pa.), Detox (ENHANZYN™) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the subject, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as an antibody, for treating, inhibiting, or preventing an immune-mediated inflammatory disease, the efficacy of the therapeutic antibody can be assessed in various ways well known to the skilled practitioner. For instance, one of ordinary skill in the art will understand that a composition, such as an antibody, disclosed herein is efficacious in treating or inhibiting an immune-mediated inflammatory disease in a subject by observing that the composition reduces inflammation or prevents a further increase in inflammation.

The compositions that inhibit inflammatory interactions disclosed herein may be administered prophylactically to subjects or subjects who are at risk for an immune-mediated inflammatory disease. The disclosed compositions and methods can also be used for example as tools to isolate and test new drug candidates for a variety of immune-mediated inflammatory diseases.

Also disclosed are methods of making antigen-presenting cell comprising pulsing antigen-presenting cells with at least one of the polypeptides disclosed herein, under conditions suitable for blocking the maturation of the antigen-presenting cells. Also disclosed are isolated antigen-presenting population, comprising antigen-presenting cells prepared using the disclosed methods of making an antigen-presenting cell.

Antigen presenting cells (APCs) include, but are not limited to dendritic cells, macrophages, B cells, monocytes and other cells that may be engineered to be efficient APCs. Such cells can, but need not, be genetically modified to increase the capacity for presenting the antigen, to improve activation or maintenance of a T cell response, to have anti-bacterial effects per se or to be immunologically compatible with the receiver (i.e., matched HLA haplotype). APCs can generally be isolated from any of a variety of biological fluids and organs, including bacterial and peribacterial tissues, and may be autologous, allogeneic, syngeneic or xenogeneic cells.

Optionally, the methods use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic antibacterial immunity (see Timmerman and Levy, Ann. Rev. Med. 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells can be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors can be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs can be transfected with a polynucleotide of the invention (or portion or other variant thereof) such that the encoded polypeptide, or an immunogenic portion thereof, is expressed on the cell surface. Such transfection can take place in vitro or ex vivo, and a pharmaceutical composition comprising such transfected cells may then be used for therapeutic purposes, as described herein. Alternatively, a gene delivery vehicle that targets a dendritic or other antigen presenting cell may be administered to a subject, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997, which are both hereby incorporated by reference in their entirety for their teaching of methods for transfecting dendritic cells in vivo and ex vivo. Antigen loading of dendritic cells can be achieved by incubating dendritic cells or progenitor cells with the bacterial polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Also disclosed herein are methods of stimulating or expanding T cells specific for an enteric bacterial protein. Specifically, T cells are stimulated with a polypeptide, polynucleotide encoding a polypeptide or an antigen presenting cell (APC) that expresses such a polypeptide. Such stimulation is performed under conditions and for a time sufficient to permit the generation of T cells that are specific for the polypeptide of interest. Optionally, a bacterial polypeptide or polynucleotide of the invention is present within a delivery vehicle, such as a microsphere, to facilitate the generation of specific T cells. For example, disclosed is d method of stimulating or expanding T cells specific for an enteric bacterial protein, comprising contacting T cells with at least one of the disclosed polypeptides; or contacting T cells with one or more antigen-presenting cells; wherein the antigen presenting cells have been pulsed with at least one of the disclosed polypeptides, wherein the contacting step is performed under conditions and for a time sufficient for stimulation or expansion of the T cells. The T-cell contacting step can be performed in vitro, ex vivo, or in vivo using standard procedures. For example, T cells may be isolated from biopsies, bone marrow, peripheral blood, or a fraction of bone marrow or peripheral blood of a subject, using a commercially available cell separation system, such as the ISOLEX™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). T cells can also be isolated from intraepithelial lymphocytes (IEL) or lamina propria lymphocyte (LPL) samples originating from colon biopsies. Individuals with skill in the art will readily recognize that there numerous methodologies for isolating IEL and LPL (for example, methods described in Christ, A. D., S. P. Colgan, S. P. Balk, R. S. Blumberg. 1997. Immunol. Lett. 58:159; Boll G, Reimann J. Scand J Immunol 1995 August; 42(2):191-201, all of which are hereby incorporated by reference in their entirety for their teachings of methodologies for isolating IEL and LPL). In certain aspects, T cells may be derived from related or unrelated humans, non-human mammals, cell lines or cultures.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis or proliferation, compared to negative controls, indicates T cell specificity. Such assays may be performed, for example, as described in Chen et al., Cancer Res. 54:1065-1070, (1994), which is hereby incorporated by reference in its entirety for its teachings of assays for evaluating T cell specificity. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a bacterial polypeptide (100 ng/ml-100 µg/ml, preferably 200 ng/ml-25 µg/ml) for 3-7 days will typically result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ.) is indicative of T cell activation (see Coligan et al., Current Protocols in Immunology, vol. 1, Wiley Interscience (Greene 1998)). T cells that have been activated in response to a bacterial polypeptide, polynucleotide or polypeptide-expressing APC may be $CD4^+$ or $CD8^+$. Bacterial polypeptide-specific T cells may be expanded using standard techniques. Within preferred embodiments, the T cells are derived from a subject, a related donor or an unrelated donor, and are administered to the subject following stimulation and expansion.

For therapeutic purposes, $CD4^+$ or $CD8^+$ T cells that proliferate in response to a bacterial polypeptide, polynucleotide or APC can be expanded in number either in vitro or in vivo. Proliferation of such T cells in vitro may be accomplished in a variety of ways. For example, the T cells can be re-exposed to a bacterial polypeptide, or a short peptide corresponding to an immunogenic portion of such a polypeptide, with or without the addition of T cell growth factors, such as interleukin-2, or stimulator cells that synthesize a bacterial polypeptide. Alternatively, one or more T cells that proliferate in the presence of the bacterial polypeptide can be expanded in number by cloning. Methods for cloning cells are well known in the art and include limiting dilution.

In certain embodiments, T cells that produce anti-inflammatory cytokines may be desirable. Such cytokines may include, but are not limited to, interleukin-10 (IL-10), interferon-γ (IFN-γ), interleukin 4 (IL-4), transforming growth factor beta (TGFβ). In certain embodiments, an anti-inflammatory response is mediated by $CD4^+$ T helper cells.

Also disclosed are methods of making T regulatory cells, isolated T regulatory cells made by the methods, therapeutic uses of the T regulatory cells, methods of promoting tolerization in a subject comprising administering to the subject the T regulatory cells, and compositions comprising the T regulatory cells and an immunostimulant. For example, disclosed is a method of making T regulatory cells comprising contacting T cells with one or more of the antigen-presenting cells made by the disclosed method herein under conditions and for a time sufficient for tolerizing the T cells, wherein the tolerized T cells are T regulatory cells. The T-cell contacting step can be performed in vitro, ex vivo, or in vivo using standard procedures as described herein. Optionally, the T regulatory cells can be CD4+ or can mediate a decrease in inflammation in the colon. T regulatory cells can be made by the methods described in Example 2 below and as described in Cong et al. (Cong et al., CD4+ T cells reactive to enteric bacterial antigens in spontaneously colitic C3H/HeJBir mice: increased T helper cell type I response and ability to transfer disease. Journal of Experimental Medicine 187:855 (1998) which is herein incorporated by reference in its entirety for at least its teaching of making T regulatory cells.

Also disclosed are methods of treating a subject with an immune-mediated inflammatory disease comprising administering to a subject T regulatory cells made by the methods disclosed herein. Also disclosed are methods of treating a subject with an immune-mediated inflammatory disease, wherein an immune response would be anti-inflammatory in nature. Also disclosed are methods of stimulating an immune response in a subject. For example, disclosed is a method, of stimulating an immune response in a subject comprising administering to the subject an isolated polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82.

Immunologic approaches to IBD therapy are based on the recognition that IBD represents an "abnormal" mucosal immune response to bacteria within the lumen of the gastrointestinal tract. The precise molecular nature of the bacterial antigen(s) recognized by the immune system has not been described.

Also disclosed are methods of promoting tolerization in a subject comprising administering to the subject T regulatory cells made by the methods disclosed herein. Inflammatory disease immunotherapy generally focuses on inducing humoral immune responses, cellular immune responses, or both, with the goal of inducing tolerance to a particular enteric bacterial antigen, thereby leading to a decrease in inflammation. Specifically disclosed is a method of promoting tolerization in a subject comprising (a) isolating the pulsed antigen-presenting cells made by the methods disclosed herein and (b) administering the isolated pulsed antigen-presenting cells to the subject. Also disclosed is a method of promoting tolerization in a subject comprising administering both T regulatory cells prepared using the methods disclosed herein and antigen-presenting cells made by pulsing the antigen-presenting cells with at least one of the polypeptides disclosed herein, under conditions suitable for blocking the maturation of the antigen-presenting cells. Also disclosed is a method for inducing such T regulatory cells in vivo by administering a bacterial antigen along with agents that prevent maturation of dendritic cells in vivo.

Moreover, induction of $CD4^+$ T helper cells is necessary in order to secondarily induce either antibodies or cytotoxic $CD8^+$ T cells. Polypeptide antigens of immune-mediated inflammatory disease-associated bacteria offer a powerful approach for inducing anti-inflammatory immune responses that either prevent or ameliorate an aberrant immune response to bacterial antigens associated with immune-mediated inflammatory diseases and are an important aspect of the present invention.

Optionally, the pharmaceutical compositions described herein may be used to stimulate an immune response against bacterial antigens associated with immune-mediated inflammatory diseases. The induced immune response comprises antibodies that block the interaction of a bacterial antigen with a host receptor. Optionally, antibodies induced by the compositions of the present invention block the interaction between flagellin and TLR5, thereby ameliorating the pro-inflammatory cascade initiated by NF-κβ activation. Alternatively, the compositions of the present invention can induce antibodies that stimulate responsiveness to LPS that ameliorated the hypo-responsiveness in individuals with Nod2 gene mutation associated with IBD.

Also disclosed are methods of treating a subject with an immune-mediated inflammatory disease using immunotherapy techniques, wherein immunotherapy may be active immunotherapy, in which treatment relies on the in vivo stimulation of the endogenous host immune system to react against bacteria with the administration of immune response-modifying agents or immunomodulators (such as polypeptides and polynucleotides as provided herein). Also disclosed are methods of decreasing gastrointestinal inflammation associated with inflammatory bowel disease in a subject. For example, disclosed is a method of decreasing gastrointestinal inflammation associated with inflammatory bowel disease in a subject; comprising administering to said subject an isolated polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82.

Also disclosed are methods of treating a subject with an immune-mediated inflammatory disease, wherein immunotherapy may be passive immunotherapy, in which treatment involves the delivery of agents with established antibacterial immune reactivity (such as effector cells or antibodies) that can directly or indirectly mediate antibacterial effects and does not necessarily depend on an intact host immune system. Examples of effector cells include T cells as discussed above, T lymphocytes (such as $CD8^+$ cytotoxic T lymphocytes and $CD4^+$ T-helper lymphocytes), killer cells (such as Natural Killer cells and lymphokine-activated killer cells), B cells and antigen-presenting cells (such as dendritic cells and macrophages) expressing a polypeptide provided herein. For example, disclosed is a method of treating a subject with an immune-mediated inflammatory disease comprising administering to a subject T regulatory cells made by the methods disclosed herein.

Also disclosed is a method of stimulating or expanding B cells specific for an enteric bacterial polypeptide. For example, disclosed is a method of stimulating or expanding B cells specific for an enteric bacterial protein, comprising contacting B cells with at least one isolated polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82, wherein the antigen presenting cells have been pulsed with at least one isolated polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82; wherein the contacting step is under conditions and for a time sufficient for stimulation or expansion of the B cells.

Also disclosed is a method of stimulating or expanding B cells specific for an enteric bacterial protein, comprising contacting B cells with one or more antigen-presenting cells, wherein the antigen presenting cells have been pulsed with at least one isolated polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82; wherein the contacting step is under conditions and for a time sufficient for stimulation or expansion of the B cells.

Optionally, the methods can further comprise isolating a population of the stimulated or expanded B cells, and immortalizing the B cells with Epstein-Barr Virus (EBV) in the presence of irradiated mononuclear cells and a polyclonal B cell activator. Examples of polyclonal B cell activators include, but are not limited to a CpG oligonucleotide, Pokeweed mitogen, and *Staphylococcus aureus* Cowan (SAC), alone or in combination as described by Crotty, et. al. (J. Immunological Methods 286: 111, 2004), which is hereby incorporated by reference in its entirety for its teaching of polyclonal B cell activators. Also disclosed are isolated B cell populations, comprising B cells prepared by the methods disclosed herein.

Also disclosed are methods of making antibodies specific to one or more of the isolated polypeptides encoded by a nucleotide sequence selected from the group consisting of SEQ ID NOs: 1-21, 23, 25, 27, 29, 31, 33, 35, 37, 39, 41, 43, 45, 47, 49, 80 or 82 comprising contacting B cells with the polypeptide; under conditions and for a time sufficient for stimulation or expansion of the B cells, isolating the B cells, immortalizing B cells with EBV in the presence of irradiated mononuclear cells and a polyclonal B cell activator, culturing the immortalized B cells under conditions and for a time sufficient for expansion of the immortalized B cells and production of antibodies.

Also disclosed are methods of making antibodies specific to one or more of the isolated polypeptides encoded by a nucleotide sequence selected from the group consisting of SEQ ID NOs: 1-21, 23, 25, 27, 29, 31, 33, 35, 37, 39, 41, 43, 45, 47, 49, 80 or 82 comprising contacting B cells with one or more antigen-presenting cells, wherein the antigen presenting cells have been pulsed with at least one of the polypeptides of the invention, under conditions and for a time sufficient for stimulation or expansion of the B cells, isolating the B cells, immortalizing B cells with EBV in the presence of irradiated mononuclear cells and a polyclonal B cell activator, culturing the immortalized B cells under conditions and for a time sufficient for expansion of the immortalized B cells and production of antibodies.

T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Disclosed are methods of detecting the presence of an immune-mediated inflammatory disease in a subject. There are a variety of assay formats known to those of ordinary skill in the art for using a binding agent to detect polypeptide markers in a sample. See, e.g., Harlow and Lane, Antibodies: A Laboratory Manual, Cold Spring Harbor Laboratory, 1988. For example, disclosed is a method of detecting the presence of an immune-mediated inflammatory disease in a subject, comprising the steps of (a) obtaining a biological sample from the subject, wherein said biological sample comprises antibodies; (b) contacting the biological sample with a polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82; (c) detecting in the sample an amount of antibody that binds to the polypeptide; and (d) comparing the amount of bound antibody to a control value, the amount corresponding to a control value correlating with the presence of immune-mediated inflammatory disease indicates the presence of immune-mediated inflammatory disease in the subject and the amount corresponding to a control value correlating with the absence of immune-mediated inflammatory disease indicates the absence of immune-mediated inflammatory disease in the subject.

Also disclosed is method of detecting the presence of an immune-mediated inflammatory disease in a subject, comprising the steps of: (a) obtaining a biological sample from said subject, wherein said biological sample comprises sample polynucleotides of the subject; (b) contacting said sample with at least one test polynucleotide, wherein the test polynucleotide is an isolated polynucleotide comprising a sequence selected from the group consisting of SEQ ID NOs:

1-21, 23, 25, 27, 29, 31, 33, 35, 37, 39, 41, 43, 45, 47, 49, 80 or 82 and complements thereof; (c) detecting in the sample an amount of the sample polynucleotide that selectively hybridizes under stringent conditions to the test polynucleotide; and (d) comparing the amount of hybridizing polynucleotide to a control value, the amount corresponding to a control value correlated with the presence of an immune-mediated inflammatory disease indicates the presence of an immune-mediated inflammatory disease in the subject and wherein the amount corresponding to a control value correlated with the absence of an immune-mediated inflammatory disease indicates the absence of an immune-mediated inflammatory disease in the subject. The biological sample obtained from the subject can be sera, stool, tissue or other material obtained by colonoscopy, ileoscopy, esophagogastroduodenoscopy (EGP), or surgery.

Also disclosed are methods of detecting the presence of selected bacterial antigens in a biological sample. For example, disclosed is a method of detecting the presence of selected bacterial antigens in a biological sample comprising the steps of: (a) contacting said biological sample with at least one isolated polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82 under conditions and for a time sufficient for stimulation or expansion of T cells; (b) detecting in the sample the magnitude of said stimulation or expansion of T cells; and (c) comparing the magnitude of said stimulation or expansion to a control value, an increase in the magnitude of stimulation or expansion compared to control indicating the presence of bacterial antigens. Also disclosed is a method of detecting the presence of selected bacterial antigens in a biological sample comprising the steps of: (a) contacting said biological sample with at least one isolated polynucleotide comprising a sequence selected from the group consisting of SEQ ID NOs: 1-21, 23, 25, 27, 29, 31, 33, 35, 37, 39, 41, 43, 45, 47, 49, 80 or 82 and complements thereof under conditions and for a time sufficient for stimulation or expansion of T cells; (b) detecting in the sample the magnitude of stimulation or expansion of T cells; and (c) comparing the magnitude of said stimulation or expansion to a control value, an increase in the magnitude of stimulation or expansion compared to control indicating the presence of bacterial antigens.

Also disclosed is a method of detecting the presence of selected bacterial antigens in a biological sample comprising the steps of: (a) contacting said biological sample with one or more antigen-presenting cells that express a polynucleotide comprising a sequence selected from the group consisting of SEQ ID NOs: 1-21, 23, 25, 27, 29, 31, 33, 35, 37, 39, 41, 43, 45, 47, 49, 80 or 82 and complements thereof under conditions and for a time sufficient for stimulation or expansion of T cells; (b) detecting in the sample the magnitude of said stimulation or expansion of T cells; and (c) comparing the magnitude of said stimulation or expansion to a control value, an increase in the magnitude of stimulation or expansion compared to control indicating the presence of bacterial antigens.

Also disclosed are methods for identifying an immune-mediated inflammatory disease subtypes, including IBD, in a subject. For example, disclosed is a method for identifying immune-mediated inflammatory disease subtype in a subject, comprising: (a) obtaining a biological sample from a subject, wherein the sample comprises one or more of the subject's antibodies; (b) contacting the biological sample with a polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82; (c) detecting in the sample an amount of antibody that binds to the polypeptide; and (d) comparing the amount of bound antibody to a control value associated with the presence or absence of a specific subtype of immune-mediated inflammatory disease, the an amount associated with the presence of a subtype identifying that subtype on the subject and an amount associated with the absence of the subtype indicating a different subtype in the subject.

Also disclosed is a method for identifying an Inflammatory Bowel Disease subtype in a subject, comprising: (a) obtaining a biological sample from a subject, wherein the sample comprises one or more of the subject's antibodies; (b) contacting the biological sample with a polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82; (c) detecting in the sample an amount of antibody that binds to the polypeptide; and (d) comparing the amount of bound antibody to a control value associated with the presence or absence of a specific subtype of Inflammatory Bowel Disease, the an amount associated with the presence of a subtype identifying that subtype on the subject and an amount associated with the absence of the subtype indicating a different subtype in the subject.

Individuals suffering from different immune-mediated inflammatory diseases have different genetic susceptibilities and, in turn, will have different patterns of immune reactivity to environmental antigens such as those of the microbiota. The number of potential antigens of the microbiota is enormous with current estimates of 2-4 million microbial genes, and thus an equal number of potential antigens to which the immune system might respond, being present in an average host. A set of these antigens is sufficient to detect patterns of immune responses that are distinctive to a given immune-mediated inflammatory disease. The antigens of this set are referred to herein as "informative antigens." Informative antigens can be in the form of peptides, such informative antigens can also be referred to as "informative peptides". Measurements of differences in immune reactivity to the informative microbiota antigens is useful as biomarkers for and in screening for susceptibility to immune-mediated inflammatory diseases generally and for screening for a specific immune-mediated inflammatory disease.

Disclosed herein is a method of detecting peptides of the microbiota that are informative reporters for an immune-mediated inflammatory disease, comprising the steps of (a) identifying and cloning of a set of informative genes and their peptides from the microbiota that are bound by serum antibodies of individuals with a given immune-mediated inflammatory disease but not by serum antibodies of healthy individuals who do not have the disease, and (b) identifying the pattern of antibody reactivity to the set of disease informative peptides discovered in step (a), that is present in individuals with the given immune-mediated inflammatory disease but not in healthy controls, or vice versa. For example, in relation to disease susceptibility, detection of a pattern of antibody reactivity to the set of informative antigens in a test subject that is similar to the pattern in individuals with the immune-mediated inflammatory disease would indicate susceptibility of the test subject to that immune-mediated inflammatory disease (or the presence of that disease in the test subject). Conversely, the absence of such a disease-related pattern in a test subject would indicate the lack of susceptibility to or presence of that disease. The term "informative peptides" in this context denotes those peptides that reflect susceptibility, diagnosis, prognosis, or therapeutic utility for a given immune-mediated inflammatory disease.

Furthermore, disclosed herein is a method of detecting a test subject's susceptibility to an immune-mediated inflammatory disease comprising the steps of (a) identifying a pattern of informative antigens reactivity to the serum of a control subject, wherein the control subject has the immune-mediated inflammatory disease or lacks the immune-mediated inflammatory disease, and, (b) comparing the pattern of the informative antigens reactivity to the serum of the test subject to the pattern of informative antigens from step (a), a pattern of informative antigens in the test subject similar to the pattern in the control subject with the immune-mediated inflammatory disease indicating susceptibility of the test subject to the immune-mediated inflammatory disease and a pattern of informative antigens in the test subject similar to the pattern in the control subject lacking the immune-mediated inflammatory disease indicating non-susceptibility of the test subject to the immune-mediated inflammatory disease.

A pattern of informative antigens can be identified in a variety of ways. For example, DNA can be extracted from normal mouse cecal microbiota, sheared, and ligated into lambda phage, creating a microbiota gene library. Serum from individuals with a severe immune-mediated inflammatory disease phenotype can be collected and optionally pooled ("diseased sera"). In addition or alternatively, serum from matched but healthy individuals can be collected and optionally pooled ("healthy sera"). The diseased sera can be used to probe the microbiota library using colony lifts and Western blotting. Positive colonies can be picked and re-probed by colony lifts, again using disease sera and Western blotting. The remaining positive colonies after the second selection can be probed with both the diseased sera pool and the healthy sera pool. Colonies that show some disease specificity, e.g., different reactivity of the diseased sera vs. control sera, can be isolated, the insert cloned, and the sequence determined. These will be termed "informative clones". Informative clones can then be ligated into plasmids and expressed in *E. coli* as fusion proteins with a tag such as polyhistidine to facilitate peptide purification. Purified peptides of the informative clones can then be used in immunoassays against a panel of sera from individuals with an immune-mediated inflammatory disease and a panel of sera from individuals without an immune-mediated inflammatory disease. For example, informative clones can be attached to a solid support for use in an immunoassay. The antibody by the diseased sera to one or more of the informative peptides will provide a disease-related pattern. For example, serum antibodies from an individual with an immune-mediated inflammatory disease can react differently (e.g. higher or lower reactivity) to each informative clone than serum antibodies from an individual without the immune-mediated inflammatory disease. The pattern of reactivity of the diseased sera will serve as a standard to which the pattern of reactivity of a test subject can be compared. For example, in regard to disease susceptibility, if the pattern of reactivity to the informative clones in the test subject is similar to the disease pattern, this will be indicative of the test subject's susceptibility to the immune-mediated inflammatory disease, whereas if the pattern of reactivity to the informative clones in the test subject is similar to the pattern in a healthy control subject lacking the immune-mediated inflammatory disease, this will be indicative of non-susceptibility of the test subject to the immune-mediated inflammatory disease. Once verified, the informative clones can be subsequently used in immunoassays to develop a "immunologic bar code" assay in which the disease-related pattern of reactivity can be detected. The informative clones can be used also in T cell or other immunoassays, for therapeutic purposes, or for any of the other uses claimed in this application. Informative antigens can also be identified as described in U.S. patent application Ser. No. 10/499,857, which is hereby incorporated by reference in its entirety for its teaching of identification of antigens that express different reactivity with sera from an individual with an immune-mediated inflammatory disease than from sera from an individual without an immune-mediated inflammatory disease.

Numerous other assay protocols exist that are suitable for use with the bacterial proteins or binding agents of the present invention. The above descriptions are intended to be exemplary only. For example, it will be apparent to those of ordinary skill in the art that the above protocols may be readily modified to use bacterial polypeptides to detect antibodies that bind to such polypeptides in a biological sample. The detection of such bacterial protein specific antibodies may correlate with the presence of a disease-associated antigen. Additionally, it will be apparent to those of ordinary skill in the art that the above protocols may be readily modified to use the disclosed polypeptides, antibodies or the disclosed polynucleotides in methods itilizing arrays and solid supports, ELISA, fluorescent immunoassays, two-antibody sandwich assays, a flow-through or strip test format, PCR, Real time PCR, Reverse Transcription-PCR (RT-PCR) Techniques for both PCR based assays and hybridization assays are well known in the art (see, for example, Mullis et al., Cold Spring Harbor Symp. Quant. Biol., 51:263, 1987; Erlich ed., PCR Technology, Stockton Press, NY, 1989).

In addition, the compositions described herein may be used as markers for the progression of immune-mediated inflammatory diseases. The assays as described above for the diagnosis of immune-mediated inflammatory diseases may be performed over time, and the change in the level of reactive polypeptide(s) or polynucleotide(s) evaluated. For example, the assays may be performed every 24-72 hours for a period of 6 months to 1 year, and thereafter performed as needed. In general, immune-mediated inflammatory disease is progressing in those subjects in whom the level of polypeptide or polynucleotide detected increases over time. In contrast, immune-mediated inflammatory disease is not progressing when the level of reactive polypeptide or polynucleotide either remains constant or decreases with time. Alternatively, immunoreactivity to a given polypeptide in individuals with an immune-mediated inflammatory disease can correlate with or predict the development of complications, more severe activity of disease.

In addition, the compositions described herein may be used to monitor the level of antibodies specific for or T cell responsiveness to an immune-mediated inflammatory disease-associated bacterial protein as a measure of immune-mediated inflammatory disease progression. In general, immune-mediated inflammatory disease is progressing in those subjects in whom the level of antibodies that bind to a polypeptide or encoded by a polynucleotide described herein, that are detected increases over time. In contrast, immune-mediated inflammatory disease is not progressing when the level of reactive antibodies either remains constant or decreases with time. For example, certain in vivo diagnostic assays may be performed directly on a lesion. One such assay involves contacting cells from a lesion with a binding agent. The bound binding agent may then be detected directly or indirectly via a reporter group. Such binding agents may also be used in histological applications. Alternatively, polynucleotide probes may be used within such applications.

As noted herein, to improve sensitivity, multiple bacterial proteins may be assayed within a given sample. Binding agents specific for different proteins, antibodies, or T cells specific thereto provided herein may be combined within a single assay. Further, multiple primers or probes may be used concurrently. The selection of bacterial proteins may be based on routine experiments to determine combinations that results in optimal sensitivity. In addition, or alternatively, assays for bacterial proteins, antibodies, or T cells specific thereto, provided herein may be combined with assays for other known bacterial antigens or genetic markers such as the NOD2 mutation in subjects with Crohn's disease.

For example, disclosed is a method of monitoring the progression of an immune-mediated inflammatory disease, including IBD, in a subject, comprising the steps of: (a) obtaining a biological sample from the subject, wherein said biological sample comprises antibodies; (b) contacting the biological sample with an isolated polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82; (c) detecting in the sample an amount of antibody that binds to the polypeptide; and (d) repeating steps (a), (b), and (c) using a biological sample obtained from the subject at one or more subsequent points in time; an increase in the amount of bound antibody indicating a progression of an immune-mediated inflammatory disease in the subject.

Also disclosed is a method of monitoring the progression of IBD, in a subject, comprising the steps of: (a) obtaining a biological sample from the subject, wherein said biological sample comprises sample polynucleotides of the subject; (b) contacting the biological sample with at least one test polynucleotide, wherein the test polynucleotide hybridizes under stringent conditions to a polynucleotide comprising a sequence selected from the group consisting of SEQ ID NOs: 1-21, 23, 25, 27, 29, 31, 33, 35, 37, 39, 41, 43, 45, 47, 49, 80 or 82 and complements thereof; (c) detecting in the sample an amount of oligonucleotide that hybridizes to the polynucleotide; and (d) repeating steps (a), (b), and (c) using a biological sample obtained from the subject at one or more subsequent points in time; an increase in the amount of hybridized test polynucleotide indicating a progression of IBD in the subject. The biological sample from the subject can include, but is not limited to a sample of sera, stool, tissue or other material obtained by colonoscopy, ileoscopy, esophagogastroduodenoscopy (EGP), or surgery.

Also disclosed is a method of monitoring the progression of an immune-mediated inflammatory disease in a subject. For example, disclosed is a method of monitoring the progression of an immune-mediated disease in a subject, comprising the steps of: (a) obtaining a biological sample from the subject, wherein said biological sample comprises antibodies; (b) contacting the biological sample with an isolated polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82; (c) detecting in the sample an amount of antibody that binds to the polypeptide; and (d) repeating steps (a), (b), and (c) using a biological sample obtained from the subject at one or more subsequent points in time; an increase in the amount of bound antibody indicating a progression of an immune-mediated inflammatory disease in the subject.

Also disclosed is a method of monitoring the progression of an immune-mediated inflammatory disease in a subject, comprising the steps of: (a) obtaining a biological sample from the subject, wherein said biological sample comprises sample polynucleotides of the subject; (b) contacting the biological sample with at least one test polynucleotide, wherein the test polynucleotide hybridizes under stringent conditions to a polynucleotide comprising a sequence selected from the group consisting of SEQ ID NOs: 1-21, 23, 25, 27, 29, 31, 33, 35, 37; 39, 41, 43, 45, 47, 49, 80 or 82 and complements thereof; (c) detecting in the sample an amount of oligonucleotide that hybridizes to the polynucleotide; and (d) repeating steps (a), (b), and (c) using a biological sample obtained from the subject at one or more subsequent points in time; an increase in the amount of hybridized test polynucleotide indicating a progression of an immune-mediated inflammatory disease in the subject.

Disclosed herein are kits that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed are kits comprising at least one polynucleotide comprising a sequence selected from the group consisting of SEQ ID NOs: 1-21, 23, 25, 27, 29, 31, 33, 35, 37, 39, 41, 43, 45, 47, 49, 80 or 82, complements thereof or fragments thereof. Also disclosed are kits comprising at least one isolated antibody, or antigen-binding fragment thereof, that specifically binds to a polypeptide encoded by a nucleotide sequence selected from the group consisting of SEQ ID NOs: 1-21, 23, 25, 27, 29, 31, 33, 35, 37, 39, 41, 43, 45, 47, 49, 80 or 82. Also disclosed is a kit comprising one or more polypeptides encoded by a nucleotide sequence selected from the group consisting of SEQ ID NOs: 1-21, 23, 25, 27, 29, 31, 33, 35, 37, 39, 41, 43, 45, 47, 49, 80 or 82 immobilized on a solid support.

Also disclosed are kits for use within any of the above diagnostic methods. Such kits typically comprise two or more components necessary for performing a diagnostic assay. Components may be compounds, reagents, containers or equipment. For example, one container within a kit may contain a monoclonal antibody or fragment thereof that specifically binds to a bacterial protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Optionally, a kit may be designed to detect the level of mRNA encoding a bacterial protein in a biological sample. Such kits generally comprise at least one oligonucleotide probe or primer, as described above, that hybridizes to a polynucleotide encoding a bacterial protein. Such an oligonucleotide may be used, for example, within a PCR or hybridization assay. Additional components that may be present within such kits include a second oligonucleotide or a diagnostic reagent or container to facilitate the detection of a polynucleotide encoding a bacterial protein.

Optionally, a kit may be designed to detect the level of antibodies specific for an immune-mediated inflammatory disease-associated bacterial protein in a biological sample.

All references cited herein are each incorporated by reference in their entirety.

EXAMPLES

The following examples are put forth so as to provide those of ordinary skill in the art with a complete disclosure and description of how the compounds, compositions, articles, devices, or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of recombinant intestinal bacterial antigens—Five C3H/HeJ mice were sacrificed. The ceca were removed, opened, suspended in PBS, vortexed several times and the residual tissue was removed. A DNA expression library was generated from these C3H intestinal bacteria via digestion with SMA III restriction enzyme, isolation of 1-2 kb fragments and ligation into the poly-His pQE30 plasmid system (QIAGEN, Valencia, Calif.). Recombinant intestinal bacterial antigens (rIB) were expressed and gene products were screened by SDS-PAGE and immunoblot using mouse IgG1 anti-His (QIAGEN, Valencia, Calif.). Peptides >10 kDa were randomly chosen for further expression and purification on nickel columns (QIAGEN, Valencia, Calif.). Each DNA insert was sequenced and the sequences were compared to known genes listed in GenBank database (www.ncbi.nlm.nih.gov/GenBank/).

Assay of antigen-specific proliferation of CD4$^+$ T cells—Splenic CD4$^+$ T cells were isolated from naïve mice or from immunized mice at day 35 and placed into a cell suspension by straining through a 100 μm sieve. After washing twice, the red blood cells were lysed by TrisHCl. The cells were washed and CD4+ T cells were isolated via positive selection with anti-CD4 magnetic beads (BD Pharmingen, San Diego, Calif.) using the manufacturer's protocol. CD4$^+$ T cells were cultured at $2\times10^5$ cells/well in triplicate in the presence of $2\times10^5$ APCs/well plus 50 μg/ml rIB, or 50 μg/ml OVA. For APCs, splenocytes from C3H/HeJ mice were isolated, irradiated with 30 Gy and added to the T cell culture. Cells were cultured in complete medium containing RPMI 1640, 5% FCS, 10 mM HEPES, 2 mM sodium pyruvate, 2 mM L-glutamine, 100 U/ml penicillin and 100 μg/ml streptomycin for 4 days at 37° C. in 5% $CO_2$ humidified air. For the last 18 h of incubation 0.5 μCi of [$^3$H]thymidine (N.E. Nuclear, Boston, Mass.) was added to each well. The cells were harvested and proliferation was measured in a β scintillation counter.

Generation of bone marrow derived dendritic cells (BMDCs)—Bone marrow cells were isolated by flushing the marrow cavities of mouse femurs with ice-cold RPMI 1640 and gently refluxing the expelled cell plug through a 25-gauge needle to form a single cell suspension. Bone marrow cells from at least 10 femurs isolated from 5 mice were pooled for each experiment, and suspended at $1\times10^6$ cells/ml in complete RPMI 1640 media containing 10% heat-inactivated fetal calf serum (Atlanta Biologicals, Norcross, Ga.), 25 mM HEPES buffer, 2 mM sodium pyruvate (BioWhittaker, Walkersville, Md.), 50 mM 2-mercaptoethanol, 2 mM L-glutamine (Cellgro Mediatech, Herndon, Va.), 100 u/ml Penicillin, and 100 μg/ml Streptomycin (Cellgro Mediatech, Herndon, Va.). The cells were cultured in the presence of 10 ng/ml murine GM-CSF in 24-well plates (Corning, Corning, N.Y.) at 37° C. in 5% $CO_2$ in humid air. Nonadherent cells were collected at day 6 of culture and put back into culture in media containing 10 ng/ml murine GM-CSF. After 3 additional days of culture, nonadherent cells were collected and washed 3 times with fresh media. More than 95% of the non-adherent cells were CD11c$^+$, CD3$^-$, B220$^-$ when checked by flow cytometry. The cells were plated at $1\times10^6$/0.5 ml per well in 48-well plates (Costar, Corning, N.Y.), cultured with various antigens as indicated, and washed.

Isolation of B cells and antibody production in vitro—Human B cells were isolated by positive selection with anti-CD19 using magnetic activated cell sorting (Miltenyi Biotec, Auburn, Calif.). $2\times10^5$ B cells were cultured with $2\times10^5$ non-B cells and stimulated with a mixture of polyclonal activators, including pokeweed mitogen, fixed *Staphylococcus aureus*, Cowan strain (SAC), and phosphothiolated CpG oligonucleotide after the method of Crotty, et. al. (J. Immunol Methods 286: 111, 2004). Six days later, culture supernatants were collected and antigen-specific antibodies of various isotypes measured by ELISA. Memory B cells were collected from the cultures and analyzed by ELISPOT assays for antigen-specific and total IgG- or IgA-producing cells.

Antibody measurement by ELISA—ELISA plates were coated with rIB or other antigens (2 μg/ml in PBS) overnight at 4° C. After washing the plates in PBS, the plates were blocked with PBS containing 1% bovine serum albumin (BSA) and washed again. Serial dilutions of sera were added and the plates incubated for 24 h at 4° C. Plates were washed again in PBS/0.05% Tween. Affinity purified, biotin labeled, goat anti-mouse immunoglobulin G (1:2000) or goat anti-mouse IgA was added for 2 h at room temperature (KPL, Gaithersburg, Md.). After washing, the plates were incubated for one hour with the horse radish peroxidase labeled streptavidin at 1:4000 (ICN Biomedicals, Aurora, Ohio) at room temperature and washed again. The plates were developed by addition of 50 μl TMB substrate (KPL, Gaithersburg, Md.) and the reaction was stopped with 50 μl 1M sulfuric acid. Plates were read by an ELISA reader at 480 nm (Bio-Tek Instruments, Winooski, Vt.).

Generation of PSI-APC Treg cells—BMDC generated from BALB/c mice were treated with 1 mM PSI dissolved in DMSO for 4 hrs and then 5 mg/ml OVA peptide for additional 20 hrs at $1\times10^6$/ml. After washing twice, the pretreated BMDC were added at $1\times10^5$/ml into cultures of $1\times10^6$ freshly isolated CD4$^+$ T cells from DO11.10.RAG2$^{-/-}$ mice. Seven days later, the CD4$^+$ T cells were re-isolated with CD4-magnet beads (Pharmingen, San Diego, Calif.) and used to test for regulatory activity (PSI-APC Treg). Freshly isolated CD4$^+$ T cells from DO11.10.RAG2$^{-/-}$ mice were also cultured with 5 mg/ml OVA peptide-pulsed BMDC as control, and used as memory T cells (Tmem).

Example 2

Preparation of T Reg Cells

Mice—BALB/c mice were obtained from the Jackson Laboratory (Bar Harbor, Me.). DO11.10 and DO11.10.RAG-2$^{-/-}$ OVA TCR transgenic mice were bred in the Animal Facility at the University of Alabama at Birmingham. Female mice of 6 to 12 weeks old were used in these experiments.

Reagents and Materials—Reagents and materials were purchased from the following sources. PSI (benzyloxycarbonyl-isoleucyl-glutamyl(O-tert-butyl)-alanyl-leucinal) (Z-Ile-Glu(OtBu)-Ala-Leu-CHO) was purchased from Calbiochem (San Diego, Calif.). GM-CSF was a gift kindly provided by Dr. Robert Coffman (DNAX, Palo Alto, Calif.). Anti-CD4, CD25, and CTLA-4 mAb were purchased from BD Biosciences (San Diego, Calif.). Anti-GITR and anti-TGFβ were purchased from R&D Systems (Minneapolis, Minn.). Anti-IL-10R1 was a gift from Dr. Kevin Moore (DNAX, Palo Alto, Calif.).

CD4$^+$ T cell purification—CD4$^+$ T cells were isolated by using anti-mouse CD4-magnetic beads (Pharmingen, San Diego, Calif.). Briefly, spleen or MLN cells were washed twice and incubated with anti-CD4-beads at 4° C. for 30 min, and then separated by magnetic field. When checked by flow cytometry, >95% of the cells were CD4$^+$ T cells.

Generation of bone marrow derived dendritic cells (BM-DCs)—Bone marrow cells were isolated by flushing the marrow cavities of mouse femurs with ice-cold RPMI 1640 and gently refluxing the expelled cell plug through a 25-gauge needle to form a single cell suspension (Cong et al., The mucosal adjuvanticity of cholera toxin involves enhancement of costimulatory activity by selective up-regulation of B7.2 expression. Journal of Immunology 159:5301 (1997)). The mucosal adjuvanticity of cholera toxin involves enhancement of costimulatory activity by selective up-regulation of B7.2 expression. Bone marrow cells from at least 10 femurs isolated from 5 mice were pooled for each experiment, and suspended at 1×10$^6$ cells/ml in complete RPMI 1640 media containing 10% heat-inactivated fetal calf serum (Atlanta Biologicals, Norcross, Ga.), 25 mM HEPES buffer, 2 mM sodium pyruvate (BioWhittaker, Walkersville, Md.), 50 mM 2-mercaptoethanol, 2 mM L-glutamine (Cellgro Mediatech, Herndon, Va.), 100 u/ml Penicillin, and 100 mg/ml Streptomycin (Cellgro Mediatech, Herndon, Va.). The cells were cultured in the presence of 20 ng/ml GM-CSF in T-75 flasks (Corning, Corning, N.Y.) at 37° C. in 5% $CO_2$ in humid air. The nonadherent cells were collected at day 6 of culture and put back into culture in media containing 20 ng/ml GM-CSF. After 3 additional days of culture, nonadherent cells were collected and washed 3 times with fresh media. More than 95% of the adherent cells were CD11c$^+$, CD3$^-$, B220$^-$ when checked by flow cytometry. The cells were plated at 1×10$^6$/0.5 ml per well in 48-well plates (Costar, Corning, N.Y.) in the presence of various agents as indicated. After incubation at 37° C. in 5% $CO_2$ and humid air for 24 h, supernatants were collected, centrifuged to remove contaminating cells, and stored at 70° C. until cytokines analysis. Cells were stained for flow cytometric analysis.

Generation of PSI-APC Treg cells—BMDC generated from BALB/c mice were treated with 1 μM PSI dissolved in DMSO for 4 hrs and then 5 μg/ml OVA peptide for additional 20 hrs at 1×10$^6$/ml. After washing twice, the pretreated BMDC were added at 1×10$^5$/ml into cultures of 1×10$^6$ freshly isolated CD4$^+$ T cells from DO11.10.RAG2$^{-/-}$ mice. Seven days later, the CD4$^+$ T cells were re-isolated with CD4-magnet beads (Pharmingen, San Diego, Calif.) and used to test for regulatory activity (PSI-APC Treg). Freshly isolated CD4$^+$ T cells from DO11.10.RAG2$^{-/-}$ mice were also cultured with 5 μg/ml OVA peptide-pulsed BMDC as control, and used as memory T cells (Them).

Generation of a KLH-specific CD4$^+$ T cell line—BALB/c mice were immunized with KLH 100 μg in CFA i.p. twice at day 1 and day 14. The mice were sacrificed 7 days later and splenic CD4$^+$ T cells were isolated and stimulated with KLH-pulsed APC for a week, then restimulated every two weeks for several cycles.

T cell proliferation assay—CD4$^+$ T cells at 1×10$^5$ cells/well were incubated in triplicate in the presence of 4×10$^5$ antigen-pulsed spleen cells as APC in the wells of a 96-well plate at 37° C. in 5% $CO_2$ humidified air. After 4 d of incubation, 0.5 μCi of $^3$H-thymidine was added to each culture for the last 18 hr of the incubation period. The cells were harvested on glass fiber filters on a PHD cell harvested (Cambridge Technology, Watertown, Mass.) and proliferation was assessed as the amount of incorporation of $^3$H-thymidine into cell DNA, as measured by beta scintillation counting of the harvested samples. Data are expressed as CPM±SD.

Cytokine assays—CD4$^+$ T cells were stimulated in the presence of OVA peptide plus irradiated spleen cells as APC. The culture supernatants (SN) were collected at different times and pooled together for assay. SN collected after 24 hr of culture were used for IL-2 assay and SN collected at 72 h of culture were used for IL-10, IL-4, and IFNγ assays. The cytokine content in SN was determined by ELISA as previously described by Cong et al. (Cong et al., CD4+ T cells reactive to enteric bacterial antigens in spontaneously colitic C3H/HeJBir mice: increased T helper cell type 1 response and ability to transfer disease. Journal of Experimental Medicine 187:855 (1998).

Measurement of nuclear NF-κB—BMDC were treated with media alone, 1 μg/ml LPS, or LPS plus 1 μM PSI for 60 min. The nuclear extracts were made by using TransFactor Extraction Kit (Clontech Laboratories, Inc., Palo Alto, Calif.) based on the protocol recommended by the manufacturer. NF-κB p65 was measured by using Mercury TransFactor Kits (Clontech Labs, Inc., Palo Alto, Calif.) according to manufacturer's protocol.

Flow cytometric analysis—After washing in PBS with 0.1% sodium azide plus 2% heat-inactivated newborn calf serum, the cells were incubated with various FITC-, Red 670-, or PE-conjugated mAbs, washed, and fixed in 1% buffered paraformaldehyde. 1.5×10$^5$ stained cells were quantitated using a FACStar flow cytometer (Becton Dickinson, Mountain View, Calif.). A FITC-, or PE-labeled mAb of the same isotype but irrelevant specificity was used as a negative control in all experiments.

Analysis of Foxp3 and indoleamine-2,3-dioxygenase (IDO) mRNA expression—Expression of FoxP3 on T cells was detected using real-time PCR with the primers 5'GGC-CCTTCTCCAGGACAGA3' (SEQ ID NO: 72) and 5'GCT-GATCATGGCTGGGTTGT3' (SEQ ID NO: 73) at a final concentration of 800 nM and a FAM-labeled internal probe 5'ACTTCATGCATCAGCTCTCCACTGTGGAT3' (SEQ ID NO: 74) at a final concentration of 150 nM. As an endogenous reference, β-2 microglobulin was simultaneously measured using primers 5'CCTGCAGAGTTAAGCATGCCAG3' (SEQ ID NO: 75) and 5'TGCTTGATCACATGTCTCGATCC3' (SEQ ID NO: 76) (final concentration 30 nM) and a Texas Red labeled internal probe 5'TGGCCGAGCCCAAGAC-CGTCTAC3' (SEQ ID NO: 77) (final concentration 50 nM). All primers and probes were obtained from Integrated DNA Technologies, Inc. (Coralville, Iowa). Multiplex reactions were performed using Platinum Quantitative PCR SuperMix-UDG (Invitrogen, Carlsbad, Calif.) and amplified with the cycling parameters 50° C. for 2 minutes, 95° C. for 2 minutes and 40 cycles of 95° C. for 15 seconds and 60° C. for 1 minute on a Bio-Rad iCycler (Bio-Rad, Hercules, Calif.).

Transcripts of IDO in DC was measured by RT-PCR with primers 5'GTACATCACCATGGCGTATG3' (SEQ ID NO: 78) and reverse 5'GCTTTCGTCAAGTCTTCATTG3' (SEQ ID NO: 79) at final concentration of 1 nM. RT-PCR conditions used were 48° C. for 45 min, 94° C. for 2 min (1 cycle); 94° C. for 30 s, 58° C. for 1 min, 68° C. for 2 min (35 cycles); and 68° C. for 5 mM (1 cycle). PCR products were fractionated on a 1.5% agarose gel containing ethidium bromide and were visualized by ultraviolet fluorescence. RT-PCR amplification of the murine GAPDH mRNA was performed in parallel.

CFSE labeling and adoptive transfer of DO11.10 transgenic T cells and Treg cells—CFSE in the form of a 5 mM stock solution in DMSO was added to $2\times10^7$ DO11.10 CD4 T cells/ml in a final concentration of 2 µM. The cells were incubated at 37° C. for 10 min and then washed twice with fetal calf serum and twice with culture media.

Adoptive transfer of OVA-specific Th1 cells and induction of colitis—To generate OVA-specific, "pushed" Th1 cells, CD4$^+$ T cells from DO11.10 mice were cultured with 2 µg/ml OVA peptide and 5 µg/ml anti-IL-4 mAb (11B11) and 10 ng/ml IL-12 in the presence of irradiated APC for seven days. OVA-expressing *E. coli* and Tet-expressing *E. coli* were prepared as described previously (Iqbal, N., et al., T helper 1 and T helper 2 cells are pathogenic in an antigen-specific model of colitis. J Exp Med 195:71 (2002)). Briefly, $5\times10^6$ in vitro pushed Th1 cells alone, $5\times10^6$ Th1 cells plus $5\times10^6$ PSI-APC Treg cells, or $5\times10^6$ PSI-APC Treg cells alone were each injected into groups of five BALB.RAG2$^{-/-}$ mice i.v., and the recipients were then given OVA-expressing *E. coli* into the colon. Control BALB.RAG2$^{-/-}$ mice were reconstituted with $5\times10^6$ in vitro pushed Th1 cells and then given Tet-expressing *E. coli* into the colon. Two months later, the mice were sacrificed and histopathology was examined.

Statistical analysis—The results were expressed as the mean±SD. The significance of the difference between means was determined by the Mann-Whitney test, and differences were considered statistically significant at $p<0.05$.

Results

PSI treated APC inhibited T cell proliferation in vitro—PSI-pulsed BMDC stimulated with LPS did not upregulate expression of costimulatory molecules, such as CD40, CD86, and MHC class II, or IL-12p70 cytokine production, whereas IL-10 production was not affected. PSI-pulsed BMDC stimulated by LPS had reduced levels of NF-κB p65 in nuclear extracts compared to control (FIG. 1A). These data confirmed the observation that PSI blocks the maturation of immature to mature DCs.

Figure 1B:
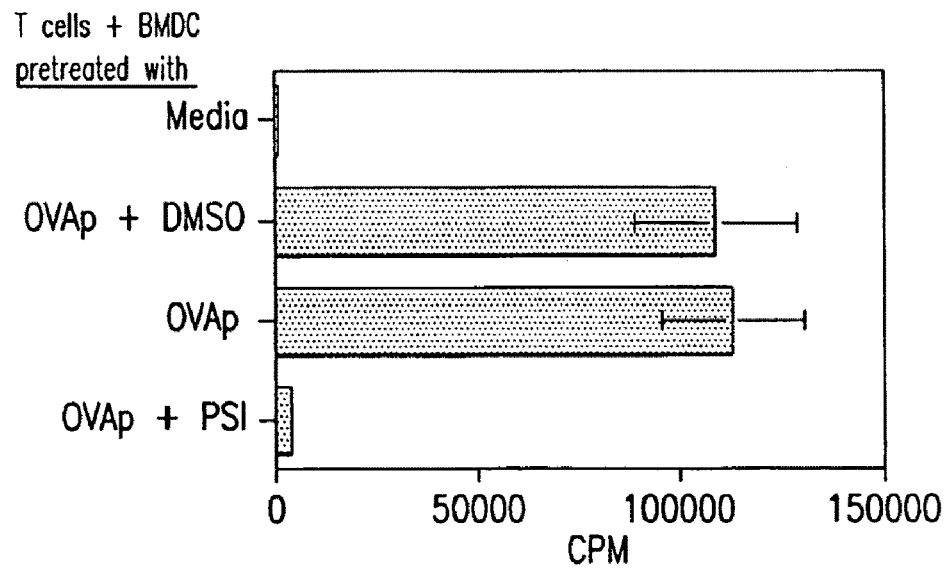

To investigate the ability of PSI-treated DC to present antigen to CD4$^+$ T cells, BMDC of BALB/c mice were pulsed with PSI for 4 hrs and then 5 µg OVA peptide for additional 20 hrs. Then the pretreated BMDC were irradiated and put into culture with naïve DO11:10.RAG2$^{-/-}$ TCR transgenic CD4$^+$ T cells. Naive DO11.10 CD4$^+$ T cells proliferated strongly to stimulation of OVA peptide-pulsed BMDC. However, this T cell response was greatly decreased in cultures with PSI-pretreated, OVA peptide-pulsed BMDC ($p<0.005$, FIG. 1B). BMDC pretreated with solvent DMSO plus OVA peptide had no effect on T cell proliferation (FIG. 1B).

Figure 1C:
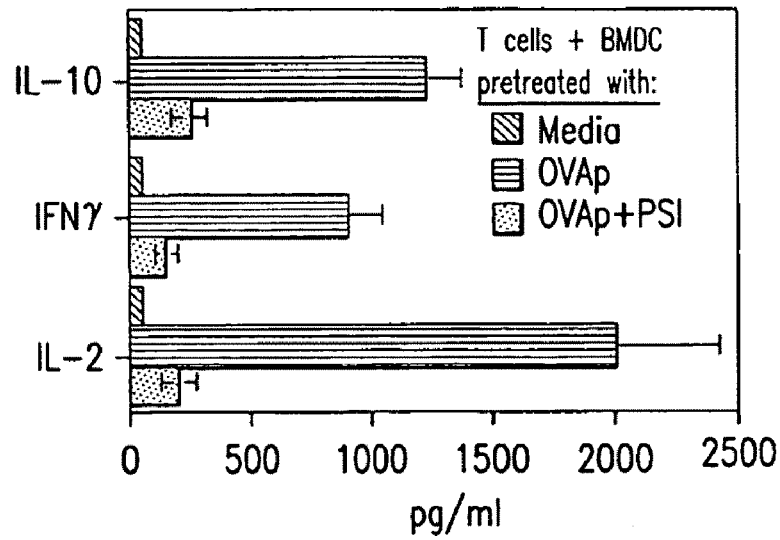

Naïve DO11.10 CD4$^+$ T cells produced high amounts of IL-2 and moderate amounts of IFNα, and IL-10, but no IL-4 upon stimulation of OVA-peptide-pulsed BMDC. Culture with PSI-pretreated, OVA peptide-pulsed BMDC greatly reduced T cell IL-2 (89%), IFNα (81%) and IL-10 production (79%). There was no IL-4 production (FIG. 1C).

Figure 2A:
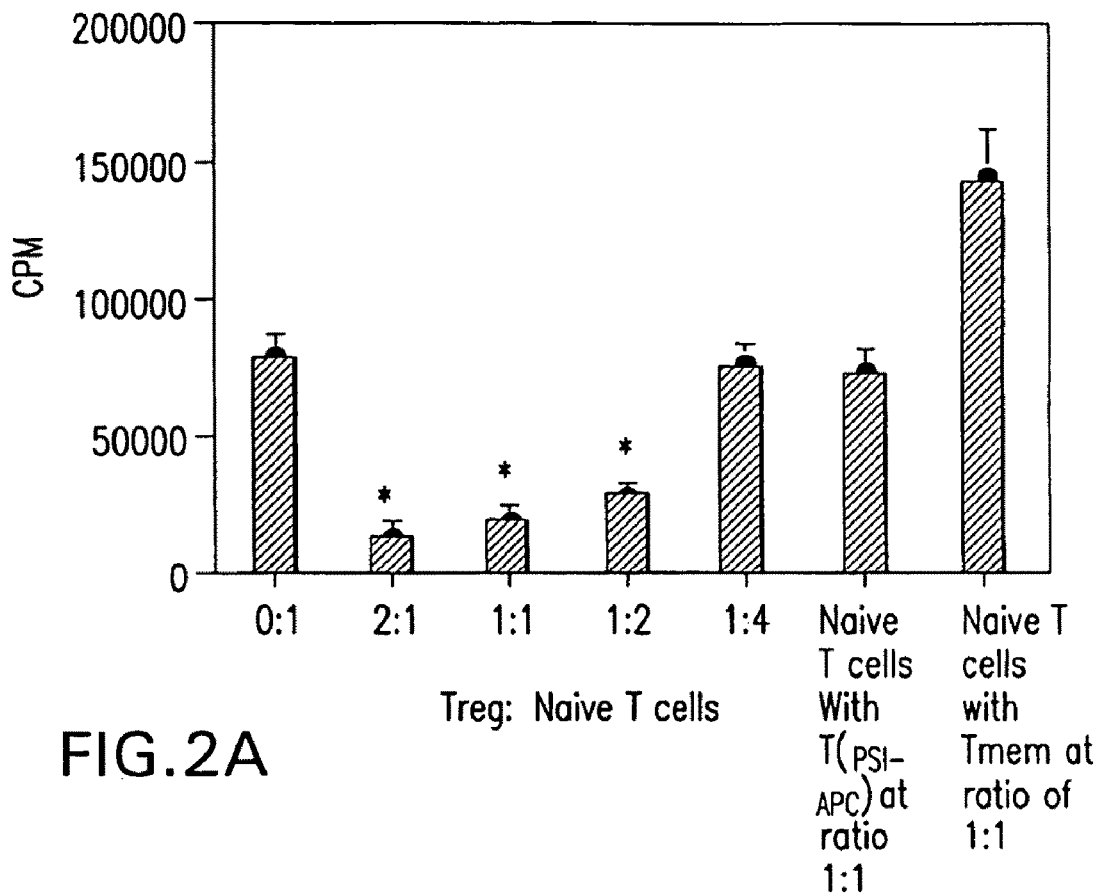
FIG. 2 shows PSI-BMDC generated T cells inhibited naïve and memory T cell responses to antigen stimulation. A. BMDC of BALB/c mice were pulsed with or without 1 μM PSI for 4 hrs, then with 5 μg/ml OVA peptide for an additional 20 hrs, and then $2\times10^4$ pulsed APCs were cultured with $1\times10^5$ CD4$^+$ T cells from DO11.10.RAG2$^{-/-}$ mice. One week later, the T cells were harvested and cultured with naïve CD4$^+$ T cells of DO11.10 mice at various ratios in the presence of $4\times10^5$ fresh OVA-pulsed APC. Naive T cells were also cultured at a 1:1 ratio with T cells that had been incubated with PSI-treated BMDC that were not pulsed with OVA (T(PSI-APC)). $^3$H-TdR was added in the final 18 hrs of 3-day culture. B. PSI-APC cultured T cells were co-cultured with memory DO11.10 CD4$^+$ T cells in the presence of OVA peptide-APC. $^3$H-TdR was added in the final 16 hrs of a 3-day culture. The results were expressed in average of CPM of triplicate+SD. One representative of three experiments is shown. * p<0.05;  p<0.005; * p<0.001 compared to cultures with only naive T cells.

CD4$^+$ T cells induced with PSI-treated BMDC inhibited naïve and memory CD4$^+$ T cell responses—To test whether T cells induced with PSI-treated BMDC have regulatory function, DO11.10.RAG2$^{-/-}$ CD4$^+$ T cells were cultured with BMDC that were pretreated with PSI for 4 hrs and then OVA peptide for additional 20 hrs. CD4$^+$ T cells were harvested 7 d later and re-isolated with anti-CD4-magnetic beads. The cell yield was about 150-20% of the original T cell input. After washing twice, the T cells were added into a second culture with freshly isolated naïve DO11.10 CD4$^+$ T cells at various ratios. As shown in FIG. 2A, CD4$^+$ T cells that had been incubated with PSI- and OVA-pulsed BMDC inhibited naïve T cell proliferation at 2:1 ($p<0.001$), 1:1, ($p<0.005$) and 1:2 ($p<0.05$) ratios of PSI-APC Treg:naïve T cells. At a ratio of 1:4, these T cells did not inhibit naïve T cell response ($p>0.051$). Memory T cells (Tmem, cell yield about 130% of the original T cells) and T cells that had been incubated with PSI-treated BMDC that were not pulsed with OVA (T (PSI-APC) cell, yield about 10% of the original T cells) had little effect on naïve T cell proliferation ($p>0.1$).

Figure 2B:
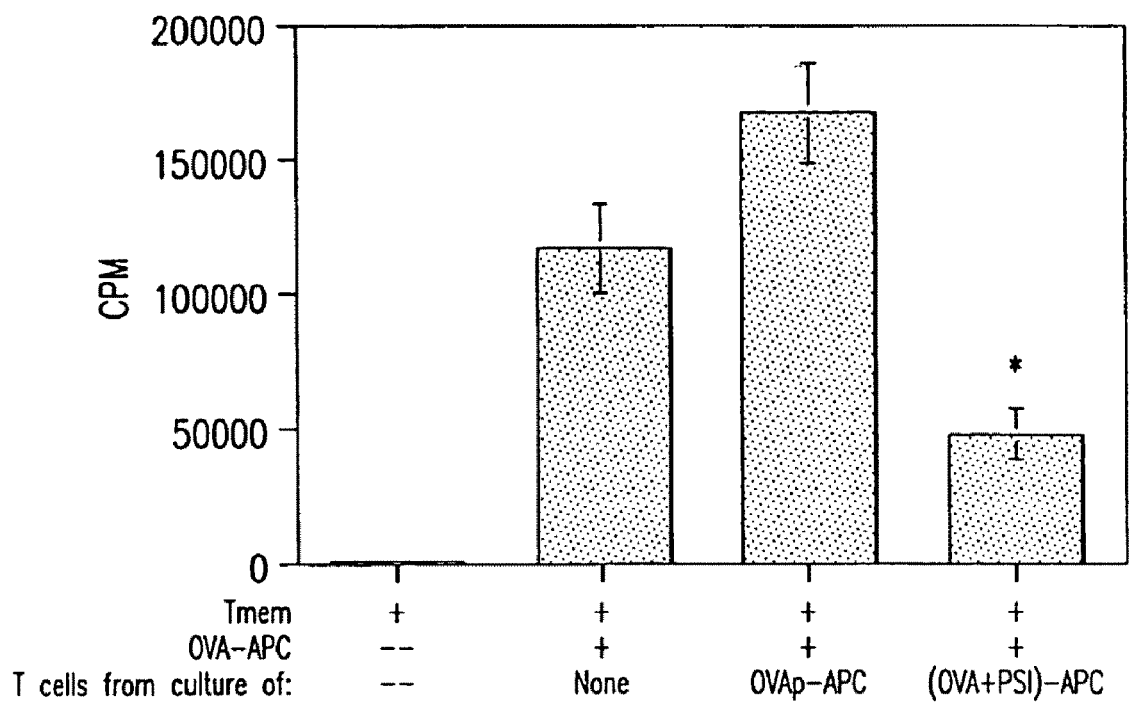

To determine the effects of such Treg cells on memory T cells, memory T cells were generated by culture of DO11.10 CD4$^+$ T cells with OVA peptide in the presence of BMDC for 7 days. These antigen-primed memory CD4$^+$ T cells (Tmem) were then re-stimulated with fresh, OVA peptide-pulsed APCs in the absence or presence of the putative Treg cells. T cell proliferation was measured at day 3 of culture. As shown in FIG. 2B, memory Tmem cells proliferated well to OVA peptide stimulation, but T cells generated with PSI-treated BMDC inhibited Tmem cell proliferation significantly ($p<0.05$) at a 1:1 ratio of Treg:Tmem cells.

To test whether PSI-treated, normal spleen APC could also generate putative regulatory T cells as well as PSI-treated BMDC did, spleen cells of BALB/c mice were treated with 1 µM PSI and OVA peptide as the same fashion. DO11.10.RAG2$^{-/-}$ CD4$^+$ T cells were then cultured with these pretreated-splenic APC for 7 days. DO11.10.RAG2$^{-/-}$ CD4$^+$ T cells that were cultured with PSI and OVA-pulsed splenic APC inhibited both naïve and memory T cell proliferation significantly. These data demonstrated that antigen-pulsed, PSI-treated BMDC and normal spleen APC induced T cells with regulatory function. These regulatory cells are thus denoted as "PSI-APC Treg cells".

Figure 3A:
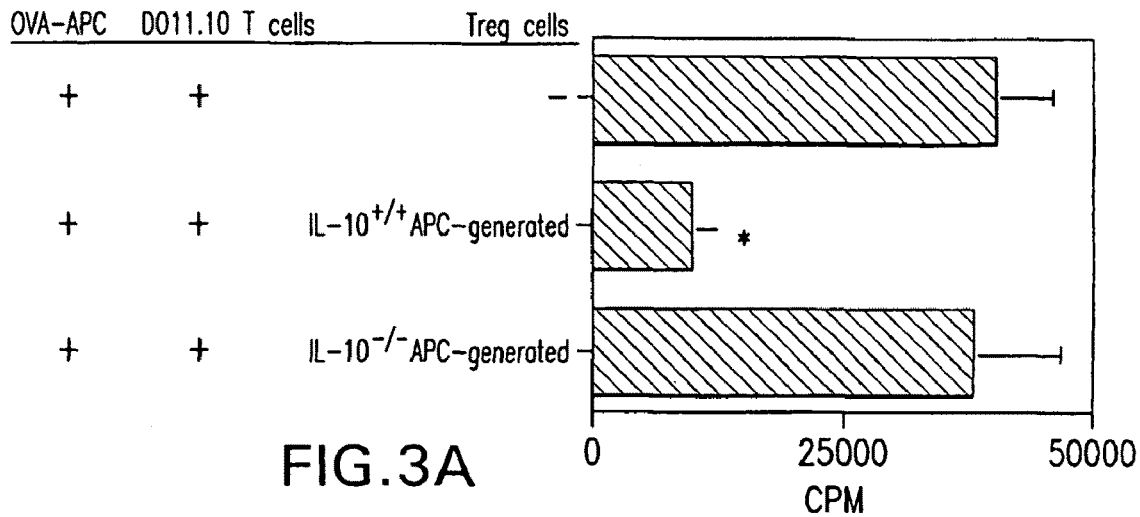
FIG. 3 shows PSI-APC Tregs required IL-10 for their generation and are not derived from C25$^+$ cells, but expressed Foxp3. Spleen cells of wild type or IL-1$^{-/-}$ BALB/c mice were pulsed with 2 μg/ml OVA peptide and 1 μM PSI for 24 hrs, and then $4\times10^5$ pulsed APCs were cultured with $1\times10^5$ CD4$^+$ T cells from DO11.10 mice. One week later, the T cells were harvested and co-cultured with naïve DO11.10 CD4$^+$ T cells in the presence of fresh OVA-pulsed APCs. $^3$H-TdR was added in the final 16 hrs of 3-day culture. B. CD25$^-$ CD4$^+$ T cells and whole CD4$^+$ T cells from DO11.10 mice were cultured with APC that had been pulsed with 2 μg/ml OVA peptide and 1 μM PSI for 24 hrs. 7 d later, these CD4$^+$ T cells were re-isolated and co-cultured with naïve DO11.10 CD4$^+$ T cells in the presence of fresh OVA-pulsed APC. $^3$H-TdR was added in the final 16 hrs of a 3-day culture. The results are expressed as mean CPM of triplicates+SD. *p<0.05 compared to cultures with only naive T cells. C. PSI-APC Treg cell expression of Foxp3. Seven days after cultured with OVA-pulsed APC or OVA-plus PSI-pulsed APCs, DO11.10 CD4$^+$ T cells were lysed and Foxp3 expression was measured by real-time PCR. One representative One representative of three experiments is shown.

Induction of PSI-APC Treg cells required IL-10 production by APCs but not the presence of CD25$^+$ T cells—IL-10 has been implicated as an important differentiating factor for some subtypes of Treg cells. To investigate the role of APC IL-10 in the induction of PSI-APC Treg cells, adherent splenic APCs from wild type or IL-10 deficient BALB/c mice were treated with OVA plus PSI for 24 hrs, and used to generate Treg cells. Treg cells generated by culture with wild type APC with pulsed PSI-OVA peptide inhibited naïve T cell responses to OVA peptide stimulation ($p<0.05$). In contrast, T cells cultured with IL-10$^{-/-}$ APC had no effect on naïve T cell responses to OVA peptide stimulation ($p><0.05$), indicating that generation of PSI-APC Treg cells required IL-10 production by APCs (FIG. 3A).

Figure 3B:
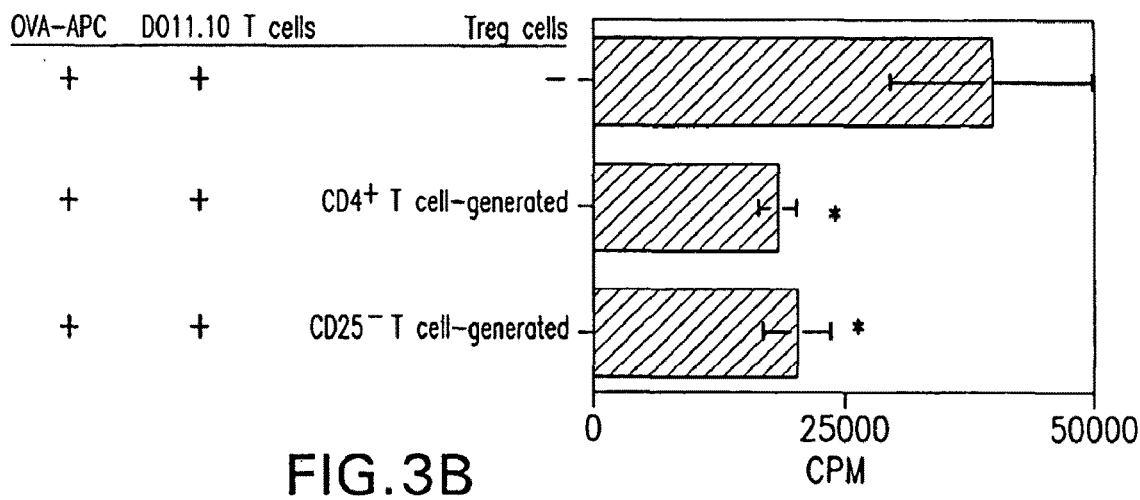

To determine whether CD4$^+$, CD25$^+$ T cells were the precursor of PSI-APC Treg cells, CD25$^+$ T cells were depleted from naïve DO11.10 CD4$^+$ spleen cells by FACS sorting. The remaining CD4$^+$, CD25$^-$ T cells (>99% purity) were cultured with PSI- and OVA-peptide-pulsed APCs for a week, and then their inhibitory function was measured. Unfractionated naive CD4$^+$ T cells were cultured in a similar manner as a positive control. CD4$^+$, CD25$^-$ T cells that were cultured with APCs pretreated with OVA and PSI strongly inhibited naive CD4$^+$ T cell proliferation similar to control unfractionated CD4$^+$ T cells, indicating that PSI-APC Treg could be generated from CD4$^+$, CD25$^-$ T cell fraction, and that CD25$^+$ cells are not required for the generation of PSI-APC Tregs. (See FIG. 3B)

Figure 3C:
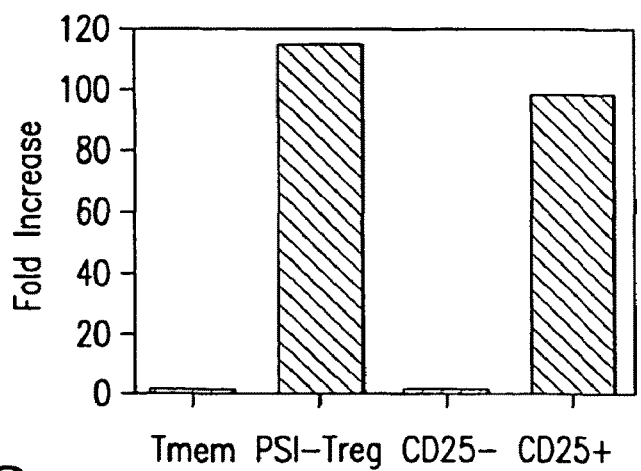

PSI-APC Treg cells express Foxp3—Foxp3 has been shown as a transcription factor specific for CD25 Treg cell development and function (Fontenot, J. D., M. A. Gavin, and A. Y. Rudensky. 2003. Foxp3 programs the development and function of CD4+CD25+ regulatory T cells. Nat Immunol 4:330; Sakaguchi, S. 2003. The origin of FOXP3-expressing CD4+ regulatory T cells: thymus or periphery. J Clin Invest 112:1310; and Hori, S., T. Nomura, and S. Sakaguchi. 2003. Control of regulatory T cell development by the transcription factor Foxp3. Science 299:1057) To determine whether PSI-APC Treg cells express Foxp3, RNA was isolated from PSI-APC Treg cells and memory CD4$^+$ T cells, and Foxp3 expression was measured by real time PCR. CD4$^+$, CD25$^+$ and CD4$^+$, CD25$^-$ T cells served as controls. As shown in FIG. 3C, Foxp3 expression in PSI-APC Treg cells was about 60-fold higher than that in memory CD4$^+$ T cells, similar to the expression found in CD25$^+$ Treg cells.

Activation of PSI-APC Treg cell function was antigen-specific—To investigate the antigen specificity of PSI-APC Treg cell activation, a CD4$^+$ T cell line reactive to KLH was generated, and used as target cells to investigate the antigen specificity of PSI-APC Treg cells. OVA-specific PSI-APC Treg were generated as described above and co-cultured with KLH-specific T cells and APC in the presence of 100 μg/ml of KLH, 2 μg/ml of OVA peptide, or both KLH and OVA peptide. KLH-specific T cells proliferated well in the presence of KLH (cpm 13701±2755). This proliferation was inhibited by OVA-specific PSI-APC Treg cells only in the presence of OVA peptide (cpm 9585±897, p<0.05), but not in its absence (cpm 13963±2137, p>0.05), indicating that these Treg cells require specific antigen signaling through their TCR to activate their regulatory program.

Figure 4A:
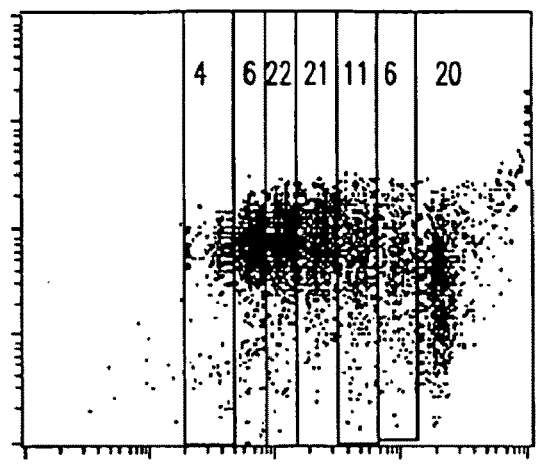
FIG. 4 shows PSI-APC Treg inhibition is not reversed by exogenous IL-2. PSI-APC Tregs were generated as in the legend to FIG. 3. 7 d later the T cells were harvested and co-cultured with CFSE-labeled DO11.10 CD4$^+$ T cells in the presence of OVA-pulsed APCs with or without 100 U/ml IL-2 for 3 days. The cells were harvested and stained with PE-KJ1-26 mAb and analyzed by flow cytometry. One representative of three experiments is shown. The percent of cells present in each cell division are shown at the top of each profile.
Figure 4B:
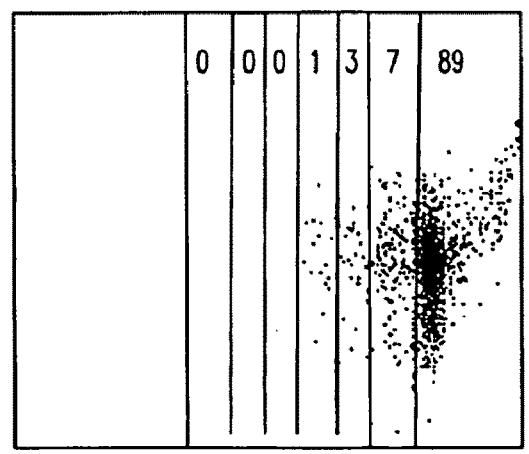
Figure 4C:
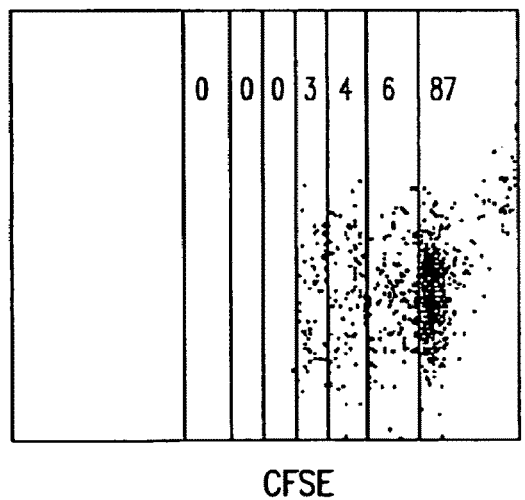

Addition of IL-2 did not reverse Treg cell inhibition—To investigate the effects of IL-2 on the inhibitory activity of PSI-APC induced Treg cells, CFSE-labeled naïve DO11.10 CD4$^+$ T cells were cultured with Treg cells in the presence of OVA-APC with or without high dose of IL-2 (100 U/ml). Three days later, the cells were stained with PE-labeled KJ1-26 antibody for flow cytometric analysis. The KJ1-26$^+$ CFSE-labeled naïve CD4$^+$ T cells proliferated well, with a large fraction of the T cells having 4-6 cell divisions (FIG. 4A). Addition of Treg cells to these cultures greatly inhibited proliferation of OVA-specific CD4$^+$ T cells (89% of cells did not divide compared to 20% in the absence of Treg cells) (FIG. 4B). Addition of IL-2 did not reverse the Treg cell inhibition of cell-cycle progression of naïve CFSE-labeled CD4$^+$ T cells (87% of cells did not divide compared to 89% in the presence of IL-2) (FIG. 4C).

Figure 5A:
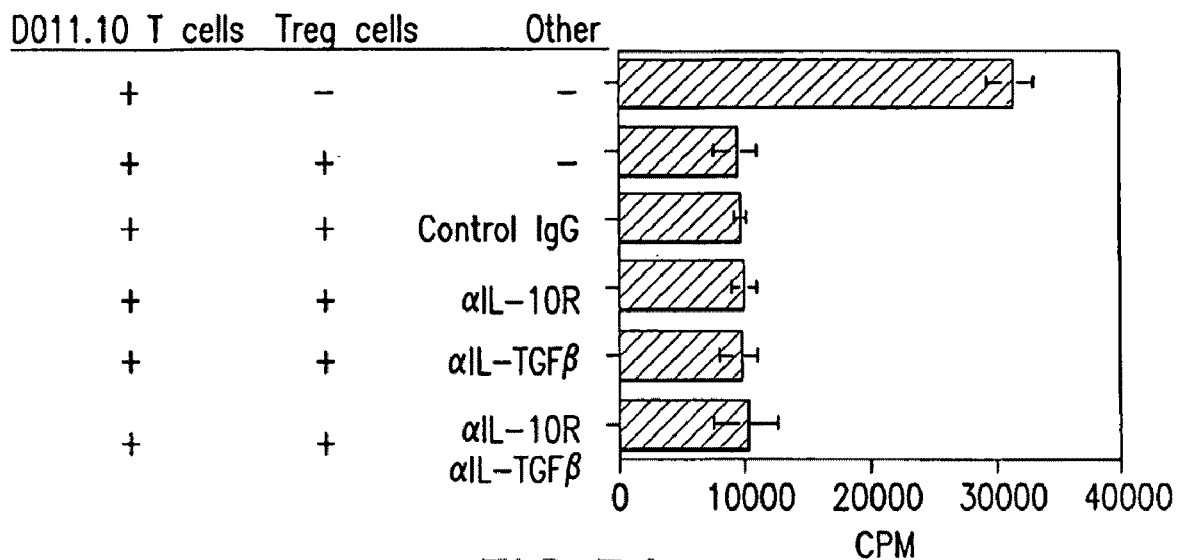
FIG. 5 shows IL-10 and TGFβ were not required for inhibitory function. A. PSI-APC Tregs were generated as in the legend to FIG. 3. 7 d later the T cells were harvested and co-cultured with DO11.10 CD4+ T cells with OVA-APCs in the presence of 5 μg/ml of different mAbs or control IgG as shown. $^3$H-TdR was added in the final 16 hrs of a 3-day culture. The results are expressed as mean CPM of triplicates+SD. B. CD4+ T cells from wild type (IL-10+/+) or IL-10−/− DO11.10 mice were cultured with OVA and PSI-pulsed APC for 7 days, and then cocultured with naïve DO11.10 CD4+ T cells in the presence of fresh OVA-pulsed APC. $^3$H-TdR was added in the final 16 hrs of a 3-day culture. The results were expressed as mean CPM of triplicates+SD. One representative of three experiments is shown.
Figure 5B:
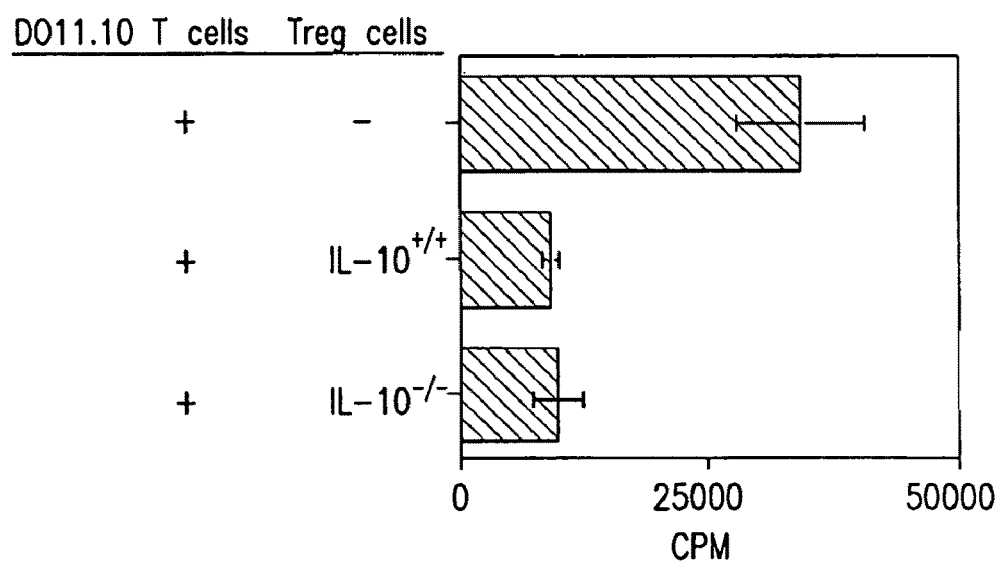

Inhibitory activity of Treg cells in vitro did not require IL-10 or TGFβ—To determine the potential role of TGFβ and IL-10 in the inhibitory function of PSI-APC Treg cells, anti-IL-10R1 and anti-TGFβ mAb were added into the cultures of Treg cells and naïve T cells in the presence of OVA-pulsed APC. Addition of 5 μg/ml anti-IL-10R1 and anti-TGFβ mAb, which partially reversed Tr1 inhibitory function in another system, separately or together did not abrogate the inhibitory function of PSI-APC Treg cells, indicating that IL-10 and TGFβ were not involved in the inhibitory function of PSI-APC Treg cells (FIG. 5A). To further investigate the role of IL-10, PSI-APC Treg were generated from CD4$^+$ T cells from wild type (IL-10$^{+/+}$) or IL-10 deficient (IL-10$^{-/-}$) DO11.10 mice. Both IL-10$^{+/+}$ and IL-10$^{-/-}$ Treg cells inhibited naïve T cell responses to OVA peptide stimulation, confirming that IL-10 is not required for PSI-APC Treg cell inhibitory function (FIG. 5B).

Figure 6A:
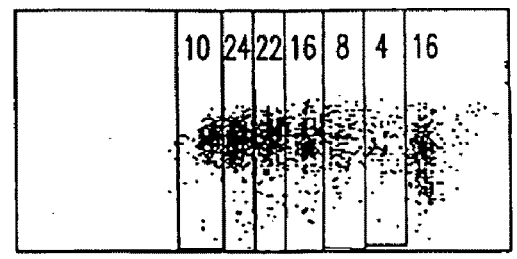
FIG. 6 shows cell-cell contact interactions were required for inhibitory function. A-C. PSI-APC Tregs were generated as in the legend to FIG. 3. CFSE labeled naïve DO11.10 CD4+ T cells were cultured with Treg cells in the same or different wells of the transwell plate with OVA-APCs for 3 days. The cells were harvested and stained with PE-KJ1-26 mAb and analyzed by flow cytometry. The percent of cells in each cell division is shown at the top of each profile. D. Treg cells were cultured with DO11.10 CD4+ T cells in the same or different wells of the transwell plate with OVA-APCs. $^3$H-TdR was added in the final 16 hrs of a 3-day culture. The results are expressed as mean CPM of triplicates+SD. One representative of three experiments is shown.
Figure 6B:
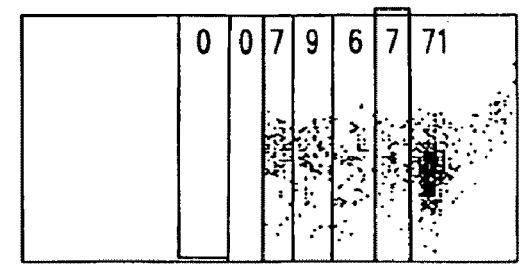
Figure 6C:
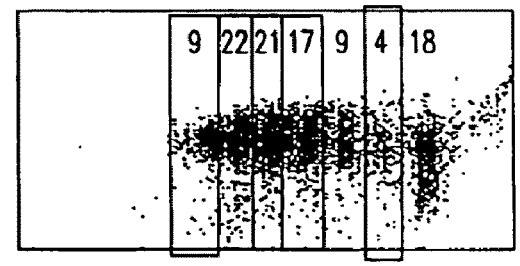
Figure 6D:
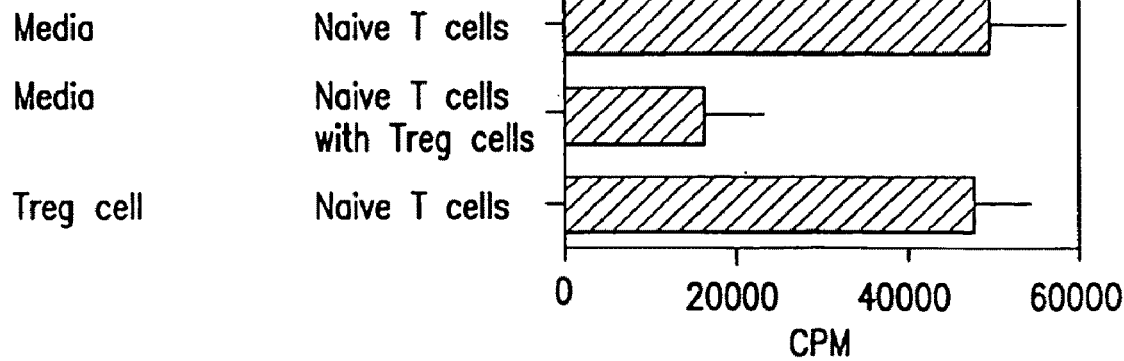

Cell-cell contact is required for PSI-APC Treg cell inhibitory function—To investigate whether other soluble factors or cell-cell contact were involved in PSI-APC Treg cell inhibitory function, transwell experiments were performed using CFSE-labeled naïve DO11.10 CD4$^+$ T cells. When CFSE-labeled naïve DO11.10 CD4$^+$ T cells were cultured alone in the lower wells with OVA-pulsed APCs, the naïve T cells proliferated vigorously with a large fraction of the T cells completing 5-6 cell divisions (FIG. 6A). When naïve CD4$^+$ T cells and Treg cells were cultured in the same wells, T cell cycle progression was inhibited with 71% of cells not dividing compared to 16% in the absence of Treg cells (FIG. 6B). However, when naïve CD4$^+$ T cells T cells were cultured in the lower wells and Treg cells in the upper wells, Treg cells no longer inhibited naïve T cell proliferation, in that most T cells completed 5-7 cell divisions (FIG. 6C). Similar data were obtained when $^3$H-Tdr TdR was used to measure T cell proliferation (FIG. 6D).

Figures 7A, 7B:
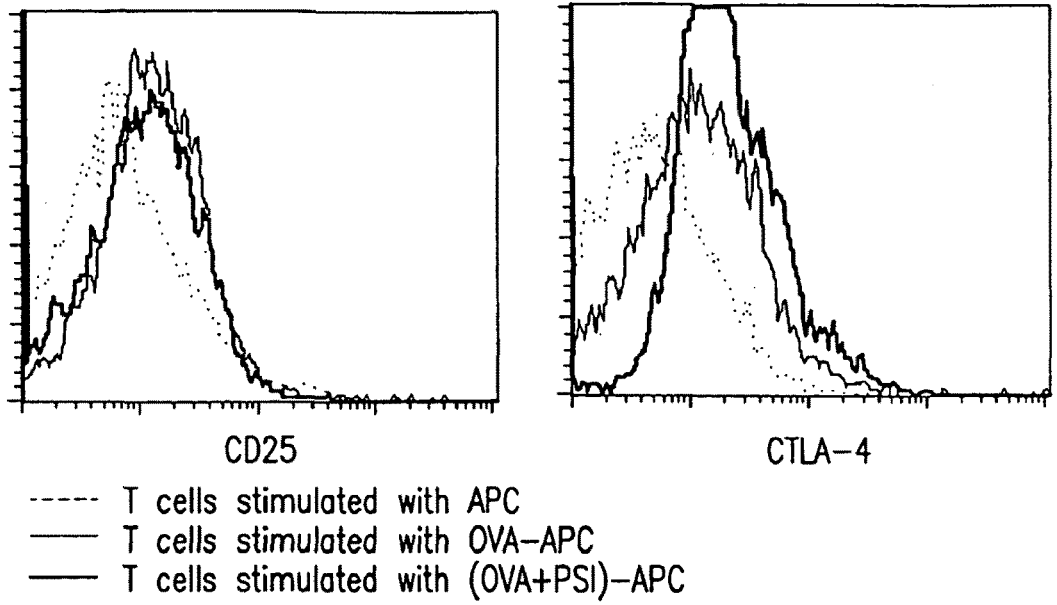
FIG. 7 shows CTLA-4 partially mediated PSI-APC Treg cell inhibitory function. PSI-APC Tregs were generated as in the legend to FIG. 3 using CD4+ T cells from DO11.10.RAG2−/− mice. 7 days later, the T cells were stained with PE-anti-CD25 mAb (A) or stained intracellularly with PE-anti-CTLA-4 mAb (B). C. PSI-APC Treg cells were co-cultured with DO11.10 CD4+ T cells with OVA-APCs in the presence of 5 μg/ml of anti-CTLA-4 mAb or control antibody. $^3$H-TdR was added in the final 16 hrs of 3-day culture. The results are expressed as mean CPM of triplicates+SD. One representative of three experiments is shown. * $p<0.05$ compared to the culture without addition of antibody.
Figure 7C:
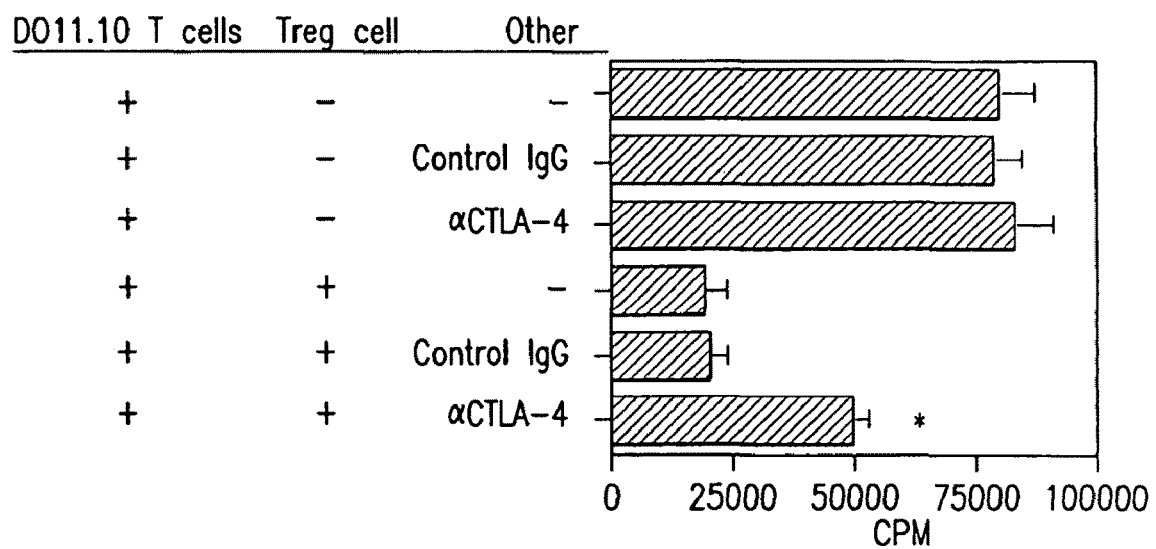

PSI-APC Treg cell required B7-CTLA-4 interactions for their inhibitory function—Naïve DO11.10 CD4$^+$ T cells stimulated with OVA-APC expressed a low level of CD25, and T cells cultured with OVA peptide-pulsed and PSI-treated APC had a similar level of CD25 (FIG. 7A). CTLA-4 expression on T cells cultured with OVA peptides and PSI-pulsed APC was modestly increased compared to that on T cells stimulated with OVA-APC (FIG. 7B). To investigate the potential functional role of increased CTLA-4 expression on PSI-APC Treg cells, anti-CTLA-4 mAb or control hamster antibody was added into the cultures of naïve DO11.10 CD4$^+$ T cells with Treg cells in the presence of OVA-APC. Addition of anti-CTLA-4, but not control hamster antibody significantly (p<0.05) reduced the level of reversed Treg cell-mediated inhibition (FIG. 7C).

Figure 8A:
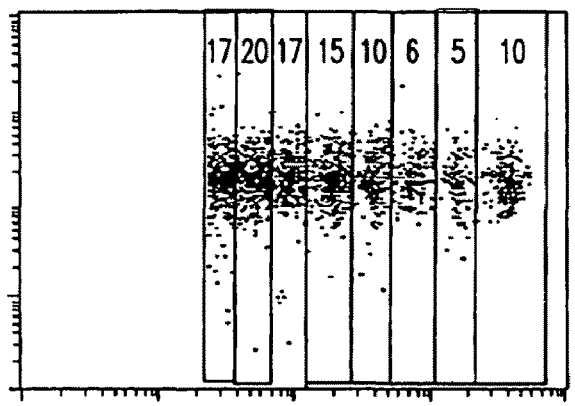
FIG. 8 shows PSI-APC Treg inhibited T cell response in vivo. DO11.10 CD4+ T cells were labeled with CFSE and $5\times10^6$ CFSE-labeled DO11.10 CD4 T cells were transferred together with either $5\times10^6$ unlabeled naive DO11.10 CD4 T cells (A) or unlabeled PSI-APC Treg cells (B) into BALB/c mice. One day later, the recipients were immunized with 100 μg/ml OVA in CFA i.p. The mice were killed at day five after immunization and CD4 T cells were isolated and stained with PE-KJ1-26 mAb and analyzed by flow cytometry. Each cell division was gated and analyzed for the percentage of the total cells. The percentage is shown for each cell division.
Figure 8B:
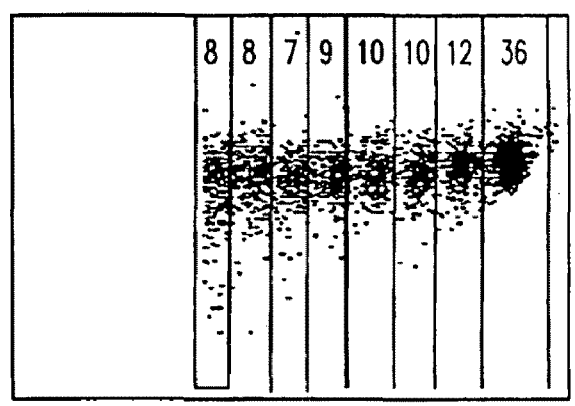

PSI-APC Treg cells expanded and inhibited CD4$^+$ T cell proliferation in vivo and prevented colitis development in a OVA-specific mouse model—To investigate whether PSI-APC Treg cells induced in vitro could function in vivo, 5×10$^6$ CFSE-labeled naïve DO11.10 RAG2$^{-/-}$ CD4$^+$ T cells were transferred together with same number of unlabeled DO11.10 RAG2$^{-/-}$ CD4$^+$ cells or of unlabelled PSI-APC Treg cells into BALB/c mice I.V. One day after cell transfer, the recipients were immunized with 100 μg OVA in CFA i.p. Five days later, the mice were sacrificed and CD4$^+$ T cells were isolated from spleen, stained with PE-KJ1-26 mAb, and analyzed by flow cytometry. CFSE-labeled naïve DO11.10 CD4$^+$ T cells proliferated strongly in vivo after immunization with OVA, with 90% of CFSE-labeled naïve T cells dividing and 69% completing 4 or more cell divisions (FIG. 8A). However, the proliferation of naïve DO11.10 CD4$^+$ T cells was significantly inhibited when PSI-APC Treg cells were co-transferred. In these recipients, 36% of the naïve T cells failed to divide and only 32% completed 4 or more cell divisions (FIG. 8B). These data indicate that PSI-APC generated Treg cells were able to inhibit T cell proliferation of OVA-specific T cells in vivo despite a strong antigenic challenge.

Figures 9A, 9B:
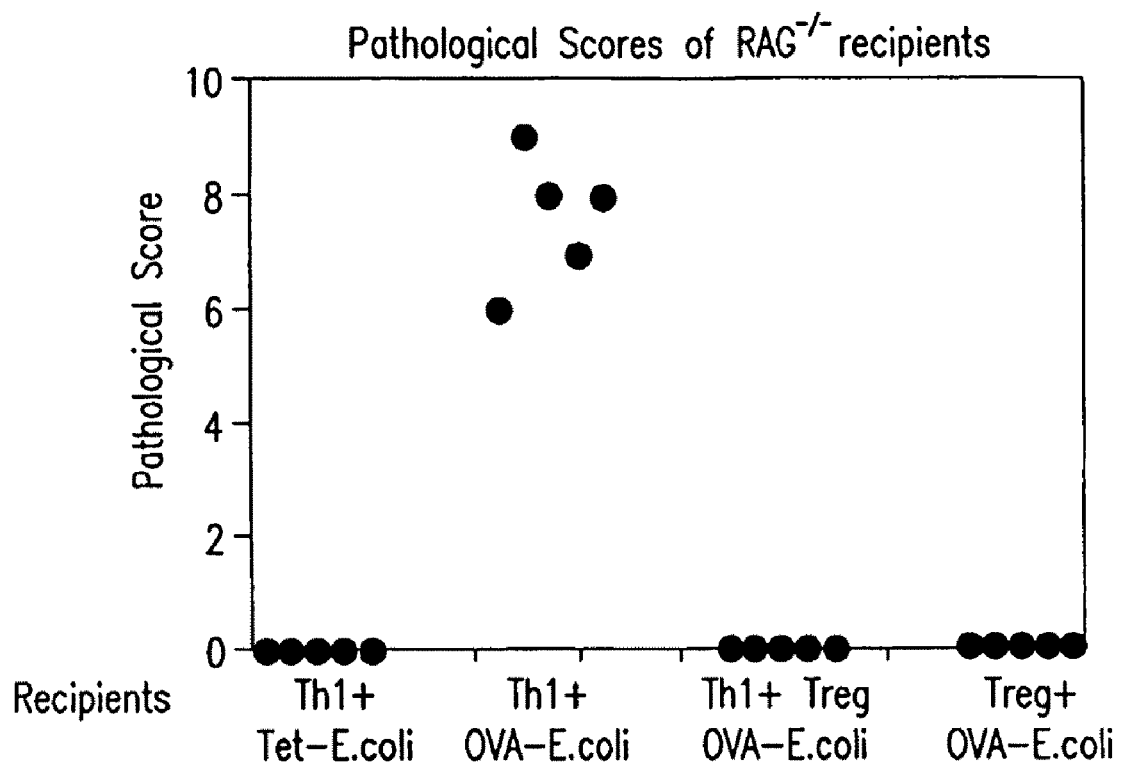
FIG. 9 shows PSI-APC Treg prevented colitis development induced by Th1 cells. BALB. RAG−/− mice were reconstituted with $5\times10^6$ in vitro pushed DO11.10 Th1 cells alone, $5\times10^6$ Th1 cells plus $5\times10^6$ PSI-APC Treg cells, or $5\times10^6$ PSI-APC Treg cells alone, prior to being given OVA-expressing E. coli into the colon. BALB.RAG−/− mice reconstituted with $5\times10^6$ in vitro pushed Th1 cells and then given Tet-expressing E. coli into the colon served as the negative control. Two months after transfer, the mice were sacrificed and histopathology was assessed. A. Pathological scores of RAG−/− recipients. Histological scoring was performed based on maximum score of 10. B. Colonic tissue IL-12 and IFNγ production. Five pieces (1 mm2/each) of colonic tissue from each mouse were cultured for 24 h, and IL-12 and IFNγ in supernatants were measured by ELISA. Data from two individual experiments are shown.

To determine whether PSI-APC Treg cells could regulate a pathogenic memory Th1 cell response in vivo, an OVA-specific colitis model was used. As shown in FIG. 9A, all RAG$^{-/-}$ mice that were reconstituted with in vitro-pushed DO11.10 Th1 cells and then colonized with OVA-expressing *E. coli* developed severe colitis with high amounts of IL-12 and IFNα production in colonic tissues (FIG. 9B). None of the control BALB.RAG2$^{-/-}$ mice that were reconstituted with Th1 cells and then colonized with Tet-expressing *E. coli* developed colitis, nor did any of the BALB.RAG$^{-/-}$ mice that were reconstituted with PSI-APC Treg cells alone and then given OVA-expressing *E. coli* develop disease. In addition, all the RAG$^{-/-}$ mice that were reconstituted with Th1 cells and PSI-APC Treg cells and then given OVA-expressing *E. coli* developed normally, and no colitis developed.

Example 3

Preparation of recombinant intestinal bacterial antigens—Five C3H/HeJ mice were sacrificed. The ceca were removed, opened, suspended in PBS, vortexed several times and the residual tissue was removed. A DNA expression library was generated from these C3H intestinal bacteria via digestion with SMA III restriction enzyme, isolation of 1-2 kb fragments and ligation into the poly-His pQE30 plasmid system (QIAGEN, Valencia, Calif.). Recombinant intestinal bacterial antigens (rIB) were expressed and gene products were screened by SDS-PAGE and immunoblot using mouse IgG1 anti-His (QIAGEN, Valencia, Calif.). Peptides >10 kDa were randomly chosen for further expression and purification on nickel columns (QIAGEN, Valencia, Calif.). Each DNA insert was sequenced and the sequences were compared to known genes listed in GenBank database (www.ncbi.nlm.nih.gov/GenBank/).

Parenteral immunization—Each rIB was incorporated in complete Freund's adjuvant along with ovalbumin as an internal positive control. These were injected intraperitoneally (i.p.) at 50 µg of each per mouse. C3H/HeJ mice were primed in groups of five at day 0 and a booster immunization was injected at day 28. Blood was collected at day −1, day 27 and day 35. Mice were sacrificed at day 35 and assays for CD4+ T cell responses were performed.

Mucosal immunization—Five mice/group were fed with OVA (100 µg/mouse) alone, OVA (100 µg/mouse) plus CT (10 µg/mouse), or OVA (100 µg/mouse) plus CBir1 flagellin (10 µg/mouse) in 0.5 ml PBS at day 1 and day 14. Serum and fecal pellets were collected at day 0 and day 28 and frozen at −80° C. until used for measurement of IgG and IgA antibodies by ELISA.

Assay of antigen-specific proliferation of CD4+ T cells—Splenic CD4+ T cells were isolated from naïve mice or from immunized mice at day 35 and placed into a cell suspension by straining through a 100 µm sieve. After washing twice the red blood cells were lysed by TrisNHCl. The cells were washed and CD4+ T cells were isolated via positive selection with anti-CD4 magnetic beads (BD Pharmingen, San Diego, Calif.) using the manufacturer's protocol. CD4+ T cells were cultured at $2\times10^5$ cells/well in triplicate in the presence of $2\times10^5$ APCs/well plus 50 µg/ml rIB, or 50 µg/ml OVA. For APCs, splenocytes from C3H/HeJ mice were isolated, irradiated with 30 Gy and added to the T cell culture. Cells were cultured in complete medium containing RPMI 1640, 5% FCS, 10 mM HEPES, 2 mM sodium pyruvate, 2 mM L-glutamine, 100 U/ml penicillin and 100 µg/ml streptomycin for 4 days at 37° C. in 5% $CO_2$ humidified air. For the last 18 h of incubation 0.5 µCi of [$^3$H]thymidine (New England Nuclear, Boston, Mass.) was added to each well. The cells were harvested and proliferation was measured in a β scintillation counter.

Generation of bone marrow derived dendritic cells—Bone bne marrow cells from femurs isolated from 5 mice were pooled for each experiment, and suspended at $1\times10^6$ cells/ml in complete RPMI 1640 media containing 10% heat-inactivated fetal calf serum (Atlanta Biologicals, Norcross, Ga.), 25 mM HEPES buffer, 2 mM sodium pyruvate (BioWhittaker, Walkersville, Md.), 50 mM 2-mercaptoethanol, 2 mM L-glutamine (Cellgro Mediatech, Herndon, Va.), 100 u/ml Penicillin, and 100 µg/ml Streptomycin (Cellgro Mediatech, Herndon, Va.). The cells were cultured in the presence of 10 ng/ml murine GM-CSF in 24-well plates (Corning, Corning, N.Y.) at 37° C. in 5% $CO_2$ in humid air. Nonadherent cells were collected at day 6 of culture and put back into culture in media containing 10 ng/ml murine GM-CSF. After 3 additional days of culture, nonadherent cells were collected and washed 3 times with fresh media. More than 95% of the non-adherent cells were CD11c+, CD3−, B220− when checked by flow cytometry. The cells were plated at $1\times10^6$/ 0.5 ml per well in 48-well plates (Costar, Corning, N.Y.), cultured with various antigens as indicated, and washed.

Isolation of Peyer's patches B cells IgA production in vitro—Peyer's patches were excised from the intestine of C3H/HeJ mice, washed once with RPMI 1640 (Cellgro; Mediatech, Washington, D.C.), and single cells dissociated with collagenase (Type V, Sigma, St. Louis, Mo.) at a concentration of 0.5 mg/ml in RPMI 1640 with 100 U/ml penicillin, and 100 µg/ml streptomycin for 20 min at 37° C. The cell dissociation step was performed twice more using fresh collagenase solution each time. Mononuclear cells were collected, washed and resuspended in RPMI 1640 containing 10% heat-inactivated FCS. B cells were isolated by negative selection by removing CD4+, CD8+, Mac-1+, CD11c+ cells using magnetic activated cell sorting (Miltenyi Biotec, Auburn, Calif.). $2\times10^5$ Peyer's patch B cells were cultured with $5\times10^4$ BMDC that had been pulsed with various antigens overnight. Five days later, culture supernatants were collected and antigen-specific IgA measured by ELISA.

Antibody measurement by ELISA—ELISA plates were coated with rIB or other antigens (2 µg/ml in PBS) overnight at 4° C. After washing t in PBS, the plates were blocked with PBS containing 1% bovine serum albumin (BSA) and washed again. Serial dilutions of sera or fecal pellets were added and the plates incubated for 24 h at 4° C. Plates were washed again in PBS/0.05% Tween. Affinity purified, biotin labeled, goat anti-mouse immunoglobulin G (1:2000) or goat anti-mouse IgA was added for 2 h at room temperature (KPL, Gaithersburg, Md.). After washing, the plates were incubated for one hour with the horseradish peroxidase labeled streptavidin at 1:4000 (ICN Biomedicals, Aurora, Ohio) at room temperature and washed again. The plates were developed by addition of 50 µl TMB substrate (KPL, Gaithersburg, Md.) and the reaction was stopped with 50 µl 1M sulfuric acid. Plates were read by an ELISA reader at 480 nm (Bio-Tek Instruments, Winooski, Vt.).

Statistics—The results were expressed as the mean+/−the standard error of the mean. The significance of the difference in means was determined by the unpaired Student's t-test using Graph Pad Prism 3.0 software (Innotech, Schonaich, Germany).

Cloning of recombinant intestinal bacterial antigens—To determine the immune response against defined bacterial antigens, 20 recombinant intestinal bacterial antigens (rIB) were randomly expressed from normal C3H/HeJ cecal genome DNA, sequenced, and purified. No nucleotide matches to known genes were detected.

Absence of systemic B cell and T cell reactivity to rIB in normal mice—To study the systemic immune responses to rIB in normal mice, serum IgG and splenic CD4+ T cell response to each of the 20 rIB was measured in normal C3H/HeJ mice. No serum IgG could be detected to any rIB or to the control antigen OVA (IgG antibody titers <1:20) (Table 2 and FIG. 10). To determine the response of normal mice to immunization with each rIB, C3H/HeJ mice were injected with each rIB plus OVA in CFA and boosted on day 28. The mice were bled at day −1, 27, 35, and then sacrificed to measure the splenic CD4+ T cell response. After the priming immunization a strong serum IgG response ($1:10^4$-$1:10^8$, median $1:10^6$) was detected to all rIB, comparable to the serum IgG response to OVA. After the booster immunization, the serum IgG response to rIB antigens was appropriately enhanced ($1:10^5$-$1:10^{10}$, median $1:10^7$), again similar to the response to OVA (Table 2). FIG. 1 shows the serum IgG response to rIB14 and rIB19 which are representative of the response to all 20 rIB.

Figures 11A, 11B:
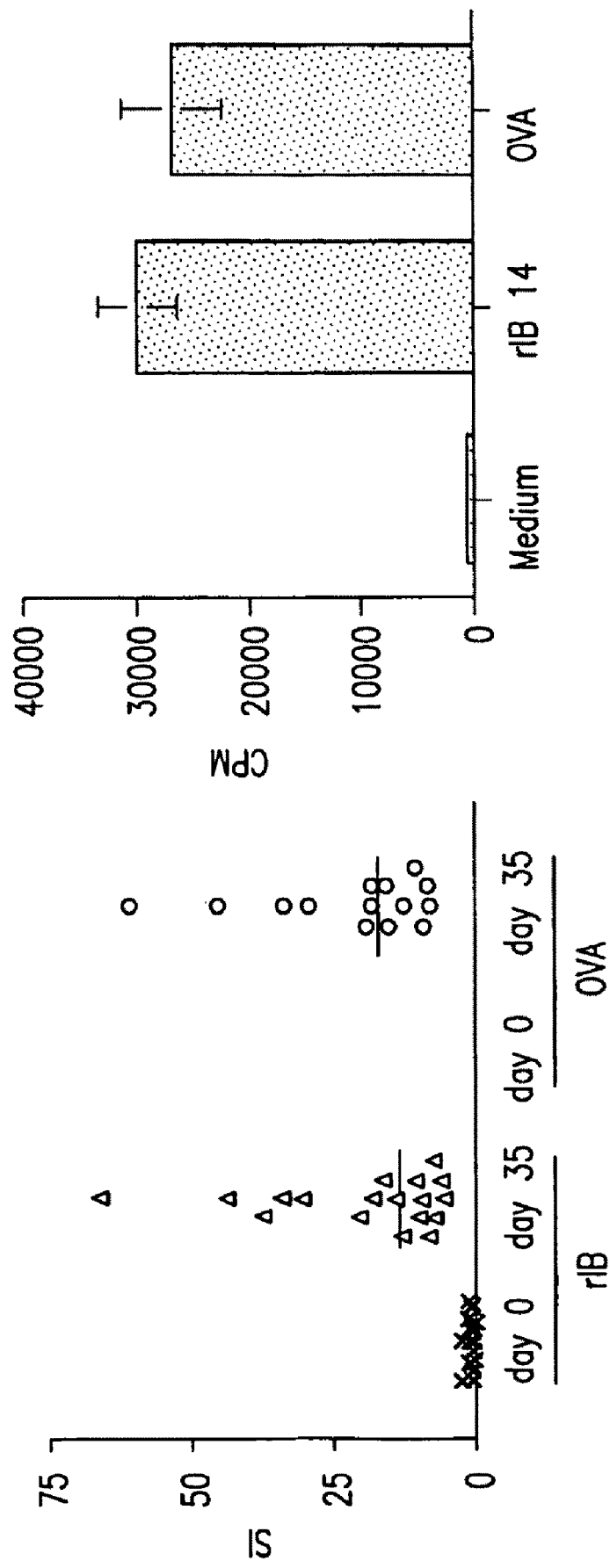
FIG. 11 shows proliferation of C3H/HeJ CD4+ T cells of non-immunized versus immunized mice to rIB and OVA. Splenic CD4+ T cell proliferation to rIB and OVA pre and post-immunization. A. Stimulation indices (SI) as defined as defined in Methods of CD4+ T cells before (day 0) and 1 wk after immunization (day 35) with all 20 rIB or OVA. Each data point is the mean SI response of 5 mice to one of the 20 rIBs. The median SI (post immunization median$_{rIB}$ 13.4 and median$_{OVA}$ 17.1) of the entire set is shown as a horizontal line. B. CD4+ T cell proliferation on day 35 post immunization with rIB 14 as representative data. $4\times10^5$ CD4+ T cells were cultured per well with an equal number of antigen-pulsed APC (50 μg rIB or OVA). 3H-TdR was added to the wells for the last 18 h of a five-day culture. Results are expressed as mean cpm±SD of triplicate cultures.

Similar results were obtained for the T cell response to rIB: no proliferative response could be identified to any rIB or to OVA in unimmunized mice (SI<3; FIG. 11A). However, a strong T cell immune response was observed to each rIB after immunization, which was comparable to the response to OVA. FIG. 11B shows the T cell response to rIB14 as a representative for the other 20 rIB. Taking the results from all twenty immunizations together, the median stimulation index to the 20 rIB was 13.4 vs. 17.1 for OVA (FIG. 11A), which was not statistically different.

To investigate the immune response to the rIB in colitic mice, sera were collected from ten colitic C3H/HeJBir.IL-10−/− mice (age >4 months) and the serum IgG response was measured against each of the twenty rIB. Significantly increased endpoint IgG titers against all 20 rIB were obtained compared with the titers from non-colitic C3H/HeJ mice (p<0.05), although the response in colitic C3H/HeJBir.IL-10$^{-/-}$ mice was much lower than the immune response in parenterally immunized C3H/HeJ mice. In any single mouse, the presence or absence of an antibody response to a given rIB appeared to be stochastic.

Figure 12:
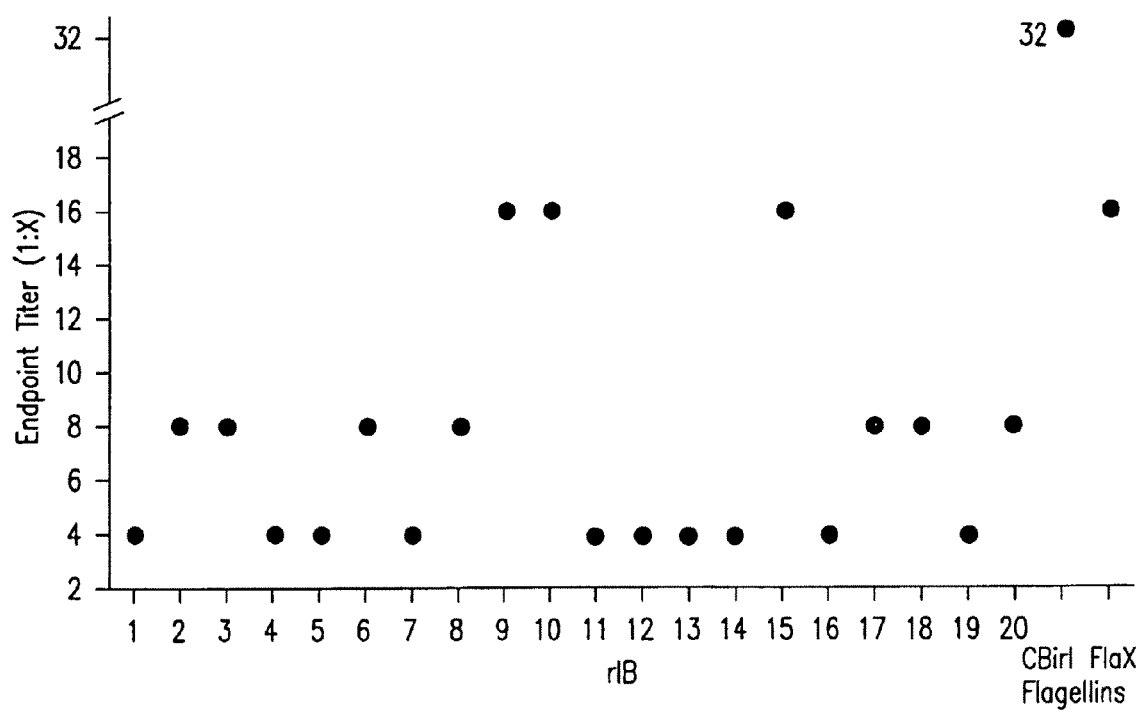
FIG. 12 shows intestinal IgA anti-rIB response to rIB in normal mice. IgA anti-rIB immune response of normal, non-immunized C3H/HeJ mice to each of the twenty rIB antigens and to two commensal flagellins, CBir1 and FlaX. IgA was measured by antigen specific ELISA and data were expressed as endpoint titers of two-fold dilutions.
Figure 13:
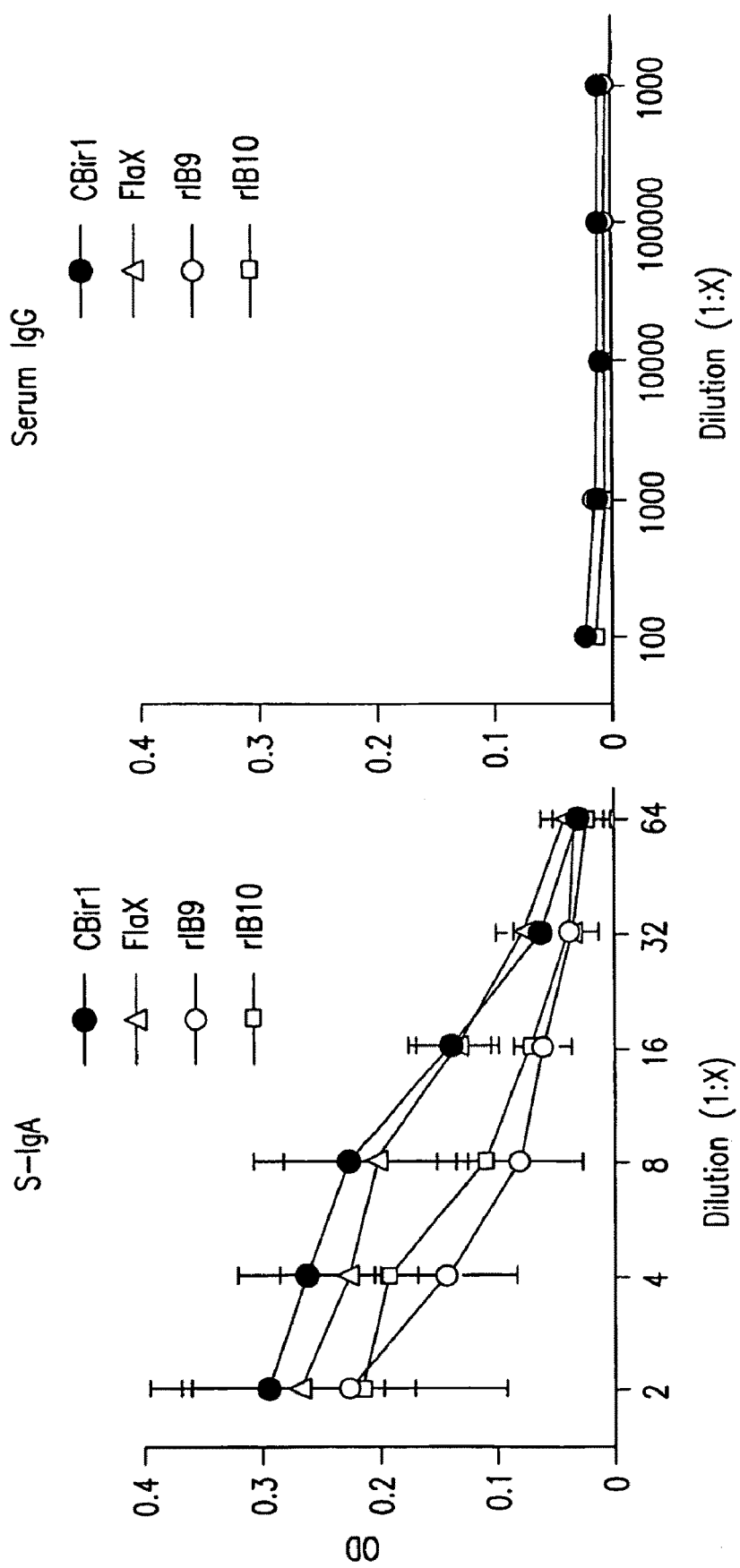
FIG. 13 shows intestinal IgA and serum IgG response to enteric bacterial flagellins. Serum and fecal pellets were collected from a group of 5 normal, non-immunized C3H/HeJ mice and intestinal IgA and serum IgG antibodies measured by ELISA. A, intestinal IgA and B, serum IgG response to CBir1 flagellin, FlaX flagellin, rIB9, and rIB10. Data are expressed as OD-units at serial two-fold dilution for IgA and serial 10-fold dilution for IgG. The response to rIB 9 and rIB10 are shown for comparison.

Intestinal IgA to rIB was present in normal mice—To determine the mucosal response to rIB, fecal pellets were collected from normal C3H/HeJ mice, and intestinal IgA antibodies were measured against each rIB by ELISA. All mice showed intestinal IgA reactivity to all 20 rIBs with half of the mice demonstrating a substantial titer of 1:8 or higher (FIG. 12), even though the same mice had no detectable serum IgG antibody to the same rIB antigens.

Intestinal immune response to commensal flagellins—Enteric bacterial flagellins have been identified recently as immunodominant antigens in animal models of IBD and in patients with Crohn's disease. To determine the immune responses of normal mice to such flagellins, serum IgG and pellet IgA reactivity to CBir1 and FlaX flagellin were determined and compared to the non-flagellin antigens, rIB9 and rIB10. Interestingly, normal mice showed a higher level of IgA response to flagellins than to rIB9 and rIB10 but no serum IgG response to either flagellin was detected (FIG. 14). There was also no splenic CD4$^+$ T cell proliferative response detected to either flagellin.

Figure 14A:
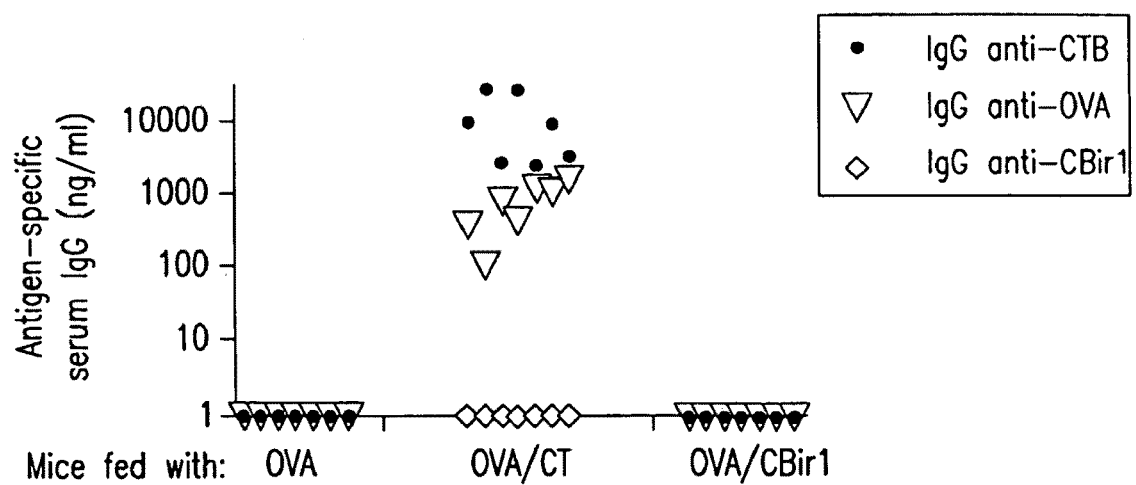
FIG. 14 shows mucosal immunization with OVA plus CBir1 flagellin or cholera toxin as adjuvant. Groups of five mice were gavaged i.g. on days 1 and 14 with 100 μg OVA alone, 100 μg OVA plus 10 μg CT, or 100 μg OVA plus 10 μg CBir1 flagellin. On day 28, serum and stool pellets were collected from each mouse, and the individual serum IgG and pellet IgA responses against OVA, CBir1, and B subunit of CT (CTB) were measured by ELISA. A, antigen-specific serum IgG; B, antigen-specific IgA in pellets.
Figure 14B:
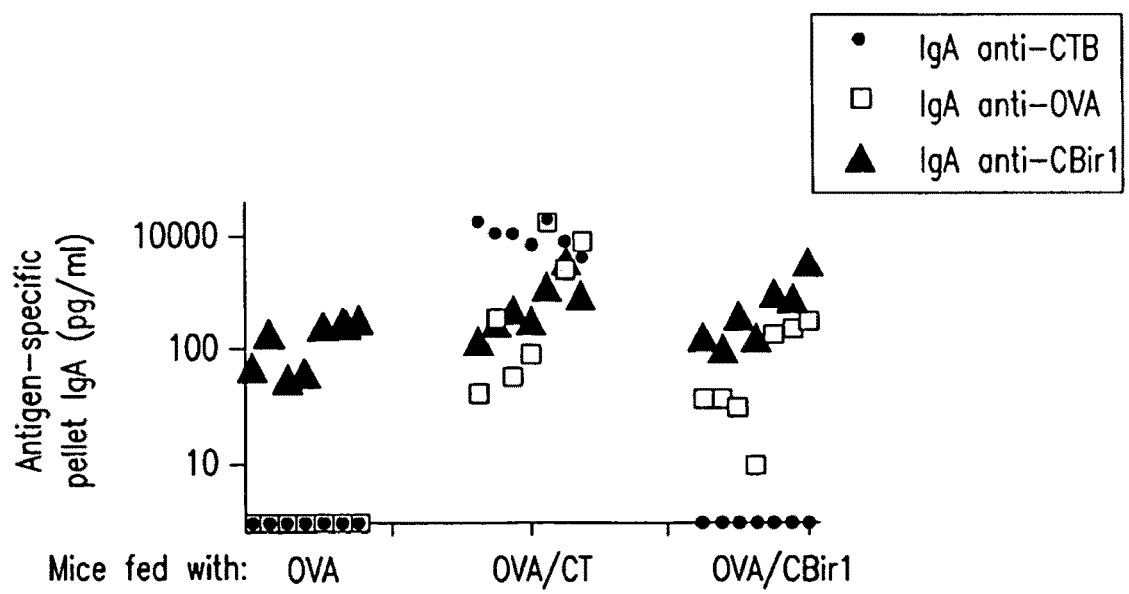

Mucosal immunization with a neoantigen plus a commensal bacterial adjuvant—Flagellins activate host cells through TLR5 and have been shown to have parenteral adjuvanticity, thus CBir1 flagellin was used as a commensal bacterial adjuvant. For the neoantigen, OVA, an exogenous foreign antigen that has been used in many oral immunization and oral tolerance studies, was used. As a positive control a group given OVA plus cholera toxin, a well-defined mucosal adjuvant, was included. As shown in FIG. 14A, mice fed with OVA alone produced no serum IgG response to OVA. Mice fed with OVA and CT demonstrated a strong serum IgG response to OVA, as well as to CT itself. In contrast, mice fed with OVA and CBir1 flagellin did not develop serum IgG response either to OVA or to CBir1 flagellin (FIG. 14A). Intestinal IgA responses were measured in the same groups (FIG. 14B). Mice gavaged with OVA alone produced virtually no intestinal IgA to OVA. Mice gavaged with OVA plus CT had strong intestinal IgA response to both OVA and to CT. Mice gavaged with OVA plus CBir1 flagellin had equally strong intestinal IgA anti-OVA responses compared to the mice fed with OVA plus CT. All mice had pre-existing intestinal IgA responses to CBir1 flagellin; gavage with CBir1 flagellin enhanced such IgA response two to three-fold.

Dendritic cell-induced B cell production of IgA is mediated by BAFF (BLys)—Whether dendritic cells could stimulate specific IgA response to commensal bacterial antigens in the absence of T cell help was also examined. To this end, PP B cells of normal C3H/HeJ mice were isolated and cultured with BMDC that had been pulsed with a selected rIB or with CBir1 flagellin. Antigen-specific IgA in supernatants was measured by ELISA. As shown in Table 3, when cultured with CBir1-pulsed BMDC, PP B cells produced IgA specific for CBir1 flagellin but not for either rIB9 or rIB15. In a similar fashion, PP B cells cultured with rIB9-pulsed BMDC produced IgA specific for rIB9 but not for either rIB15 or CBir1 flagellin. In contrast, PP B cells cultured with rIB15-pulsed BMDC did not produce IgA to rIB15 or to the other antigens, indicating that PP B cells were primed to some riBs but not to all.

Figure 15:
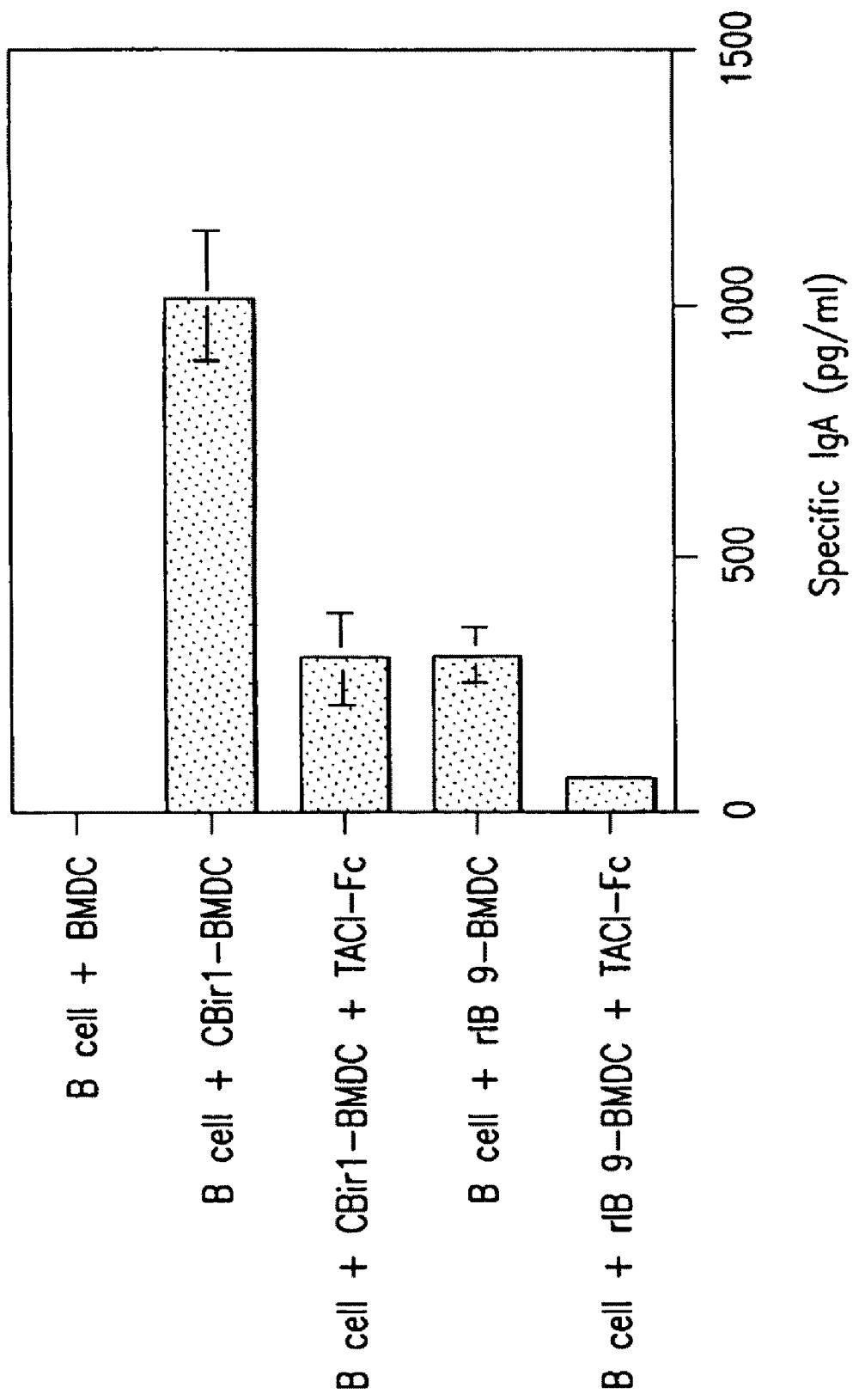
FIG. 15 shows dendritic cell-induction of B cell IgA production and its inhibition by bockade of BAFF by a TACI-Ig fusion protein. BMDC were pulsed with CBir1 flagellin or rIB9 overnight and cultured with B cells isolated from Peyer's patches of normal C3H/HeJ mice in the presence or absence of 10 μg/ml of TACI-Ig fusion protein. Culture supernatants were collected five days later and antigen-specific IgA measured by ELISA.

Recently, DC-derived soluble factor BAFF (Blys), a member of TNF superfamily, has been shown to bind its receptor(s) on B cells and provide a crucial signal required for antibody production in T-independent immune responses. To test whether BAFF (BLys) was involved in the antigen-specific IgA production of PP B cells cultured with antigen-pulsed BMDC, a BAFF inhibitor, TACI-Fc fusion protein, was added into the culture of PP B cells with CBir1-, or rIB9-pulsed BMDC. Blockade of BAFF (BLys) greatly decreased antigen-specific IgA production by PP B cells for both rIB9 and CBir1 flagellin (FIG. 15).

Example 4

Figure 16:
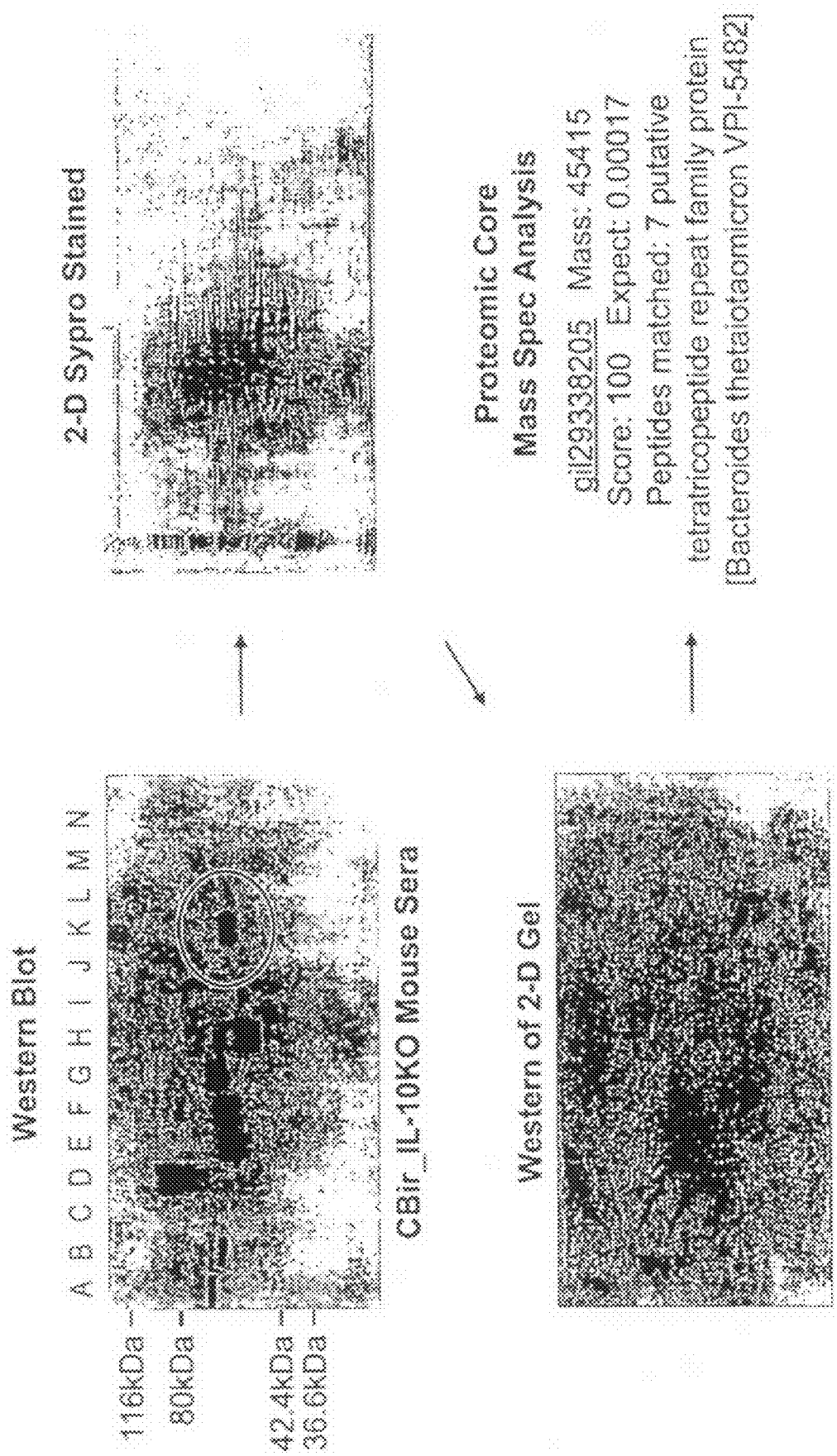
FIG. 16 shows the identification of colitogenic antigens from Bacteroides using a proteomic approach.

Polyacryamide gel electrophoresis was performed using whole cell lysates of *Bacteroides thetaiotaomicron* and *Bacteroides fragilis*. Western blotting of the gels was then performed. The blots were probed for serum IgG reactivity from colitic vs normal mice. Having detected a specific band in each that reacted to B6.1L-10−/− mouse sera but not normal B6 mouse sera, the same sample was used in a 2-D gel analysis. Duplicate gels were run and one was western blotted in the same manner as above. The other gel was stained for proteins. The images of each were overlaid. The positive spot from the western blot was used for referencing and picking of protein spots from the stained gel. The resulting protein was sequenced with mass spectrometry (FIG. 16). A comparison of the resulting peptide fragments to the genome data of each organism yielded significant matches. SEQ ID NOs: 81 and 83 represent the proteins identified. SEQ ID NOs: 80 and 82 represent the nucleic acid sequences capable of encoding the proteins of SEQ ID NOs: 81 and 83, respectively.

TABLE 2

Endpoint Titer of antibody responses to rIB and OVA*

| | IgG anti-rIB ($10^X$)† | | | IgG anti-OVA ($10^X$)† | | | IgG anti-rIB ($10^X$)‡ |
|---|---|---|---|---|---|---|---|
| rIB | Day 0 | Day 27 | Day 35 | Day 0 | Day 27 | Day 35 | IL-10KO (Day 0) |
| rIB1 | <2 | 6 | 6 | <2 | 6 | 7 | 2 |
| rIB2 | <2 | 7 | 7 | <2 | 7 | 7 | 2 |
| rIB3 | <2 | 6 | 7 | <2 | 6 | 7 | 3 |
| rIB4 | <2 | 6 | 7 | <2 | 7 | 7 | 3 |

TABLE 2-continued

Endpoint Titer of antibody responses to rIB and OVA*

| rIB | IgG anti-rIB ($10^X$)† | | | IgG anti-OVA ($10^X$)† | | | IgG anti-rIB ($10^X$)‡ |
|---|---|---|---|---|---|---|---|
| | Day 0 | Day 27 | Day 35 | Day 0 | Day 27 | Day 35 | IL-10KO (Day 0) |
| rIB5 | <2 | 8 | 8 | <2 | 7 | 8 | 3 |
| rIB6 | <2 | 6 | 6 | <2 | 6 | 7 | 2 |
| rIB7 | <2 | 4 | 5 | <2 | 5 | 5 | 3 |
| rIB8 | <2 | 3 | 5 | <2 | 5 | 6 | 2 |
| rIB9 | <2 | 4 | 7 | <2 | 5 | 8 | 4 |
| rIB10 | <2 | 5 | 7 | <2 | 5 | 7 | 3 |
| rIB11 | <2 | 6 | 7 | <2 | 7 | 8 | 3 |
| rIB12 | <2 | 6 | 8 | <2 | 6 | 7 | 2 |
| rIB13 | <2 | 4 | 7 | <2 | 5 | 6 | 3 |
| rIB14 | <2 | 6 | 9 | <2 | 7 | 8 | 3 |
| rIB15 | <2 | 5 | 7 | <2 | 6 | 7 | 3 |
| rIB16 | <2 | 5 | 7 | <2 | 5 | 5 | 2 |
| rIB17 | <2 | 6 | 9 | <2 | 7 | 7 | 3 |
| rIB18 | <2 | 5 | 7 | <2 | 4 | 6 | 3 |
| rIB19 | <2 | 6 | 9 | <2 | 6 | 8 | 2 |
| rIB20 | <2 | 7 | 9 | <2 | 6 | 8 | 3 |

*The data shown are the exponents of the endpoint titers ($10^X$) for each antigen.
†C3H/HeJ mice were immunized with 50 µg rIB and 50 µg OVA in CFA i.p. at day 1 and day 14, and bled at day 0, day 27, and day 35. Serum IgG against rIB or OVA was measured by ELISA.
‡Serum IgG anti-rIB of non-immunized, but colitic C3H/HeJBir.IL-10 deficient mice for comparison.

TABLE 3

Antigen-specific PP B cell IgA production in cultures with antigen-pulsed BMDC*

| DC pulsed with | IgA anti-CBir1 (pg/ml) | IgA anti-rIB9 (pg/ml) | IgA anti-rIB15 (pg/ml) |
|---|---|---|---|
| Media | <30 | <30 | <30 |
| CBir1 | 978 | <30 | <30 |
| RIB9 | <30 | 733 | <30 |
| RIB15 | <30 | <30 | <30 |

*BMDC were pulsed with bacterial antigen over night and then cultured with PP B cells of C3H/HeJ mice for 5 days. IgA responses were measured by antigen-specific ELISA

---

What is claimed is:

1. An isolated polypeptide comprising an amino acid sequence having at least 97% identity to the amino acid sequence of SEQ ID NO: 24.

2. A solid support comprising the polypeptide of claim 1 attached to the solid support.

3. A fusion protein comprising at least one polypeptide of claim 1.

4. A composition comprising a physiologically acceptable carrier and a polypeptide of claim 1.

5. A kit comprising the polypeptide of claim 1 immobilized on a solid support.

6. An immunogenic composition comprising the polypeptide of claim 1, an antigen and a suitable carrier.

* * * * *